US006900049B2

(12) United States Patent
Yu et al.

(10) Patent No.: US 6,900,049 B2
(45) Date of Patent: May 31, 2005

(54) ADENOVIRUS VECTORS CONTAINING CELL STATUS-SPECIFIC RESPONSE ELEMENTS AND METHODS OF USE THEREOF

(75) Inventors: De Chao Yu, Foster City, CA (US); Daniel R. Henderson, Palo Alto, CA (US)

(73) Assignee: Cell Genesys, Inc., San Francisco, CA (US)

( * ) Notice: Subject to any disclaimer, the term of this patent is extended or adjusted under 35 U.S.C. 154(b) by 0 days.

(21) Appl. No.: 09/392,822

(22) Filed: Sep. 9, 1999

(65) Prior Publication Data

US 2001/0053352 A1 Dec. 20, 2001

Related U.S. Application Data

(60) Provisional application No. 60/099,791, filed on Sep. 10, 1998.

(51) Int. Cl.[7] .................. A01N 63/00; A61K 39/00; C12N 15/00; C12N 5/00; C12P 21/06
(52) U.S. Cl. .................. 435/320.1; 435/69.1; 435/325; 424/93.1; 424/191.1; 536/231
(58) Field of Search .................. 514/44; 435/320.1, 435/69.1, 5, 325; 424/93.6, 233.1, 191.1; 536/23.5

(56) References Cited

U.S. PATENT DOCUMENTS

| 5,648,478 | A | | 7/1997 | Henderson |
| 5,698,443 | A | | 12/1997 | Henderson et al. |
| 5,834,306 | A | * | 11/1998 | Webster et al. .......... 435/320.1 |
| 5,871,726 | A | * | 2/1999 | Henderson et al. ........ 424/93.2 |
| 5,998,205 | A | * | 12/1999 | Hallenbeck et al. ........ 435/325 |
| 2003/0095989 | A1 | * | 5/2003 | Irving et al. ............. 424/233.1 |

FOREIGN PATENT DOCUMENTS

| EP | 0845537 A1 | 6/1998 |
| EP | WO 98/39466 A2 | 9/1998 |
| EP | WO 98/39466 A3 | 9/1998 |
| WO | WO 95/11984 A2 | 5/1995 |
| WO | WO 95/14100 A2 | 5/1995 |
| WO | WO 95/14100 A3 | 5/1995 |
| WO | WO 96/17053 A1 | 6/1996 |
| WO | WO 96/34969 A2 | 11/1996 |
| WO | WO 96/34969 A3 | 11/1996 |
| WO | WO-97/01358 | * 1/1997 |
| WO | WO 98/06864 A2 | 2/1998 |
| WO | WO 98/06864 A3 | 2/1998 |
| WO | WO 98/13508 A1 | 4/1998 |
| WO | WO 98/35028 A3 | 8/1998 |
| WO | WO 98/35028 A2 | 8/1998 |

OTHER PUBLICATIONS

Cuevas et al. Cancer Res 63:6877–6884, October 15, 2003.*
Hernandez–Alcoceba et al. Human Gene Therapy 13:1737–1750, Sep. 20, 2002.*
Li et aI abstract 445 from ASGT 71h Annual Meeting, Jun. 2004.*
Babiss et. al.; Cellular Promoters Incorporated into the Adenovirus Genome; 1987, J. Mol. Biol. 193: 643–650.*
Shi et. al.; Modulation of the Specificity and Activity of a Cellular Promoter in an Adenoviral Vector; 1997, Human Gene Therapy 8: 403–410.*
Bett et. al., packaging Capacity and Stability of Human adenovirus Type 5 Vectors, 1993, Journal of Virology, Vol. 67, No. 10: 5911–5921.*
Anderson; Human gene therapy, 1998, Nature Vol. 392: 25–30.*
Verma et. al.; Gene therapy–promises, problems and prospects, 1997, Nature, Vol. 389:239–242.*
Curiel; Strategies to Adapt Adenoviral Vectors forTargeted Delivery, 1999, Gene Therapy Strategies:158–171.*
Jam; Delivery of moleculat and cellular medicine to solid tumors, 1997, Journal of Controlled Release 53: 49–87.*
Hobbs; Regulation of transport pathways in tumor vessels: Role of tumor type and microenvironment, 1998, Proc. Natl. Acad. Sci. Vol. 95: 4607–4612.*
Walther; Targeted Vectors for Gene therapy of Cancer and Retrpvoral Infections, 1996, Molecular Biotechnology Vol. 6: 2670286.*
Dachs; Targeted Gene Therapy to Cancer: A Review. 1997, Oncolog Research Vol. 9: 313–325.*
Advani et. al.; Radiogenetic Therapy: On the Interaction of Viral therapy and Ionizing Radiation for improving Local Control of Tumors, 1997, Seminars in Oncology Vol. 24. No. 6: 633–638.*
Parr et. al..; Tumor–selective transgene expression in vivo mediated by an E2F–responsive adenoviral vector, 1997, Nature medicine Vol. 3, No. 3: 1145–1949.*
Orkin et al., "Report and Recommendations of the Panel to Assess the NIH Investment in Research on Gene Therapy." pp. 1–20, Dec. 1995.*
Miller et al., "Targeted Vector for Gene Therapy." FASEB, Vol. 9: 190–199, Feb. 1995.*
Ledley, F 0.,"Pharmaceutical Approach to Somatic Gene Therapy." Pharmaceutical Research vol. 13: 1595–1613, Nov. 1996.*
Eck et al "Gene–Based Therapy–Chapter 5.", Goodman & Gilman's The Pharmacological Basis of Therapeutics–Ninth Edition, McGraw–Hill: 77–101, 1996.*

(Continued)

*Primary Examiner*—Joseph Woitach
(74) *Attorney, Agent, or Firm*—Pamela J. Sherwood; Boziecevic, Field & Francis LLP; Linda R. Judge

(57) ABSTRACT

The present invention provides adenoviral vectors comprising cell status-specific transcriptional regulatory elements which confer cell status-specific transcriptional regulation on an adenoviral gene. A "cell status" is generally a reversible physiological and/or environmental state. The invention further provides compositions and host cells comprising the vectors, as well as methods of using the vectors.

31 Claims, 26 Drawing Sheets

OTHER PUBLICATIONS

Abe et al. (1993). "Characterization of Cis–Acting Elements Regulating Transcription of the Human DF3 Breast Carcinoma–Associated Antigen (N4UCI) Gene," *Proc. Natl. Sci. USA* 90: 282–286.

Arnberg et al. (1997). "Fiber Genes of Adenoviruses with Tropism for the Eye and the Genital Tract," *Virol.* 227: 239–244.

Ausubel et al. eds. (1987). Current Protocols in Molecular Bioloev Suppl. 30 Sec. 7.7.18, Table 7.7.1.

Bailey et al. (1993). "Enteric Adenovirus Type 40: Expression of EIB Proteins in Vitro and in Vivo," *Virol.* 193: 631–641.

Bailey et al. (1994). "Cell Type Specific Regulation of Expression from the Ad40 E1 B Promoter in Recombinant Ad5/Ad40 Viruses," *Virol.* 202: 695–706.

Behringeret al. (1988). "Dwarf Mice Produced by Genetic Ablation of Growth Hormone–Expressing Cells," *Genes Dev.* 2: 453–461.

Berkner et al. (1983). "Generation of Adenovirus by Transfection of Plasmids," *Nuc. Acid Res.* 11(17): 6003–6020.

Bett et al. (1993). "Packaging Capacity and Stability of Human Adenovirus Type 5 Vectors," *J. Virol.* 67(10): 5911–5921.

Bett et al. (1994) "An efficient and Flexible System for Construction of Adenovirus Vectors with insertions or Deletions in Early Regions 1 and 3," *Proc. Nail. A cad. Sci. USA* 91: 8802–8806.

Bridge et al. (1989). "Redundant Control of Adenovirus Late Gene Expression by Early Region 4," *J. Virol.* 63(2): 631–638.

Bunn et al. (1996). "Oxygen Sensing and Molecular Adaptation to Hypoxia," *Physiol. Rev.* 76(3): 839–885.

Cannio et al. (1991). "A Cell–Type Specific and Enhancer–Dependent Silencer in the Regulation of the Expression of the Human Urokinase Plasminogen Activator Gene," *Nuc. Acids Res.* 19(9): 2303–2308.

Coiditz. (1993). "Epidemiology of Breast Cancer," *Cancer Suppl.* 71(4): 1480–1489.

Dachs et al. (1996). "The Molecular Response of Mammalian Cells to Hypoxia and the Potential for Exploitation in Cancer Therapy," *Br. J. Cancer* 74: 5 126–5132.

Dachs et al. (1997). "Targeting Gene Expression to Hypoxic Tumor Cells," *Nat. Med.* 3(5): 515–520.

Feigner et al. (1989). "Cationic Liposome–Mediated Transfection," *Nature* 337: 387–388.

Firth et al. (1994). "Oxygen–Related Control Elements in the Phosphoglycerate Kinase 1 and Lactate Dehydrogenase A Genes: Similarities with the Erythropoietin 3' Enhancer," *Proc. Nati. Acad. Sci. USA* 91: 6496–6500.

Flint. (1982). "Expression of Adenoviral Genetic Information in Productively infected Cells," *Biochem. Biophys. Acta* 651: 175–208.

Flint. (1986). "Regulation of Adenovirus mRNA Formation," *Adv. Vir. Res.* 31: 169–228.

Folkman. (1989). "What is the Evidence that Tumors are Angiogenesis Dependent?" *Natl. Cancer Inst.* 82(1): 4–6.

Frankel et al. (1989). "Selection and Characterization of Ricin Toxin A–Chain Mutations in *Saccharomyces cerevisiae,*" *Mol. Cell. Biol.* 9(2): 4 15–420.

Graham. (1984). "Covalently Closed Circles of Human Adenovirus DNA are Infectious," *EMBO J.* 3(12): 2917–2922.

Grand. (1987). "The Structure and Functions of the Adenovirus Early Region 1 Proteins," *Biochern. J.* 241: 25–38.

Grooteclaes et al. (1984). "The 6–Kilobase c–erbB2 Promoter Contains Positive and Negative Regulatory Elements Functional in Human Mammary Cell Lines," *Cancer Res.* 54: 4193–4199.

Guillemin et al. (1997). "The Hypoxie Response: Huffing and HIFing," *Cell* 89: 9–12.

Hallahan et al. (1995). "Spatial and Temporal Control of Gene Therapy Using Ionizing Radiation," *Nat. Med* 1(8): 786–791.

Höckel et al. (1996). "Hypoxia and Radiation Response in Human Tumors," *Semin. Rad. Oncol.~*6(1): 3–9.

Hudson Ct al. (1990). "Structure and Inducible Regulation of the Human c–crb B2Ineu Promoter," *J. Biol. Chem.* 265: 4389–4393.

Ido et al. (1995). "Gene Therapy for 1–lepatoma Cells Using a Retrovirus Vector Carrying Herpes Simplex Virus Thymidine Kinase Gene Under the Control of Human ci–Fetoprotein Gene Promoter," *Cancer Res.* 55: 3105–3109.

Ishii et al. (1987) "Characterization of the Promoter Region of the Human C–erb B–2 Protooncogene," *Proc. Nati. Acad. Sci. USA* 84: 4374–4378.

Jiang et al. (1997). "V–SRC Induces Expression of Hypoxia–inducible Factor 1(HIF–1) and Transcription of Genes Encoding Vascular Endothelial Growth Factor and Enolase 1: Involvement of HIF–1 in Tumor Progression," *Can. Res.* 57: 5328–5335.

Johnson et al. (1994). "Autoregulatory Control of E2FJ Expression in Response to Positive and Negative Regulators of Cell Cycle Progression," *Genes Dev.* 8:1514–1525.

Kallinowksi. (1996). "The Role of Tumor Hypoxia for the Development of Future Treatment Concepts for Locally Advanced Cancer," *Cancer J.* 9(1): 37–40.

Kovarik et al. (1993) "Analysis of the Tissue–specific Promoter of the MUC1 Gene." *J. Biol. Chem.* 268(13): 9917–9926.

Kovarik et al. (1996). "Two GC Boxes (Sp1 Sites) are Involved in Regulation of the Activity of the Epithelium–Specific MUC1 Promoter," *Biol. Chem.* 271: 18140–18147.

Lamb et al. (1985). "Nucleotide Sequence of Cloned eDNA Coding for Preproricin," *Eur. J. Biochem.* 148: 265–270.

Lundwall. (1989). "Characterization of the Gene for Prostate–Specific Antigen, A Human Glandular Kalleikrein," *Biochem. Biophys. Res. Comm.* 161(3): 1151–1159.

Lundwall et al. (1987). "Moleular Cloning of Human Prostate Specific Antigen eDNA," *FEBS Lett.* 214(2):3 17–322.

Marchant. (1994). "Contemporary Management of Breast Disease II: Breast Cancer," *Obst. Gyn. Clin. N. America* 21(4):555–560.

Maxwell et al. (1987). "Cloning, Sequence Determination, and Expression in Transfected Cells of the Coding Sequence for the tox 176 Attenuated Diphtheria Toxin A Chain," *Mol. Cell. Biol.* 7(4): 1576–1579.

McKinnon et al. (1982). "Tn5 Mutagenesis of the Transforming Genes of Human Adenovirus Type 5," *Gene* 19:33–42.

Messing et al. (1992). "$P_0$ Promoter Directs Expression of Reporter and Toxin Genes to Schwann Cells of Transgenic Mice," *Nueron* 8:507–520.

Morimoto et al. eds. (1990). *Stress Prgteins in Biology and Medicine.* Cold Spring Harbor Laboratory Press. (Table of Contents Only).

Nevins. (1989). "Mechanisms of Viral–Mediated Trans–Activation of Transcription," *Adv. Virus. Res.* 37:35–83.

Palmiter et al. (1987). "Cell Lineage Ablation in Transgenic Mice by Cell–Specific Expression of a Toxin Gene," *Cell* 50:435–443.

Perisic et al. (1989). "Stable Binding of Drosophila Heat Shock Factor Head–to–Head and Tail–to–Tail Repeats of a Conserved 5 bp Recognition Unit," *Cell* 59:797–806.

Piatak et al. (1988). "Expression of Soluble and Fully Functional Ricin A Chain in *Escherichia coli* is Temperanfre–Sensitive," *J. Biol. Chem.* 263(10):4837–4843.

Riccio et al. (1985). "The Human Urokinase–Plasminogen Activator Gene and Its Promoter," *Nucleic Acids Res.* 13(8):2759–2771.

Riegman et al. (1991). "The Promoter of the Prostate–Specific Antigen Gene Contains a Functional Androgen Responsive Element," *Molec. Endocrin.* 5(12): 1921–1930..

Rinsch et al. (1997). "A Gene Therapy Approach to Regulated Delivery of Erythropoietin as a Function of Oxygen Tension," *Hum. Gene Ther.* 8(16):1881–1889.

Rodriguez et al. (1997). "Prostate Attenuated Replication Competent Adenovirus (ARCA) CN706: A Selective Cytotoxic for Prostate–Specific Antigen–Positive Prostate Cancer Cells," *Cancer Research* 57:2559–2563.

Sebrewe et al. (1990). "Cloning of the Complete Gene for Carcinoembryonic Antigen: Analysis of its Promoter Indicates a Region Conveying Cell Type–Specific Expression," *Mol. Cell. Biol.* 10(6):2738–2748.

Schurr et al. (1996). "Prostate–Specific Antigen Expression is Regulated by an Upstream Enhancer," *J. Biol. Chem.* 271(12):7043–7051.

Scott et al. (1994). "Binding of an ETS–related Protein within the DNase I Hypersensitive Site of the HER2/neu Promoter in Human Breast Cancer Cells," *Biol. Chem.* 269(31): 19848–19858.

Semenza et al. (1996). "Hypoxia Response Elements in the Adolase A, Enolase 1, and Lactate Dehydrogenase A Gene Promoters Contain Essential Binding Sites for Hypoxia–Inducible Factor 1 ," *J. Biol. Chem.* 271(51):32529–32537.

Swaminathan et al. (1995). "Regulation of Adenovirus E2 Transcription Unit," *Curr. Topics in Micro. and Imm.* 199 (part 3): 77–194.

Tal et al. (1987). "Human HER2(neu) Promoter: Evidence for Multiple Mechanisms for Transcriptional Initiation," *Mol. Cell. Biol.* 7(7):2597–2601.

Tollefson et al. (1996). "The Adenovirus Death Protein (E3–11.6K) is Required at Very Late Stages of Infection for Efficient Cell Lysis and Release of Adenovirus from Infected Cells," *J. Virol.* 70(4):2296–2306.

Tollefson et al. (1992). "The 11,600–$M_w$ Protein Encoded by Region E3 of Adenovirus Is Expressed Early but is Greatly Amplified at Late Stages of Infection," *J. Virol.* 66(6):3633–3642.

Tsai–Morris et al. (1988). "5' Flanking Sequence and Genomic Structure of Egr–1, A Murine Mitogen Inducible Zinc Finger Encoding Gene," *Nuc. Acids Res.* 16(18):8835–8846.

Virtanen et al. (1984). "mRNAs from Human Adenovirus 2 Early Region 4," *J Virol.* 51(3): 822–831.

Watanabe et al. (1987). "Cell–Specific Enhancer Activity in a Far Upstream Region of the Human α–Fetoprotein Gene," *J. Biol. Chem.* 262:4812–4818.

Weinberg et al. (1983). "A Cell Line That Supports the Growth Of A Defective Early Region 4 Deletion Mutant of Human Adenovirus Type 2,". *Proc. Nati. Acad. Sci.* 80:5383–5386.

Zwicker et al. (1995). "Cell Cycle Regulation of the Cyclin A, CDC25C and CDC2 Genes is Based on a Comman Mechanism of Transcriptional Repression," *EMBO J.* 14(18):45 14–4522.

* cited by examiner

```
ggcccaaaa  ttagcaagtg  accacgtgt  tctgaagcca  gtggcctaag  gaccacctt   61
gcagaaccgt  ggtctccttg  tcacagtcta  ggcagcctct  ggcttagcct  ctgttctt   121
cataacctt   ctcagcgcct  gctctgggcc  agaccagtgt  tgggaggagt  cgctactgag  181
ctcctagatt  ggcagggag   gcagatggag  aaaaggagtg  tgtgtggtca  gcattggagc  241
agaggcagca  gtgggcaata  gaggaagtga  gtaaatcctt  gggagggctc  cctagaagtg  301
atgtgtttc   ttttttgtt   ttagagacag  gatctcgctc  tgtcgcccag  gctggtgtgc  361
agtggcatga  tcatagctca  ctgcagcctc  gacttctcgg  gctcaagcaa  tcctcccacc  421
tcagcctccc  aagtagctgg  gactacgggc  acacgccacc  atgcctggct  aattttgta   481
tttttgtag   agatgggtct  tcaccatgtt  gatcaggctg  gtctcgaact  cctggctca   541
tgcgatccac  cccgccagct  gattacaggg  attccggtgg  tgagcaccg   cgcccagacg  601
ccacttcatc  gtattgtaaa  cgtctgttac  ccctgtcttc  cctgtctac   tggactgtga  661
gctccttagg  gccacgaatt  gaggatgggg  cacagagcaa  gctctccaaa  cgtttgttga  721
atgagtgagg  gaatgaatga  gttcaagcag  atgctatacg  ttggctgttg  gagattttgg  781
ctaaaatggg  acttgcagga  aagcccgacg  tcccctcgc   cattccagg   caccgctctt  841
cagcttgggc  tctgggtgag  cgggataggg  ctgggtgcag  gattaggata  atgtcatggg  901
tgaggcaagt  tgaggatgga  agaggtggct  gatggctggg  ctgtggaact  gatgatcctg  961
aaaagaagag  gggacagtct  ctggaaatct  aagctgaggc  tgttgggggc  tacaggttga  1021
gggtcacgtg  cagaagagag  gctctgttct  gaacctgcac  tatagaaagg  tcagtgggat  1081
gcgggagcgt  cggggcgggg  cgggccctat  gttcccgtgt  ccccacgcct  ccagcagggg  1141
acgcccgggc  tggggcggg   gagtcagacc  gcgcctggta  ccatccggac  aaagcctgcg  1201
cgccgccccgc ccccgccattg gccgtaccgc cccgccgcgc cgcccatcc   cgcccctcgc   1261
cgccggtcc   ggcgcgttaa  agccaatagg  aaccgccgc   gttgttcccg  tcacggccgg  1321
ggcagccaat  tgtgcggcg   ctcggcggct  cgtggctctt  tcgcggcaaa  aaggatttgg  1381
cgcgtaaaag*tggccgggac  tttgcaggca  gcggccgcg   gggcgggagc  gggatcgagc  1441
cctcgcgag   gcctgccgcc  atgggcccgc  gccgccgcg   ccgcctgtca  cccgggccgc  1501
gcgggccgtg  agcgtcatg
```

FIG.2

```
aagcttctag ttttcttttc ccggtgacat cgtggaaagc actagcatct ctaagcaatg 60
atctgtgaca atattcacag tgtaatgcca tccagggaac tcaactgagc cttgatgtcc 120
agagattttt gtgttttttt ctgagactga gtctcgctct gtgccaggct ggagtgcagt 180
ggtgcaacct tggctcactg caagctccgc ctcctgggtt cacgccattc tcctgcctca 240
gcctcctgag tagctgggac tacaggcacc cgccaccacg cctggctaat tttttgtat 300
ttttagtaga gatgggttt cactgtgtta gccaggatgg tctcagtctc ctgacctcgt 360
gatctgccca ccttggcctc ccaaagtgct gggatgacag gcgtgagcca ccgcgcctgg 420
ccgatatcca gagattttt gggggctcc atcacacaga catgttgact gtcttcatgg 480
ttgacttta gtatccagcc cctctagaaa tctagctgat atagtgtggc tcaaaacctt 540
cagcacaaat cacaccgtta gactatctgg tgtgcccaa accttcaggt gaacaaggg 600
actctaatct ggcaggatat tccaaagcat tagagatgac ctcttgcaaa gaaaaagaaa 660
tggaaaagaa aaagaaagaa aggaaaaaaa aaaaaaaaa gagatgacct ctcaggctct 720
gaggggaaac gcctgaggtc tttgagcaag gtcagtcctc tgttgcacag tctccctcac 780
agggtcattg tgacgatcaa atgtggtcac gtgtatgagg caccagcaca tgcctggctc 840
tggggagtgc cgtgtaagtg tatgcttgca ctgctgaatg cttgggatgt gtcaggatt 900
atcttcagca cttacagatg ctcatctcat cctcacagca tcactatggg atgggtatta 960
ctggcctcat tgatggaga aagtggctgt ggctcagaaa gggggacca ctagaccagg 1020
gacactctgg atgctgggga ctccagagac catgaccact caccaactgc agagaaatta 1080
attgtggcct gatgtccctg tcctggagag ggtggaggtg gaccttcact aacctcctac 1140
cttgaccctc tcttttaggg ctctttctga cctccaccat ggtactagga ccccattgta 1200
ttctgtaccc tcttgactct atgaccccca ctgcccactg catccagctg ggtcccctcc 1260
tatctctatt cccagctggc cagtgcagtc tcagtgccca cctgtttgtc agtaactctg 1320
aaggggctga catttactg acttgcaaac aaataagcta actttccaga gttttgtgaa 1380
tgctggcaga gtccatgaga ctcctgagtc agaggcaaag gcttttactg ctcacagctt 1440
agcagacagc atgaggttca tgttcacatt agtacacctt gccccccca aatcttgtag 1500
ggtgaccaga gcagtctagg tggatgctgt gcagaagggg tttgtgccac tggtgagaaa 1560
cctgagatta ggaatcctca atcttatact gggacaactt gcaaacctgc tcagcctttg 1620
tctctgatga agatattatc ttcatgatct tggattgaaa acagacctac tctggaggaa 1680
```

FIG.3A

```
catattgtat cgattgtcct tgacagtaaa caaatctgtt gtaagagaca ttatctttat 1740
tatctaggac agtaagcaag cctggatctg agagagatat catcttgcaa ggatgcctgc 1800
tttacaaaca tccttgaaac aacaatccag aaaaaaaaag gtgttgctgt ctttgctcag 1860
aagacacaca gatacgtgac agaaccatgg agaattgcct cccaacgctg ttcagccaga 1920
gccttccacc cttgtctgca ggacagtctc aacgttccac cattaaatac ttcttctatc 1980
acatcctgct tctttatgcc taaccaaggt tctaggtccc gatcgactgt gtctggcagc 2040
actccactgc caaacccaga ataaggcagc gctcaggatc ccgaaggggc atggctgggg 2100
atcagaactt ctgggtttga gtgaggagtg ggtccaccct cttgaatttc aaaggaggaa 2160
gaggctggat gtgaaggtac tgggggaggg aaagtgtcag ttccgaactc ttaggtcaat 2220
gagggaggag actggtaagg tcccagctcc cgaggtactg atgtgggaat ggcctaagaa 2280
tctcatatcc tcaggaagaa ggtgctggaa tcctgagggg tagagttctg ggtatatttg 2340
tggcttaagg ctctttggcc cctgaaggca gaggctggaa ccattaggtc cagggtttgg 2400
ggtgatagta atgggatctc ttgattcctc aagagtctga ggatcgaggg ttgcccattc 2460
ttccatcttg ccacctaatc cttactccac ttgagggtat caccagccct tctagctcca 2520
tgaaggtccc ctgggcaagc acaatctgag catgaaagat gccccagagg ccttgggtgt 2580
catccactca tcatccagca tcacactctg agggtgtggc cagcaccatg acgtcatgtt 2640
gctgtgacta tccctgcagc gtgcctctcc agccacctgc caaccgtaga gctgcccatc 2700
ctcctctggt gggagtggcc tgcatggtgc caggctgagg cctagtgtca gacagggagc 2760
ctggaatcat agggatccag gactcaaaag tgctagagaa tggccatatg tcaccatcca 2820
tgaaatctca agggcttctg ggtggagggc acagggacct gaacttatgg tttcccaagt 2880
ctattgctct cccaagtgag tctcccagat acgaggcact gtgccagcat cagccttatc 2940
tccaccacat cttgtaaaag gactacccag ggccctgatg aacaccatgg tgtgtacagg 3000
agtaggggt ggaggcacgg actcctgtga ggtcacagcc aagggagcat catcatgggt 3060
ggggaggagg caatggacag gcttgagaac ggggatgtgg ttgtatttgg ttttctttgg 3120
ttagataaag tgctgggtat aggattgaga gtggagtatg aagaccagtt aggatggagg 3180
atcagattgg agttgggtta gataaagtgc tgggtatagg attgagagtg gagtatgaag 3240
accagttagg atggaggatc agattggagt tgggttagag atgggtaaa attgtgctcc 3300
ggatgagttt gggattgaca ctgtggaggt ggtttgggat ggcatggctt tgggatggaa 3360
```

FIG.3B

```
atagatttgt tttgatgttg gctcagacat ccttggggat tgaactgggg atgaagctgg 3420
gtttgatttt ggaggtagaa gacgtggaag tagctgtcag atttgacagt ggccatgagt 3480
tttgtttgat ggggaatcaa acaatggggg aagacataag ggttggcttg ttaggttaag 3540
ttgcgttggg ttgatggggt cggggctgtg tataatgcag ttggattggt ttgtattaaa 3600
ttgggttggg tcaggttttg gttgaggatg agttgaggat atgcttgggg acaccggatc 3660
catgaggttc tcactggagt ggagacaaac ttcctttcca ggatgaatcc agggaagcct 3720
taattcacgt gtagggagg tcaggccact ggctaagtat atccttccac tccagctcta 3780
agatggtctt aaattgtgat tatctatatc cacttctgtc tccctcactg tgcttggagt 3840
ttacctgatc actcaactag aaacagggga agatttatc aaattctttt ttttttttt 3900
ttttttttga gacagagtct cactctgttg cccaggctgg agtgcagtgg cgcagtctcg 3960
gctcactgca acctctgcct cccaggttca agtgattctc ctgcctcagc ctcctgagtt 4020
gctgggatta caggcatgca gcaccatgcc cagctaattt ttgtattttt agtagagatg 4080
gggtttcacc aatgtttgcc aggctggcct cgaactcctg acctggtgat ccacctgcct 4140
cagcctccca aagtgctggg attacaggcg tcagccaccg cgcccagcca cttttgtcaa 4200
attcttgaga cacagctcgg gctggatcaa gtgagctact ctggttttat tgaacagctg 4260
aaataaccaa cttttggaa attgatgaaa tcttacggag ttaacagtgg aggtaccagg 4320
gctcttaaga gttcccgatt ctcttctgag actacaaatt gtgatttgc atgccacctt 4380
aatcttttt tttttttttt taaatcgagg tttcagtctc attctatttc ccaggctgga 4440
gttcaatagc gtgatcacag ctcactgtag ccttgaactc ctggccttaa gagattctcc 4500
tgcttcggtc tcccaatagc taagactaca gtagtccacc accatatcca gataattttt 4560
aaattttttg gggggccggg cacagtggct cacgcctgta atcccaacac catgggaggc 4620
tgagatgggt ggatcacgag gtcaggagtt tgagaccagc ctgaccaaca tggtgaaact 4680
ctgtctctac taaaaaaaaa aaaatagaa aaattagccg ggcgtggtgg cacacggcac 4740
ctgtaatccc agctactgag gaggctgagg caggagaatc acttgaaccc agaaggcaga 4800
ggttgcaatg agccgagatt gcgccactgc actccagcct gggtgacaga gtgagactct 4860
gtctcaaaaa aaaaaaattt tttttttttt tttgtagaga tggatcttgc tttgtttctc 4920
tggttggcct tgaactcctg gcttcaagtg atcctcctac cttggcctcg gaaagtgttg 4980
ggattacagg cgtgagccac catgactgac ctgtcgttaa tcttgaggta cataaacctg 5040
gctcctaaag gctaaaggct aaatatttgt tggagaaggg gcattggatt ttgcatgagg 5100
```

FIG.3C

```
atgattctga cctgggaggg caggtcagca ggcatctctg ttgcacagat agagtgtaca 5160
ggtctggaga acaaggagtg gggggttatt ggaattccac attgtttgct gcacgttgga 5220
ttttgaaatg ctagggaact ttgggagact catatttctg ggctagagga tctgtggacc 5280
acaagatctt tttatgatga cagtagcaat gtatctgtgg agctggattc tgggttggga 5340
gtgcaaggaa aagaatgtac taaatgccaa gacatctatt tcaggagcat gaggaataaa 5400
agttctagtt tctggtctca gagtggtgca gggatcaggg agtctcacaa tctcctgagt 5460
gctggtgtct tagggcacac tgggtcttgg agtgcaaagg atctaggcac gtgaggcttt 5520
gtatgaagaa tcggggatcg tacccacccc ctgtttctgt ttcatcctgg gcatgtctcc 5580
tctgcctttg tccctagat gaagtctcca tgagctacaa gggcctggtg catccagggt 5640
gatctagtaa ttgcagaaca gcaagtgcta gctctccctc cccttccaca gctctgggtg 5700
tgggaggggg ttgtccagcc tccagcagca tggggagggc cttggtcagc ctctgggtgc 5760
cagcagggca ggggcggagt cctggggaat gaaggtttta tagggctcct gggggaggct 5820
ccccagcccc aagctt                                                5836
```

FIG.3D

```
aagcttttta gtgctttaga cagtgagctg gtctgtctaa cccaagtgac ctgggctcca    60
tactcagccc cagaagtgaa gggtgaagct gggtggagcc aaaccaggca agcctaccct   120
cagggctccc agtggcctga gaaccattgg acccaggacc cattacttct agggtaagga   180
aggtacaaac accagatcca accatggtct gggggacag ctgtcaaatg cctaaaaata    240
tacctgggag aggagcaggc aaactatcac tgccccaggt tctctgaaca gaaacagagg   300
ggcaacccaa agtccaaatc caggtgagca ggtgcaccaa atgcccagag atatgacgag   360
gcaagaagtg aaggaaccac ccctgcatca aatgttttgc atgggaagga gaaggggtt    420
gctcatgttc ccaatccagg agaatgcatt tgggatctgc cttcttctca ctccttggtt   480
agcaagacta agcaaccagg actctggatt tggggaaaga cgtttatttg tggaggccag   540
tgatgacaat cccacgaggg cctaggtgaa gagggcagga aggctcgaga cactggggac   600
tgagtgaaaa ccacacccat gatctgcacc acccatggat gctccttcat tgctcacctt   660
tctgttgata tcagatggcc ccatttctg taccttcaca gaaggacaca ggctagggtc    720
tgtgcatggc cttcatcccc ggggccatgt gaggacagca ggtgggaaag atcatgggtc   780
ctcctgggtc ctgcagggcc agaacattca tcacccatac tgacctccta gatgggaatg   840
gcttccctgg ggctgggcca acggggcctg ggcaggggag aaaggacgtc aggggacagg   900
gaggaagggt catcgagacc cagcctggaa ggttcttgtc tctgaccatc caggatttac   960
ttccctgcat ctacctttgg tcatttttcc tcagcaatga ccagctctgc ttcctgatct  1020
cagcctccca ccctggacac agcacccag tccctggccc ggctgcatcc acccaatacc   1080
ctgataaccc aggacccatt acttctaggg taaggagggt ccaggagaca gaagctgagg  1140
aaaggtctga agaagtcaca tctgtcctgg ccagagggga aaaccatca gatgctgaac   1200
caggagaatg ttgacccagg aaagggaccg aggacccaag aaaggagtca gaccaccagg  1260
gtttgcctga gaggaaggat caaggccccg agggaaagca gggctggctg catgtgcagg  1320
acactggtgg ggcatatgtg tcttagattc tccctgaatt cagtgtccct gccatggcca  1380
gactctctac tcaggcctgg acatgctgaa ataggacaat ggccttgtcc tctctcccca  1440
ccatttggca agagacataa aggacattcc aggacatgcc ttcctgggag gtccaggttc  1500
tctgtctcac acctcaggga ctgtagttac tgcatcagcc atggtaggtg ctgatctcac  1560
ccagcctgtc caggcccttc cactctccac tttgtgacca tgtccaggac caccctcag   1620
atcctgagcc tgcaaatacc cccttgctgg gtgggtggat tcagtaaaca gtgagctcct  1680
```

FIG.4A

```
atccagcccc cagagccacc tctgtcacct tcctgctggg catcatccca ccttcacaag    1740
cactaaagag catggggaga cctggctagc tgggtttctg catcacaaag aaaataatcc    1800
cccaggttcg gattcccagg gctctgtatg tggagctgac agacctgagg ccaggagata    1860
gcagaggtca gccctaggga gggtgggtca tccacccagg ggacagggt gcaccagcct    1920
tgctactgaa agggcctccc caggacagcg ccatcagccc tgcctgagag ctttgctaaa    1980
cagcagtcag aggaggccat ggcagtggct gagctcctgc tccaggcccc aacagaccag    2040
accaacagca caatgcagtc cttccccaac gtcacaggtc accaaaggga aactgaggtg    2100
ctacctaacc ttagagccat caggggagat aacagcccaa tttcccaaac aggccagttt    2160
caatcccatg acaatgacct ctctgctctc attcttccca aaataggacg ctgattctcc    2220
cccaccatgg atttctccct tgtcccggga gccttttctg ccccctatga tctgggcact    2280
cctgacacac acctcctctc tggtgacata tcagggtccc tcactgtcaa gcagtccaga    2340
aaggacagaa ccttggacag cgcccatctc agcttcaccc ttcctccttc acagggttca    2400
gggcaaagaa taaatggcag aggccagtga gcccagagat ggtgacaggc agtgacccag    2460
gggcagatgc ctggagcagg agctggcggg gccacaggga gaaggtgatg caggaaggga    2520
aacccagaaa tgggcaggaa aggaggacac aggctctgtg gggctgcagc ccagggttgg    2580
actatgagtg tgaagccatc tcagcaagta aggccaggtc ccatgaacaa gagtgggagc    2640
acgtggcttc ctgctctgta tatggggtgg gggattccat gccccataga accagatggc    2700
cggggttcag atggagaagg agcaggacag gggatcccca ggataggagg acccagtgt     2760
ccccacccag gcaggtgact gatgaatggg catgcagggt cctcctgggc tgggctctcc    2820
ctttgtccct caggattcct tgaaggaaca tccggaagcc gaccacatct acctggtggg    2880
ttctggggag tccatgtaaa gccaggagct tgtgttgcta ggaggggtca tggcatgtgc    2940
tggggcacc aaagagagaa acctgagggc aggcaggacc tggtctgagg aggcatggga     3000
gcccagatgg ggagatggat gtcaggaaag gctgccccat cagggagggt gatagcaatg    3060
ggggtctgt gggagtgggc acgtgggatt ccctgggctc tgccaagttc cctcccatag     3120
tcacaacctg gggacactgc ccatgaaggg gcgcctttgc ccagccagat gctgctggtt    3180
ctgcccatcc actaccctct ctgctccagc cactctgggt ctttctccag atgccctgga    3240
cagccctggc ctgggcctgt cccctgagag gtgttgggag aagctgagtc tctggggaca    3300
ctctcatcag agtctgaaag gcacatcagg aaacatccct ggtctccagg actaggcaat    3360
```

FIG.4B

```
gaggaaaggg ccccagctcc tcccttttgcc actgagaggg tcgaccctgg gtggccacag    3420
tgacttctgc gtctgtccca gtcaccctga aaccacaaca aaacccagc cccagaccct      3480
gcaggtacaa tacatgtggg gacagtctgt acccagggga agccagttct ctcttcctag    3540
gagaccgggc ctcagggctg tgcccggggc aggcggggc agcacgtgcc tgtccttgag     3600
aactcgggac cttaagggtc tctgctctgt gaggcacagc aaggatcctt ctgtccagag    3660
atgaaagcag ctcctgcccc tcctctgacc tcttcctcct tcccaaatct caaccaacaa    3720
ataggtgttt caaatctcat catcaaatct tcatccatcc acatgagaaa gcttaaaacc    3780
caatggattg acaacatcaa gagttggaac aagtggacat ggagatgtta cttgtggaaa    3840
tttagatgtg ttcagctatc gggcaggaga atctgtgtca aattccagca tggttcagaa    3900
gaatcaaaaa gtgtcacagt ccaaatgtgc aacagtgcag gggataaaac tgtggtgcat    3960
tcaaactgag ggatattttg gaacatgaga aaggaaggga ttgctgctgc acagaacatg    4020
gatgatctca cacatagagt tgaaagaaag gagtcaatcg cagaatagaa aatgatcact    4080
aattccacct ctataaagtt tccaagagga aaacccaatt ctgctgctag agatcagaat    4140
ggaggtgacc tgtgccttgc aatggctgtg agggtcacgg gagtgtcact tagtgcaggc    4200
aatgtgccgt atcttaatct gggcagggct ttcatgagca cataggaatg cagacattac    4260
tgctgtgttc attttacttc accggaaaag aagaataaaa tcagccgggc gcggtggctc    4320
acgcctgtaa tcccagcact ttagaaggct gaggtgggca gattacttga ggtcaggagt    4380
tcaagaccac cctggccaat atggtgaaac cccggctcta ctaaaaatac aaaaattagc    4440
tgggcatggt ggtgcgcgcc tgtaatccca gctactcggg aggctgaggc tggacaattg    4500
cttggaccca ggaagcagag gttgcagtga gccaagattg tgccactgca ctccagcttg    4560
ggcaacagag ccagactctg taaaaaaaaa aaaaaaaaa aaaaaagaa agaaagaaaa      4620
agaaagaaa gtataaaatc tctttgggtt aacaaaaaaa gatccacaaa acaaacacca    4680
gctcttatca aacttacaca actctgccag agaacaggaa acacaaatac tcattaactc    4740
actttgtgg caataaaacc ttcatgtcaa aaggagacca ggacacaatg aggaagtaaa    4800
actgcaggcc ctacttgggt gcagagaggg aaaatccaca aataaaacat taccagaagg    4860
agctaagatt tactgcattg agttcattcc ccaggtatgc aaggtgattt taacacctga    4920
aaatcaatca ttgcctttac tacatagaca gattagctag aaaaaaatta caactagcag    4980
aacagaagca atttggccctt cctaaaattc cacatcatat catcatgatg gagacagtgc    5040
agacgccaat gacaataaaa agagggacct ccgtcacccg gtaaacatgt ccacacagct    5100
```

FIG.4C

```
ccagcaagca cccgtcttcc cagtgaatca ctgtaacctc ccctttaatc agccccaggc   5160
aaggctgcct gcgatggcca cacaggctcc aacccgtggg cctcaacctc ccgcagaggc   5220
tctcctttgg ccacccatg gggagagcat gaggacaggg cagagccctc tgatgcccac    5280
acatggcagg agctgacgcc agagccatgg gggctggaga gcagagctgc tggggtcaga   5340
gcttcctgag gacacccagg cctaagggaa ggcagctccc tggatggggg caaccaggct   5400
ccgggctcca acctcagagc ccgcatggga ggagccagca ctctaggcct ttcctagggt   5460
gactctgagg ggaccctgac acgacaggat cgctgaatgc acccgagatg aaggggccac   5520
cacgggaccc tgctctcgtg gcagatcagg agagagtggg acaccatgcc aggcccccat   5580
ggcatggctg cgactgaccc aggccactcc cctgcatgca tcagcctcgg taagtcacat   5640
gaccaagccc aggaccaatg tggaaggaag gaaacagcat cccctttagt gatggaaccc   5700
aaggtcagtg caaagagagg ccatgagcag ttaggaaggg tggtccaacc tacagcacaa   5760
accatcatct atcataagta gaagccctgc tccatgaccc ctgcatttaa ataaacgttt   5820
gttaaatgag tcaaattccc tcaccatgag agctcacctg tgtgtaggcc catcacacac   5880
acaaacacac acacacacac acacacacac acacacacac acagggaaag tgcaggatcc   5940
tggacagcac caggcaggct tcacaggcag agcaaacagc gtgaatgacc catgcagtgc   6000
cctgggcccc atcagctcag agaccctgtg agggctgaga tggggctagg cagggagag    6060
acttagagag ggtgggggcct ccagggaggg ggctgcaggg agctgggtac tgccctccag  6120
ggagggggct gcagggagct gggtactgcc ctccagggag ggggctgcag ggagctgggt   6180
actgccctcc agggaggggg ctgcagggag ctgggtactg ccctccaggg aggggctgc    6240
agggagctgg gtactgccct ccagggaggc aggagcactg ttcccaacag agagcacatc   6300
ttcctgcagc agctgcacag acacaggagc ccccatgact gccctgggcc agggtgtgga   6360
ttccaaattt cgtgccccat tgggtgggac ggaggttgac cgtgacatcc aagggcatc    6420
tgtgattcca aacttaaact actgtgccta caaaatagga aataacccta cttttctac    6480
tatctcaaat tccctaagca caagctagca ccctttaaat caggaagttc agtcactcct   6540
ggggtcctcc catgccccca gtctgacttg caggtgcaca gggtggctga catctgtcct   6600
tgctcctcct cttggctcaa ctgccgcccc tctgggggt gactgatggt caggacaagg    6660
gatcctagag ctggccccat gattgacagg aagcaggac ttggcctcca ttctgaagac    6720
tagggtgtc aagagagctg ggcatcccac agagctgcac aagatgacgc ggacagaggg    6780
```

FIG.4D

```
tgacacaggg ctcagggctt cagacgggtc gggaggctca gctgagagtt cagggacaga    6840
cctgaggagc ctcagtggga aaagaagcac tgaagtggga agttctggaa tgttctggac    6900
aagcctgagt gctctaagga aatgctccca ccccgatgta gcctgcagca ctggacggtc    6960
tgtgtacctc cccgctgccc atcctctcac agccccgcc tctagggaca caactcctgc    7020
cctaacatgc atctttcctg tctcattcca cacaaaggg cctctgggt ccctgttctg      7080
cattgcaagg agtggaggtc acgttcccac agaccaccca gcaacaggg cctatggagg    7140
tgcggtcagg aggatcacac gtcccccat gcccagggga ctgactctgg gggtgatgga    7200
ttggcctgga ggccactggt ccgctctgtc cctgaggga atctgcaccc tggaggctgc    7260
cacatccctc ctgattcttt cagctgaggg cccttcttga atcccaggg aggactcaac    7320
ccccactggg aaaggcccag tgtggacggt tccacagcag cccagctaag gcccttggac    7380
acagatcctg agtgagagaa cctttaggga cacaggtgca cggccatgtc cccagtgccc    7440
acacagagca ggggcatctg gaccctgagt gtgtagctcc cgcgactgaa cccagccctt    7500
ccccaatgac gtgacccctg gggtggctcc aggtctccag tccatgccac caaaatctcc    7560
agattgaggg tcctccctty agtccctgat gcctgtccag gagctgcccc ctgagcaaat    7620
ctagagtgca gagggctggg attgtggcag taaaagcagc cacatttgtc tcaggaagga    7680
aagggaggac atgagctcca ggaagggcga tggcgtcctc tagtgggcgc ctcctgttaa    7740
tgagcaaaaa ggggccagga gagttgagag atcagggctg gccttggact aaggctcaga    7800
tggagaggac tgaggtgcaa agaggggct gaagtagggg agtggtcggg agagatggga    7860
ggagcaggta aggggaagcc ccagggaggc cggggaggg tacagcagag ctctccactc    7920
ctcagcattg acatttgggg tggtcgtgct agtggggttc tgtaagttgt agggtgttca    7980
gcaccatctg gggactctac ccactaaatg ccagcaggac tccctcccca agctctaaca    8040
accaacaatg tctccagact ttccaaatgt cccctggaga gcaaaattgc ttctggcaga    8100
atcactgatc tacgtcagtc tctaaaagtg actcatcagc gaaatccttc acctcttggg    8160
agaagaatca caagtgtgag aggggtagaa actgcagact tcaaaatctt tccaaaagag    8220
ttttacttaa tcagcagttt gatgtcccag gagaagatac atttagagtg tttagagttg    8280
atgccacatg gctgcctgta cctcacagca ggagcagagt gggttttcca agggcctgta    8340
accacaactg gaatgacact cactgggtta cattacaaag tggaatgtgg ggaattctgt    8400
agactttggg aagggaaatg tatgacgtga gcccacagcc taaggcagtg gacagtccac    8460
tttgaggctc tcaccatcta ggagacatct cagccatgaa catagccaca tctgtcatta    8520
```

FIG.4E

```
gaaaacatgt tttattaaga ggaaaaatct aggctagaag tgctttatgc tcttttttct    8580
ctttatgttc aaattcatat acttttagat cattccttaa agaagaatct atcccoctaa    8640
gtaaatgtta tcactgactg gatagtgttg gtgtctcact cccaacccct gtgtggtgac    8700
agtgccctgc ttccccagcc ctgggccctc tctgattcct gagagctttg ggtgctcctt    8760
cattaggagg aagagaggaa gggtgttttt aatattctca ccattcaccc atccacctct    8820
tagacactgg gaagaatcag ttgcccactc ttggatttga tcctcgaatt aatgacctct    8880
atttctgtcc cttgtccatt tcaacaatgt gacaggccta agaggtgcct tctccatgtg    8940
attttgagg agaaggttct caagataagt tttctcacac ctctttgaat tacctccacc     9000
tgtgtcccca tcaccattac cagcagcatt tggaccctt ttctgttagt cagatgcttt     9060
ccacctcttg agggtgtata ctgtatgctc tctacacagg aatatgcaga ggaaatagaa    9120
aaagggaaat cgcattacta ttcagagaga agaagacctt tatgtgaatg aatgagagtc    9180
taaaatccta agagagccca tataaaatta ttaccagtgc taaaactaca aaagttacac    9240
taacagtaaa ctagaataat aaaacatgca tcacagttgc tggtaaagct aaatcagata    9300
tttttttctt agaaaaagca ttccatgtgt gttgcagtga tgacaggagt gcccttcagt    9360
caatatgctg cctgtaattt ttgttccctg gcagaatgta ttgtcttttc tccctttaaa    9420
tcttaaatgc aaaactaaag gcagctcctg ggcccctcc ccaaagtcag ctgcctgcaa     9480
ccagccccac gaagagcaga ggcctgagct tccctggtca aaatagggg ctagggagct     9540
taaccttgct cgataaagct gtgttcccag aatgtcgctc ctgttcccag gggcaccagc    9600
ctggagggtg gtgagcctca ctggtggcct gatgcttacc ttgtgccctc acaccagtgg    9660
tcactggaac cttgaacact tggctgtcgc ccggatctgc agatgtcaag aacttctgga    9720
agtcaaatta ctgcccactt ctccagggca gatacctgtg aacatccaaa accatgccac    9780
agaaccctgc ctggggtcta caacacatat ggactgtgag caccaagtcc agccctgaat    9840
ctgtgaccac ctgccaagat gcccctaact gggatccacc aatcactgca catggcaggc    9900
agcgaggctt ggaggtgctt cgccacaagg cagcccaat ttgctgggag tttcttggca     9960
cctggtagtg gtgaggagcc ttgggaccct caggattact ccccttaagc atagtgggga    10020
cccttctgca tccccagcag gtgccccgct cttcagagcc tctctctctg aggtttaccc    10080
agacccctgc accaatgaga ccatgctgaa gcctcagaga gagagatgga gctttgacca    10140
ggagccgctc ttccttgagg gccagggcag ggaaagcagg aggcagcacc aggagtggga    10200
```

FIG.4F

```
acaccagtgt ctaagccct gatgagaaca gggtggtctc tcccatatgc ccataccagg   10260
cctgtgaaca gaatcctcct tctgcagtga caatgtctga gaggacgaca tgtttcccag   10320
cctaacgtgc agccatgccc atctacccac tgcctactgc aggacagcac caacccagga   10380
gctgggaagc tgggagaaga catggaatac ccatggcttc tcaccttcct ccagtccagt   10440
gggcaccatt tatgcctagg acacccacct gccggcccca ggctcttaag agttaggtca   10500
cctaggtgcc tctgggaggc cgaggcagga gaattgcttg aacccgggag gcagaggttg   10560
cagtgagccg agatcacacc actgcactcc agcctgggtg acagaatgag actctgtctc   10620
aaaaaaaaag agaaagatag catcagtggc taccagggc tagggcagg ggaaggtgga   10680
gagttaatga ttaatagtat gaagtttcta tgtgagatga tgaaaatgtt ctggaaaaaa   10740
aaatatagtg gtgaggatgt agaatattgt gaatataatt aacggcattt aattgtacac   10800
ttaacatgat taatgtggca tatttatct tatgtatttg actacatcca agaaacactg   10860
ggagagggaa agcccaccat gtaaaataca cccaccctaa tcagatagtc ctcattgtac   10920
ccaggtacag gcccctcatg acctgcacag gaataactaa ggatttaagg acatgaggct   10980
tcccagccaa ctgcaggtgc acaacataaa tgtatctgca aacagactga gagtaaagct   11040
gggggcacaa acctcagcac tgccaggaca cacaccttc tcgtggattc tgactttatc   11100
tgacccggcc cactgtccag atcttgttgt gggattggga caagggaggt cataaagcct   11160
gtccccaggg cactctgtgt gagcacacga gacctcccca ccccccacc gttaggtctc   11220
cacacataga tctgaccatt aggcattgtg aggaggactc tagcgcgggc tcagggatca   11280
caccagagaa tcaggtacag agaggaagac ggggctcgag gagctgatgg atgacacaga   11340
gcagggttcc tgcagtccac aggtccagct caccctggtg taggtgcccc atccccctga   11400
tccaggcatc cctgacacag ctccctcccg gagcctcctc ccaggtgaca catcagggtc   11460
cctcactcaa gctgtccaga gagggcagca ccttggacag cgcccacccc acttcactct   11520
tcctccctca cagggctcag ggctcagggc tcaagtctca gaacaaatgg cagaggccag   11580
tgagcccaga gatggtgaca gggcaatgat ccaggggcag ctgcctgaaa cgggagcagg   11640
tgaagccaca gatgggagaa gatggttcag gaagaaaaat ccaggaatgg gcaggagagg   11700
agaggaggac acaggctctg tggggctgca gcccaggatg ggactaagtg tgaagacatc   11760
tcagcaggtg aggccaggtc ccatgaacag agaagcagct cccacctccc ctgatgcacg   11820
gacacacaga gtgtgtggtg ctgtgccccc agagtcgggc tctcctgttc tggtccccag   11880
ggagtgagaa gtgaggttga cttgtccctg ctcctctctg ctacccaac attcaccttc   11940
```

FIG.4G

```
tcctcatgcc cctctctctc aaatatgatt tggatctatg tccccgccca aatctcatgt   12000
caaattgtaa accccaatgt tggaggtggg gccttgtgag aagtgattgg ataatgcggg   12060
tggattttct gctttgatgc tgtttctgtg atagagatct cacatgatct ggttgtttaa   12120
aagtgtgtag cacctctccc ctctctctct ctctctctta ctcatgctct gccatgtaag   12180
acgttcctgt ttccccttca ccgtccagaa tgattgtaag ttttctgagg cctccccagg   12240
agcagaagcc actatgcttc ctgtacaact gcagaatgat gagcgaatta aacctctttt   12300
ctttataaat tacccagtct caggtatttc tttatagcaa tgcgaggaca gactaataca   12360
atcttctact cccagatccc cgcacacgct tagcccaga catcactgcc cctgggagca    12420
tgcacagcgc agcctcctgc cgacaaaagc aaagtcacaa aaggtgacaa aaatctgcat   12480
ttggggacat ctgattgtga aagagggagg acagtacact tgtagccaca gagactgggg   12540
ctcaccgagc tgaaacctgg tagcactttg gcataacatg tgcatgaccc gtgttcaatg   12600
tctagagatc agtgttgagt aaaacagcct ggtctggggc cgctgctgtc cccacttccc   12660
tcctgtccac cagagggcgg cagagttcct cccaccctgg agcctcccca ggggctgctg   12720
acctccctca gccgggccca cagcccagca gggtccaccc tcacccgggt cacctcggcc   12780
cacgtcctcc tcgccctccg agctcctcac acggactctg tcagctcctc cctgcagcct   12840
atcggccgcc cacctgaggc ttgtcggccg cccacttgag gcctgtcggc tgccctctgc   12900
aggcagctcc tgtcccctac accccctcct tccccgggct cagctgaaag ggcgtctccc   12960
agggcagctc cctgtgatct ccaggacagc tcagtctctc acaggctccg acgccccta   13020 tgctgtcacc tcacagccct gtcattacca ttaactcctc agtcccatga agttcactga   13080
gcgcctgtct cccggttaca ggaaaactct gtgacaggga ccacgtctgt cctgctctct   13140
gtggaatccc agggcccagc ccagtgcctg acacggaaca gatgctccat aaatactggt   13200
taaatgtgtg ggagatctct aaaaagaagc atatcacctc cgtgtggccc ccagcagtca   13260
gagtctgttc catgtggaca caggggcact ggcaccagca tgggaggagg ccagcaagtg   13320
cccgcggctg ccccaggaat gaggcctcaa cccccagagc ttcagaaggg aggacagagg   13380
cctgcaggga atagatcctc cggcctgacc ctgcagccta atccagagtt cagggtcagc   13440
tcacaccacg tcgaccctgg tcagcatccc tagggcagtt ccagacaagg ccggaggtct   13500
cctcttgccc tccaggggt gacattgcac acagacatca ctcaggaaac ggattcccct   13560
ggacaggaac ctggctttgc taaggaagtg gaggtggagc ctggtttcca tcccttgctc   13620
```

FIG.4H

```
caacagaccc ttctgatctc tcccacatac ctgctctgtt cctttctggg tcctatgagg    13680
accctgttct gccaggggtc cctgtgcaac tccagactcc ctcctggtac caccatgggg    13740
aaggtggggt gatcacagga cagtcagcct cgcagagaca gagaccaccc aggactgtca    13800
gggagaacat ggacaggccc tgagccgcag ctcagccaac agacacggag agggagggtc    13860
cccctggagc cttccccaag gacagcagag cccagagtca cccacctccc tccaccacag    13920
tcctctcttt ccaggacaca caagacacct cccctccac atgcaggatc tggggactcc    13980
tgagacctct gggcctgggt ctccatccct gggtcagtgg cggggttggt ggtactggag    14040
acagagggct ggtccctccc cagccaccac ccagtgagcc ttttctagc ccccagagcc    14100
acctctgtca ccttcctgtt gggcatcatc ccaccttccc agagccctgg agagcatggg    14160
gagacccggg accctgctgg gtttctctgt cacaaaggaa aataatcccc ctggtgtgac    14220
agacccaagg acagaacaca gcagaggtca gcactgggga agacaggttg tcctcccagg    14280
ggatgggggt ccatccacct tgccgaaaag atttgtctga ggaactgaaa atagaaggga    14340
aaaagagga gggacaaaag aggcagaaat gagaggggag gggacagagg acacctgaat    14400
aaagaccaca cccatgaccc acgtgatgct gagaagtact cctgccctag gaagagactc    14460
agggcagagg gaggaaggac agcagaccag acagtcacag cagccttgac aaaacgttcc    14520
tggaactcaa gctcttctcc acagaggagg acagagcaga cagcagagac catggagtct    14580
ccctcggccc ctccccacag atggtgcatc ccctggcaga ggctcctgct cacaggtgaa    14640
gggaggacaa cctgggagag ggtgggagga gggagctggg gtctcctggg taggacaggg    14700
ctgtgagacg gacagagggc tcctgttgga gcctgaatag ggaagaggac atcagagagg    14760
gacaggagtc acaccagaaa aatcaaattg aactggaatt ggaaagggc aggaaaacct    14820
caagagttct attttcctag ttaattgtca ctggccacta cgttttaaa aatcataata    14880
actgcatcag atgacacttt aaataaaaac ataaccaggg catgaaacac tgtcctcatc    14940
cgcctaccgc ggacattgga aaataagccc caggctgtgg agggccctgg gaaccctcat    15000
gaactcatcc acaggaatct gcagcctgtc ccaggcactg gggtgcaacc aagatc       15056
```

FIG.41

```
gaattcagaa ataggggaag gttgaggaag gacactgaac tcaaaggggga tacagtgatt  60
ggtttatttg tcttctcttc acaacattgg tgctggagga attcccaccc tgaggttatg 120
aagatgtctg aacacccaac acatagcact ggagatatga gctcgacaag agtttctcag 180
ccacagagat tcacagccta gggcaggagg acactgtacg ccaggcagaa tgacatggga 240
attgcgctca cgattggctt gaagaagcaa ggactgtggg aggtgggctt tgtagtaaca 300
agagggcagg gtgaactctg attcccatgg gggaatgtga tggtcctgtt acaaattttt 360
caagctggca gggaataaaa cccattacgg tgaggacctg tggagggcgg ctgccccaac 420
tgataaagga aatagccagg tgggggcctt tcccattgta gggggacat atctggcaat 480
agaagccttt gagacccttt agggtacaag tactgaggca gcaaataaaa tgaaatctta 540
tttttcaact ttatactgca tgggtgtgaa gatatatttg tttctgtaca gggggtgagg 600
gaaaggaggg gaggaggaaa gttcctgcag gtctggtttg gtcttgtgat ccaggggtc 660
ttggaactat ttaaattaaa ttaaattaaa acaagcgact gttttaaatt aaattaaatt 720
aaattaaatt ttactttatt ttatcttaag ttctgggcta catgtgcagg acgtgcagct 780
ttgttacata ggtaaacgtg tgccatggtg gtttgctgta cctatcaacc catcacctag 840
gtattaagcc cagcatgcat tagctgtttt tcctgacgct ctccctctcc ctgactccca 900
caacaggccc cagtgtgtgt tgttccctc cctgtgtcca tgtgttctca ttgttcagct 960
cccacttata agtgagaaca tgtggtgttt ggttttctgt ttctgtgtta gtttgctgag 1020
gataatggct tccacctcca tccatgttcc tgcaaaggac gtgatcttat tcttttttat 1080
ggttgcatag aaattgtttt tacaaatcca attgatattg tatttaatta caagttaatc 1140
taattagcat actagaagag attacagaag atattaggta cattgaatga ggaaatatat 1200
aaaataggac gaaggtgaaa tattaggtag gaaaagtata atagttgaaa gaagtaaaaa 1260
aaaatatgca tgagtagcag aatgtaaaag aggtgaagaa cgtaatagtg acttttttaga 1320
ccagattgaa ggacagagac agaaaaattt taaggaattg ctaaaccatg tgagtgttag 1380
aagtacagtc aataacatta aagcctcagg aggagaaaag aataggaaag gaggaaatat 1440
gtgaataaat agtagagaca tgtttgatgg atttttaaaat atttgaaaga cctcacatca 1500
aaggattcat accgtgccat tgaagaggaa gatggaaaag ccaagaagcc agatgaaagt 1560
tagaaatatt attggcaaag cttaaatgtt aaaagtccta gagagaaagg atggcagaaa 1620
tattggcggg aaagaatgca gaacctagaa tataaattca tcccaacagt ttggtagtgt 1680
```

FIG.5A

```
gcagctgtag  ccttttctag  ataatacact  attgtcatac  atcgcttaag  cgagtgtaaa  1740
atggtctcct  cactttattt  atttatatat  ttatttagtt  ttgagatgga  gcctcgctct  1800
gtctcctagg  ctggagtgca  atagtgcgat  accactcact  gcaacctctg  cctcctctgt  1860
tcaagtgatt  ttcttacctc  agcctcccga  gtagctggga  ttacaggtgc  gtgccaccac  1920
acccggctaa  ttttgtatt   ttttgtagag  acggggtttt  gccatgttgg  ccaggctggt  1980
cttgaactcc  tgacatcagg  tgatccacct  gccttggcct  cctaaagtgc  tgggattaca  2040
ggcatgagcc  accgtgccca  accactttat  ttatttttta  tttttatttt  taaatttcag  2100
cttctatttg  aaatacaggg  ggcacatata  taggattgtt  acatgggtat  attgaactca  2160
ggtagtgatc  atactaccca  acaggtaggt  tttcaaccca  ctcccctct   tttcctcccc  2220
attctagtag  tgtgcagtgt  ctattgttct  catgtttatg  tctatgtgtg  ctccaggttt  2280
agctcccacc  tgtaagtgag  aacgtgtggt  atttgatttt  ctgtccctgt  gttaattcac  2340
ttaggattat  ggcttccagc  tccattcata  ttgctgtaaa  ggatatgatt  cattttcat   2400
ggccatgcag  tattccatat  tgcgtataga  tcacattttc  tttctttttt  tttttgaga   2460
cggagtcttg  ctttgctgcc  taggctggag  tgcagtagca  cgatctcggc  tcactgcaag  2520
cttcacctcc  ggggttcacg  tcattcttct  gtctcagctt  cccaagtagc  tgggactaca  2580
ggcgcccgcc  accacgtccg  gctaattttt  ttgtgtgttt  ttagtagaga  tggggtttc   2640
actgtgttag  ccaggatggt  cttgatctcc  tgaccttgtg  gtccacctgc  ctcggtctcc  2700
caaagtgctg  ggattacagg  ggtgagccac  tgcgcccggc  ccatatatac  cacatttct   2760
ttaaccaatc  caccattgat  gggcaactag  gtagattcca  tggattccac  agtttgcta   2820
ttgtgtgcag  tgtggcagta  gacatatgaa  tgaatgtgtc  tttttggtat  aatgatttgc  2880
attcctttgg  gtatacagtc  attaatagga  gtgctgggtt  gaacggtggc  tctgtttaaa  2940
attctttgag  aattttccaa  actgtttgcc  atagagagca  aactaattta  catttccacg  3000
aacagtatat  aagcattccc  ttttctccac  agctttgtca  tcatggtttt  ttttttttctt 3060
tattttaaaa  aagaatatgt  tgttgttttc  ccagggtaca  tgtgcaggat  gtgcaggttt  3120
gttacatagg  tagtaaacgt  gagccatggt  ggtttgctgc  acctgtcaac  ccattacctg  3180
ggtatgaagc  cctgcctgca  ttagctcttt  tccctaatgc  tctcactact  gccccaccct  3240
caccctgaca  gggcaaacag  acaacctaca  gaatgggagg  aaattttgc   aatctattca  3300
tctgacaaag  gtcaagaata  tccagaatct  acaaggaact  taagcaaatt  tttactttt   3360
```

FIG.5B

```
aataatagcc actctgactg gcgtgaaatg gtatctcatt gtggttttca tttgaatttc 3420
tctgatgatc agtgacgatg agcattttt catatttgtt ggctgcttgt acgtcttttg 3480
agaagtgtct cttcatgcct tttggccact ttaatgggat tatttttgc tttttagttt 3540
aagttcctta tagattctgg atattagact tcttattgga tgcatagttt gtgaatactc 3600
tcttccattc tgtaggttgt ctgtttactc tattgatggc ttcttttgct gtgccgaagc 3660
atcttagttt aattagaaac cacctgccaa tttttgtttt tgttgcaatt gcttttgggg 3720
acttagtcat aaactctttg ccaaggtctg ggtcaagaag agtatttcct aggttttctt 3780
ctagaatttt gaaagtctga atgtaaacat ttgcattttt aatgcatctt gagttagttt 3840
ttgtatatgt gaaaggtcta ctctcatttt ctttccctct tctttctttt ctttcttttc 3900
tttctttctt tctttctttc tttctttctt tctttctttc tttcttttg tccttctttc 3960
tttctttctt tctctttctt tctctctttc tttttttttt ttgatggagt attgctctgt 4020
tgcccaggct gcagtgcagc ggcacgatct cggctcactg caacctctgc ctcctgggtt 4080
caactgattc tcctgcatca gccttccaag tagctgggat tataggcgcc cgccaccacg 4140
cccgactaat ttttgtattt ttagtagaga cggggttgtg ccatgttggc caggctggtt 4200
tgaaactcct gacctcaaac gatctgcctg ccttggcctc ccaaagtgct gggattacag 4260
gtgtgagcca ctgtgcccag ccaagaatgt catttctaa gaggtccaag aacctcaaga 4320
tattttggga ccttgagaag agaggaattc atacaggtat tacaagcaca gcctaatggc 4380
aaatctttgg catggcttgg cttcaagact ttaggctctt aaaagtcgaa tccaaaaatt 4440
tttataaaag ctccagctaa gctaccttaa aagggcctg tatggctgat cactcttctt 4500
gctatacttt acacaaataa acaggccaaa tataatgagg ccaaaattta ttttgcaaat 4560
aaattggtcc tgctatgatt tactcttggt aagaacaggg aaaatagaga aaaatttaga 4620
ttgcatctga cctttttttc tgaatttta tatgtgccta caatttgagc taaatcctga 4680
attattttct ggttgcaaaa actctctaaa gaagaacttg gttttcattg tcttcgtgac 4740
acatttatct ggctctttac tagaacagct ttcttgtttt tggtgttcta gcttgtgtgc 4800
cttacagttc tactcttcaa attattgtta tgtgtatctc atagtttcc ttcttttgag 4860
aaaactgaag ccatggtatt ctgaggacta gagatgactc aacagagctg gtgaatctcc 4920
tcatatgcaa tccactgggc tcgatctgct tcaaattgct gatgcactgc tgctaaagct 4980
atacatttaa aaccctcact aaaggatcag ggaccatcat ggaagaggag gaaacatgaa 5040
attgtaagag ccagattcgg ggggtagagt gtggaggtca gagcaactcc accttgaata 5100
```

FIG.5C

```
agaaggtaaa gcaacctatc ctgaaagcta acctgccatg gtggcttctg attaacctct 5160
gttctaggaa gactgacagt ttgggtctgt gtcattgccc aaatctcatg ttaaattgta 5220
atccccagtg ttcggaggtg ggacttggtg gtaggtgatt cggtcatggg agtagatttt 5280
cttctttgtg gtgttacagt gatagtgagt gagttctcgt gagatctggt catttaaaag 5340
tgtgtggccc ctcccctccc tctcttggtc ctcctactgc catgtaagat acctgctcct 5400
gctttgcctt ctaccataag taaaagcccc ctgaggcctc cccagaagca gatgccacca 5460
tgcttcctgt acagcctgca gaaccatcag ccaattaaac ctcttttctg tataaattac 5520
cagtcttgag tatctcttta cagcagtgtg agaacggact aatacaaggg tctccaaaat 5580
tccaagttta tgtattcttt cttgccaaat agcaggtatt taccataaat cctgtcctta 5640
ggtcaaacaa ccttgatggc atcgtacttc aattgtctta cacattcctt ctgaatgact 5700
cctcccctat ggcatataag ccctgggtct tgggggataa tggcagaggg gtccaccatc 5760
ttgtctggct gccacctgag acacggacat ggcttctgtt ggtaagtctc tattaaatgt 5820
ttctttctaa gaaactggat ttgtcagctt gtttctttgg cctctcagct tcctcagact 5880
ttggggtagg ttgcacaacc ctgcccacca cgaaacaaat gtttaatatg ataaatatgg 5940
atagatataa tccacataaa taaaagctct tggagggccc tcaataattg ttaagagtgt 6000
aaatgtgtcc aaagatggaa aatgtttgag aactactgtc ccagagattt tcctgagttc 6060
tagagtgtgg gaatatagaa cctggagctt ggcttcttca gcctagaatc aggagtatgg 6120
ggctgaagtc tgaagcttgg cttcagcagt ttggggttgg cttccggagc acatatttga 6180
catgttgcga ctgtgatttg gggtttggta tttgctctga atcctaatgt ctgtccttga 6240
ggcatctaga atctgaaatc tgtggtcaga attctattat cttgagtagg acatctccag 6300
tcctggttct gccttctagg gctggagtct gtagtcagtg acccggtctg gcatttcaac 6360
ttcatataca gtgggctatc ttttggtcca tgtttcaacc aaacaaccga ataaaccatt 6420
agaacctttc cccacttccc tagctgcaat gttaaaccta ggatttctgt ttaataggtt 6480
catatgaata atttcagcct gatccaactt tacattcctt ctaccgttat tctacaccca 6540
ccttaaaaat gcattcccaa tatattccct ggattctacc tatatatggt aatcctggct 6600
ttgccagttt ctagtgcatt aacatacctg atttacattc ttttacttta aagtggaaat 6660
aagagtccct ctgcagagtt caggagttct caagatggcc cttacttctg acatcaattg 6720
agatttcaag ggagtcgcca agatcatcct caggttcagt gattgctggt agccctcata 6780
```

FIG. 5D

```
taactcaatg aaagctgtta tgctcatggc tatggtttat tacagcaaaa gaatagagat 6840
gaaaatctag caagggaaga gttgcatggg gcaaagacaa ggagagctcc aagtgcagag 6900
attcctgttg ttttctccca gtggtgtcat ggaaagcagt atcttctcca tacaatgatg 6960
tgtgataata ttcagtgtat tgccaatcag ggaactcaac tgagccttga ttatattgga 7020
gcttggttgc acagacatgt cgaccacctt catggctgaa ctttagtact tagcccctcc 7080
agacgtctac agctgatagg ctgtaaccca acattgtcac cataaatcac attgttagac 7140
tatccagtgt ggcccaagct cccgtgtaaa cacaggcact ctaaacaggc aggatatttc 7200
aaaagcttag agatgacctc ccaggagctg aatgcaaaga cctggcctct ttgggcaagg 7260
agaatccttt accgcacact ctccttcaca gggttattgt gaggatcaaa tgtggtcatg 7320
tgtgtgagac accagcacat gtctggctgt ggagagtgac ttctatgtgt gctaacattg 7380
ctgagtgcta agaaagtatt aggcatggct ttcagcactc acagatgctc atctaatcct 7440
cacaacatgg ctacagggtg ggcactacta gcctcatttg acagaggaaa ggactgtgga 7500
taagaagggg gtgaccaata ggtcagagtc attctggatg caagggctc cagaggacca 7560
tgattagaca ttgtctgcag agaaattatg gctggatgtc tctgccccgg aaaggggat 7620
gcactttcct tgaccccta tctcagatct tgactttgag gttatctcag acttcctcta 7680
tgataccagg agcccatcat aatctctctg tgtcctctcc ccttcctcag tcttactgcc 7740
cactcttccc agctccatct ccagctggcc aggtgtagcc acagtaccta actctttgca 7800
gagaactata aatgtgtatc ctacagggga gaaaaaaaa aagaactctg aaagagctga 7860
cattttaccg acttgcaaac acataagcta acctgccagt tttgtgctgg tagaactcat 7920
gagactcctg ggtcagaggc aaaagatttt attacccaca gctaaggagg cagcatgaac 7980
tttgtgttca catttgttca ctttgccccc caattcatat gggatgatca gagcagttca 8040
ggtggatgga cacagggggtt tgtggcaaag gtgagcaacc taggcttaga aatcctcaat 8100
cttataagaa ggtactagca aacttgtcca gtctttgtat ctgacggaga tattatcttt 8160
ataattgggt tgaaagcaga cctactctgg aggaacatat tgtatttatt gtcctgaaca 8220
gtaaacaaat ctgctgtaaa atagacgtta actttattat ctaaggcagt aagcaaacct 8280
agatctgaag gcgataccat cttgcaaggc tatctgctgt acaaatatgc ttgaaaagat 8340
ggtccagaaa agaaaacggt attattgcct ttgctcagaa gacacacaga aacataagag 8400
aaccatggaa aattgtctcc caacactgtt cacccagagc cttccactct tgtctgcagg 8460
acagtcttaa catcccatca ttagtgtgtc taccacatct ggcttcaccg tgcctaacca 8520
```

FIG.5E

```
agatttctag gtccagttcc ccaccatgtt tggcagtgcc ccactgccaa ccccagaata 8580
agggagtgct cagaattccg aggggacatg ggtggggatc agaacttctg ggcttgagtg 8640
cagagggggc ccatactcct tggttccgaa ggaggaagag gctggaggtg aatgtccttg 8700
gaggggagga atgtgggttc tgaactctta aatccccaag ggaggagact ggtaaggtcc 8760
cagcttccga ggtactgacg tgggaatggc ctgagaggtc taagaatccc gtatcctcgg 8820
gaaggagggg ctgaaattgt gaggggttga gttgcagggg tttgttagct tgagactcct 8880
tggtgggtcc ctgggaagca aggactggaa ccattggctc cagggtttgg tgtgaaggta 8940
atgggatctc ctgattctca aagggtcaga ggactgagag ttgcccatgc tttgatcttt 9000
ccatctactc cttactccac ttgagggtaa tcacctactc ttctagttcc acaagagtgc 9060
gcctgcgcga gtataatctg cacatgtgcc atgtcccgag gcctggggca tcatccactc 9120
atcattcagc atctgcgcta tgcgggcgag gccggcgcca tgacgtcatg tagctgcgac 9180
tatccctgca gcgcgcctct cccgtcacgt cccaaccatg gagctgtgga cgtgcgtccc 9240
ctggtggatg tggcctgcgt ggtgccaggc cggggcctgg tgtccgataa agatcctaga 9300
accacaggaa accaggactg aaaggtgcta gagaatggcc atatgtcgct gtccatgaaa 9360
tctcaaggac ttctgggtgg agggcacagg agcctgaact tacgggtttg ccccagtcca 9420
ctgtcctccc aagtgagtct cccagatacg aggcactgtg ccagcatcag cttcatctgt 9480
accacatctt gtaacaggga ctacccagga ccctgatgaa caccatggtg tgtgcaggaa 9540
gaggggtga aggcatggac tcctgtgtgg tcagagccca gaggggggcca tgacgggtgg 9600
ggaggaggct gtggactggc tcgagaagtg ggatgtggtt gtgtttgatt cctttggcc 9660
agataaagtg ctggatatag cattgaaaac ggagtatgaa gaccagttag aatggagggt 9720
caggttggag ttgagttaca gatggggtaa aattctgctt cggatgagtt tggggattgg 9780
caatctaaag gtggtttggg atggcatggc tttgggatgg aaataggttt gttttatgt 9840
tggctgggaa gggtgtgggg attgaattgg ggatgaagta ggtttagttt ggagataga 9900
atacatggag ctggctattg catgcgagga tgtgcattag tttggtttga tctttaaata 9960
aaggaggcta ttagggttgt cttgaattag attaagttgt gttgggttga tgggttgggc 10020
ttgtgggtga tgtggttgga ttgggctgtg ttaaattggt ttgggtcagg ttttggttga 10080
ggttatcatg gggatgagga tatgcttggg acatggattc agtggttct cattcaagct 10140
gaggcaaatt tcctttcaga cggtcattcc agggaacgag tggttgtgtg ggggaaatca 10200
```

FIG.5F

```
ggccactggc tgtgaatatc cctctatcct ggtcttgaat tgtgattatc tatgtccatt 10260
ctgtctcctt cactgtactt ggaattgatc tggtcattca gctggaaatg ggggaagatt 10320
ttgtcaaatt cttgagacac agctgggtct ggatcagcgt aagccttcct tctggtttta 10380
ttgaacagat gaaatcacat ttttttttc aaaatcacag aaatcttata gagttaacag 10440
tggactctta taataagagt taacaccagg actcttattc ttgattcttt tctgagacac 10500
caaaatgaga tttctcaatg ccaccctaat tctttttttt ttttttttt ttttgagac 10560
acagtctggg tcttttgctc tgtcactcag gctggagcgc agtggtgtga tcatagctca 10620
ctgaacccct gacctcctgg acttaaggga tcctcctgct tcagcctcct gagtagatgg 10680
ggctacaggt gcttgccacc acacctggct aattaaattt ttttttttt tttgtagaga 10740
aagggtctca ctttgttgcc ctggctgatc ttgaacttct gacttcaagt gattcttcag 10800
ccttggactc ccaaagcact gggattgctg gcatgagcca ctcaccgtgc ctggcttgca 10860
gcttaatctt ggagtgtata aacctggctc ctgatagcta gacatttcag tgagaaggag 10920
gcattggatt ttgcatgagg acaattctga cctaggaggg caggtcaaca ggaatccccg 10980
ctgtacctgt acgttgtaca ggcatggaga atgaggagtg aggaggccgt accggaaccc 11040
catattgttt agtggacatt ggattttgaa ataataggga acttggtctg ggagagtcat 11100
atttctggat tggacaatat gtggtatcac aaggttttat gatgagggag aaatgtatgt 11160
ggggaaccat tttctgagtg tggaagtgca agaatcagag agtagctgaa tgccaacgct 11220
tctatttcag gaacatggta agttggaggt ccagctctcg ggctcagacg ggtataggga 11280
ccaggaagtc tcacaatccg atcattctga tatttcaggg catattaggt ttggggtgca 11340
aaggaagtac ttgggactta ggcacatgag actttgtatt gaaaatcaat gattggggct 11400
ggccgtggtg ctcacgcctg taatctcatc actttgggag accgaagtgg gaggatggct 11460
tgatctcaag agttggacac cagcctaggc aacatggcca gaccctctct ctacaaaaaa 11520
attaaaaatt agctggatgt ggtggtgcat gcttgtggtc tcagctatcc tggaggctga 11580
gacaggagaa tcggttgagt ctgggagttc aaggctacag ggagctgcga tcacgccgct 11640
gcactccagc ctgggaaaca gagtgagact gtctcagaat ttttttaaaa aagaatcagt 11700
gatcatccca acccctgttg ctgttcatcc tgagcctgcc ttctctggct ttgttcccta 11760
gatcacatct ccatgatcca taggccctgc ccaatctgac ctcacaccgt gggaatgcct 11820
ccagactgat ctagtatgtg tggaacagca agtgctggct ctccctcccc ttccacagct 11880
ctgggtgtgg gagggggttg tccagcctcc agcagcatgg ggagggcctt ggtcagcatc 11940
```

FIG.5G

```
taggtgccaa cagggcaagg gcggggtcct ggagaatgaa ggctttatag ggctcctcag 12000
ggaggccccc cagccccaaa ctgcaccacc tggccgtgga caccggt              12047
```

FIG.5H

```
cgagcggccc ctcagcttcg gcgcccagcc ccgcaaggct cccggtgacc actagagggc   60
gggaggagct cctggccagt ggtggagagt ggcaaggaag gaccctaggg ttcatcggag  120
cccaggttta ctcccttaag tggaaatttc ttcccccact cctccttggc tttctccaag  180
gagggaaccc aggctgctgg aaagtccggc tggggcgggg actgtgggtt caggggagaa  240
cggggtgtgg aacgggacag ggagcggtta gaagggtggg gctattccgg gaagtggtgg  300
ggggagggag cccaaaacta gcacctagtc cactcattat ccagccctct tatttctcgg  360
ccgctctgct tcagtggacc cggggagggc ggggaagtgg agtgggagac ctagggtgg  420
gcttcccgac cttgctgtac aggacctcga cctagctggc tttgttcccc atccccacgt  480
tagttgttgc cctgaggcta aaactagagc ccagggccc caagttccag actgcccctc  540
cccctcccc cggagccagg gagtggttgg tgaaaggggg aggccagctg gagaacaaac  600
gggtagtcag ggggttgagc gattagagcc cttgtaccct acccaggaat ggttggggag  660
gaggaggaag aggtaggagg tagggaggg ggcggggttt tgtcacctgt cacctgctcg  720
ctgtgcctag ggcgggcggg cggggagtgg ggggaccggt ataaagcggt aggcgcctgt  780
gcccgctcca cctctcaagc agccagcgcc tgcctgaatc tgttctgccc cctccccacc  840
catttcacca ccaccatg                                                858
```

FIG. 6

```
aagcttccac aagtgcattt agcctctcca gtattgctga tgaatccaca gttcaggttc   60
aatggcgttc aaaacttgat caaaaatgac cagactttat attcttacac caacatctat  120
ctgattggag gaatggataa tagtcatcat gtttaaacat ctaccattcc agttaagaaa  180
atatgatagc atcttgttct tagtcttttt cttaataggg acataaagcc cacaaataaa  240
aatatgcctg aagaatggga caggcattgg gcattgtcca tgcctagtaa agtactccaa  300
gaacctattt gtatactaga tgacacaatg tcaatgtctg tgtacaactg ccaactggga  360
tgcaagacac tgcccatgcc aatcatcctg aaaagcagct ataaaaagca ggaagctact  420
ctgcaccttg tcagtgaggt ccagatacct acag                              454
```

FIG.7

```
g atg acc ggc tca acc atc gcg ccc aca acg gac tat cgc aac acc act    49
  Met Thr Gly Ser Thr Ile Ala Pro Thr Thr Asp Tyr Arg Asn Thr Thr
    1           5               10              15 gct acc gga cta aca tct gcc cta aat tta ccc caa gtt cat gcc ttt       97
Ala Thr Gly Leu Thr Ser Ala Leu Asn Leu Pro Gln Val His Ala Phe
            20              25              30 gtc aat gac tgg gcg agc ttg gac atg tgg tgg ttt tcc ata gcg ctt      145
Val Asn Asp Trp Ala Ser Leu Asp Met Trp Trp Phe Ser Ile Ala Leu
        35              40              45 atg ttt gtt tgc ctt att att atg tgg ctt att tgt tgc cta aag cgc      193
Met Phe Val Cys Leu Ile Ile Met Trp Leu Ile Cys Cys Leu Lys Arg
    50              55              60 aga cgc gcc aga ccc ccc atc tat agg cct atc att gtg ctc aac cca      241
Arg Arg Ala Arg Pro Pro Ile Tyr Arg Pro Ile Ile Val Leu Asn Pro
65              70              75              80 cac aat gaa aaa att cat aga ttg gac ggt ctg aaa cca tgt tct ctt      289
His Asn Glu Lys Ile His Arg Leu Asp Gly Leu Lys Pro Cys Ser Leu
            85              90              95 ctt tta cag tat gat taa                                              307
Leu Leu Gln Tyr Asp
        100
```

FIG.8

ADENOVIRUS VECTORS CONTAINING CELL STATUS-SPECIFIC RESPONSE ELEMENTS AND METHODS OF USE THEREOF

CROSS-REFERENCE TO RELATED APPLICATIONS

This application claims the priority benefit of U.S. Provisional Patent Application No. 60/099,791, filed Sep. 10, 1998. The priority application is hereby incorporated herein by reference in its entirety.

STATEMENT OF RIGHTS TO INVENTIONS MADE UNDER FEDERALLY SPONSORED RESEARCH (Not Applicable)

TECHNICAL FIELD

This invention relates to cell transfection using adenoviral vectors. More specifically, it relates to cell status-specific replication of adenovirus vectors in cells, regardless of tissue or cell type.

BACKGROUND ART

In spite of numerous advances in medical research, cancer remains the second leading cause of death in the United States. In the industrialized nations, roughly one in five persons will die of cancer. Traditional modes of clinical care, such as surgical resection, radiotherapy and chemotherapy, have a significant failure rate, especially for solid tumors. Neoplasia resulting in benign tumors can usually be completely cured by removing the mass surgically. If a tumor becomes malignant, as manifested by invasion of surrounding tissue, it becomes much more difficult to eradicate. Once a malignant tumor metastasizes, it is much less likely to be eradicated.

Excluding basal cell carcinoma, there are over one million new cases of cancer per year in the United States alone, and cancer accounts for over one half million deaths per year in this country. In the world as a whole, the five most common cancers are those of lung, stomach, breast, colon/rectum, and uterine cervix, and the total number of new cases per year is over 6 million.

Lung cancer is one of the most refractory of solid tumors because inoperable cases are up to 60% and the 5-year survival is only 13%. In particular, adenocarcinomas, which comprise about one-half of the total lung cancer cases, are mostly chemo-radioresistant. Colorectal cancer is the third most common cancer and the second leading cause of cancer deaths. Pancreatic cancer is virtually always fatal. Thus, current treatment prospects for many patients with these carcinomas are unsatisfactory, and the prognosis is poor.

Hepatocellular carcinoma (HCC or malignant hepatoma) is one of the most common cancers in the world, and is especially problematic in Asia. Treatment prospects for patients with hepatocellular carcinoma are dim. Even with improvements in therapy and availability of liver transplant, only a minority of patients are cured by removal of the tumor either by resection or transplantation. For the majority of patients, the current treatments remain unsatisfactory, and the prognosis is poor.

Breast cancer is one of the most common cancers in the United States, with an annual incidence of about 182,000 new cases and nearly 50,000 deaths. In the industrial nations, approximately one in eight women can expect to develop breast cancer. The mortality rate for breast cancer has remained unchanged since 1930. It has increased an average of 0.2% per year, but decreased in women under 65 years of age by an average of 0.3% per year. See e.g., Marchant (1994) Contemporary Management of Breast Disease II: Breast Cancer, in: *Obstetrics and Gynecology Clinics of North America* 21:555–560; and Colditz (1993) *Cancer Suppl.* 71:1480–1489.

Despite ongoing improvement in the understanding of the disease, breast cancer has remained resistant to medical intervention. Most clinical initiatives are focused on early diagnosis, followed by conventional forms of intervention, particularly surgery and chemotherapy. Such interventions are of limited success, particularly in patients where the tumor has undergone metastasis. There is a pressing need to improve the arsenal of therapies available to provide more precise and more effective treatment in a less invasive way.

Prostate cancer is the fastest growing neoplasm in men with an estimated 244,000 new cases in the United States being diagnosed in 1995, of which approximately 44,000 deaths will result. Prostate cancer is now the most frequently diagnosed cancer in men. Prostate cancer is latent; many men carry prostate cancer cells without overt signs of disease. It is associated with a high morbidity. Cancer metastasis to bone (late stage) is common and is almost always fatal.

Current treatments include radical prostatectomy, radiation therapy, hormonal ablation and chemotherapy. Unfortunately, in approximately 80% of cases, diagnosis of prostate cancer is established when the disease has already metastasized to the bones, thus limiting the effectiveness of surgical treatments. Hormonal therapy frequently fails with time with the development of hormone-resistant tumor cells. Although chemotherapeutic agents have been used in the treatment of prostate cancer, no single agent has demonstrated superiority over its counterparts, and no drug combination seems particularly effective. The generally drug-resistant, slow-growing nature of most prostate cancers makes them particularly unresponsive to standard chemotherapy.

A major, indeed the overwhelming, obstacle to cancer therapy is the problem of selectivity; that is, the ability to inhibit the multiplication of tumor cells, while leaving unaffected the function of normal cells. For example, in prostate cancer therapy, the therapeutic ratio, or ratio of tumor cell killing to normal cell killing of traditional tumor chemotherapy, is only 1.5:1. Thus, more effective treatment methods and pharmaceutical compositions for therapy and prophylaxis of neoplasia are needed.

Solid tumors frequently contain regions that are poorly vascularized, partly because the tumor cells grow faster than the endothelial cells that make up the blood vessels. Tumor cells can remain viable in such hypoxic conditions and are often refractory to chemotherapy and radiation therapy. In a recent study of cervical cancer, the oxygen status of a tumor was shown to be the single most important prognostic factor, ahead of age of patient, menopausal status, clinical stage, size and histology. Hoeckel et al. (1996) *Semin. Radiat. Oncol.* 6:1–8.

Of particular interest is development of more specific, targeted forms of cancer therapy, especially for cancers that are difficult to treat successfully. In contrast to conventional cancer therapies, which result in relatively non-specific and often serious toxicity, more specific treatment modalities attempt to inhibit or kill malignant cells selectively while leaving healthy cells intact. Radioresistant and chemoresistant tumors present particular challenges, and there is a need for methods of treating these types of tumors.

One possible treatment approach for many of these cancers is gene therapy, whereby a gene of interest is introduced into the malignant cell. Various viral vectors, including adenoviral vectors, have been developed as vehicles for gene therapy. The virtually exclusive focus in development of adenoviral vectors for gene therapy is use of adenovirus merely as a vehicle for introducing the gene of interest, not as an effector in itself. Replication of adenovirus has been viewed as an undesirable result, largely due to the host immune response. In the treatment of cancer by replication-defective adenoviruses, the host immune response limits the duration of repeat doses at two levels. First, the capsid proteins of the adenovirus delivery vehicle itself are immunogenic. Second, viral late genes are frequently expressed in transduced cells, eliciting cellular immunity. Thus, the ability to repeatedly administer cytokines, tumor suppressor genes, ribozymes, suicide genes, or genes which convert prodrug to an active drug has been limited by the immunogenicity of both the gene transfer vehicle and the viral gene products of the transfer vehicle as well as the transient nature of gene expression.

Use of adenoviral vectors as therapeutic vehicles for cancer has been reported. Some of these approaches utilize tissue (i.e., cell type) specific transcriptional regulatory elements to selectively drive adenoviral replication (and thus cytotoxcity). U.S. Pat. No. 5,698,443; see also WO 95/11984; WO 96/17053; WO 96/34969; WO 98/35028. While useful and promising, there remain other treatment contexts for which tissue specific replication may be insufficient.

Besides cancerous cells, it is often desirable to selectively destroy certain unwanted cells or tissues. Besides surgery, however, which is invasive, there is a dearth of methods available, particularly non-invasive methods, which would allow such selective cytotoxicity and/or suppression.

There is a need for vector constructs that are capable of eliminating essentially all cancerous cells in a minimum number of administrations before specific immunological response against the vector prevents further treatment and which are suitable for use in specific, focused cancer ablation treatments. There is also a need for an ability to selectively destroy, or impair, unwanted cells, regardless of cell type and/or regardless of anatomical location.

SUMMARY OF THE INVENTION

Replication-competent adenoviral vectors specific for cells in a given, or particular, physiological state that permits or induces expression of polynucleotides under transcriptional control of a cell status-specific TRE, and methods for their use are provided. In these replication-competent adenovirus vectors, one or more adenoviral genes is under transcriptional control of an cell status-specific transcriptional regulatory element (TRE). Preferably, the adenoviral gene under transcriptional control of a cell status-specific TRE is one that is essential for adenoviral propagation. A transgene under control of the cell status-specific TRE may also be present. For the adenoviral vectors of the present invention, a cell status-specific TRE is active in a cell existing in a particular, reversible, physiological state, which may be an aberrant physiological state, i.e., a physiological state that deviates from the typical, or normal, physiological state of that same cell when in a non-dividing or regulated dividing state under normal, physiological conditions.

Accordingly, in one aspect, the invention provides an adenovirus vector comprising an adenovirus gene, wherein said adenovirus gene is under transcriptional control of a cell status-specific TRE. In another embodiment, a cell status-specific TRE is human. In another embodiment, a cell status-specific TRE comprises a cell status-specific promoter and enhancer. In yet another embodiment, a cell status-specific TRE is juxtaposed with a cell type-specific TRE, and together the two elements control expression of an adenovirus gene. Thus, the invention provides adenovirus vectors comprising a TRE comprising a cell status-specific TRE and a cell type-specific TRE.

In some embodiments, the adenovirus gene under transcriptional control of a cell status-specific TRE is an adenovirus gene essential for replication. In some embodiments, the adenoviral gene essential for replication is an early gene. In another embodiment, the early gene is E1A. In another embodiment, the early gene is E1B. In yet another embodiment, both E1A and E1B are under transcriptional control of a cell status-specific TRE. In other embodiments, the adenovirus gene essential for replication is a late gene.

In another embodiment, the cell status-specific TRE comprises a hypoxia responsive element. In another embodiment, the cell status-specific TRE comprises the nucleotide sequence of SEQ ID NO:1.

In another embodiment, the cell status-specific TRE comprises a cell cycle-specific TRE. The cell cycle-specific TRE can be derived from the E2F1 5' flanking region. In one embodiment, the cell cycle-specific TRE comprises the nucleotide sequence depicted in SEQ ID NO:2.

In other embodiments, the adenovirus vector can further comprise a transgene, wherein said transgene is under transcriptional control of an cell status-specific TRE. In some embodiments, the transgene is a cytotoxic gene.

In other embodiments, the adenoviral vector comprises an adenoviral gene essential for adenoviral replication under control of a first cell status-specific TRE, and a second adenoviral gene essential for adenoviral replication under control of a second cell status-specific TRE. The first and the second cell status-specific TREs can be identical, substantially identical, or different from, one another.

In other embodiments, the adenoviral vector comprises an adenoviral gene essential for adenoviral replication under control of a first cell status-specific TRE, and a transgene under control of a second cell status-specific TRE. The first and the second cell status-specific TREs can be substantially identical to, or different from, one another.

In other embodiments, the adenovirus vector comprises an adenovirus gene under transcriptional control of a cell status-specific TRE, and a second adenovirus gene under transcriptional control of a cell type-specific TRE. In other embodiments, the adenovirus vector comprises an adenovirus gene under transcriptional control of a cell status-specific TRE, and a transgene under transcriptional control of a cell type-specific TRE.

In another aspect, the invention provides a host cell comprising the adenovirus vector(s) described herein.

In another aspect, the invention provides pharmaceutical compositions comprising an adenovirus vector(s) described herein.

In another aspect, the invention provides kits which contain an adenoviral vector(s) described herein.

In another aspect, methods are provided for conferring selective cytotoxicity in target cells (i.e., cells which permit or induce a cell status-specific TRE to function), comprising contacting the cells with an adenovirus vector(s) described herein, whereby the vector enters the cell.

Another embodiment of the invention is an adenovirus which replicates preferentially in mammalian cells whose cell status permits or induces the function of a cell status-specific TRE.

In another aspect, methods are provided for propagating an adenovirus specific for mammalian cells whose cell status permits the function of a cell status-specific TRE, said method comprising combining an adenovirus vector(s) described herein with mammalian cells whose cell status permits the function of a cell status-specific TRE, whereby said adenovirus is propagated.

The invention further provides methods of suppressing tumor cell growth, more particularly a target tumor cell (i.e., a tumor cell that permits or induces a cell status-specific TRE to function), comprising contacting a tumor cell with an adenoviral vector of the invention such that the adenoviral vector enters the tumor cell and exhibits selective cytotoxicity for the tumor cell.

In another aspect, methods are provided for detecting cells whose cell status permits the function of a cell status-specific TRE in a biological sample, comprising contacting cells of a biological sample with an adenovirus vector(s) described herein, and detecting replication of the adenovirus vector, if any.

BRIEF DESCRIPTION OF THE DRAWINGS

FIG. 2 shows the nucleotide sequence of the 5' flanking region of a human E2F1 gene (SEQ ID NO: 1). The asterisk indicates the transcription start site.

FIG. 3 depicts a nucleotide sequence of a prostate-specific antigen TRE.

FIG. 4 depicts a nucleotide sequence of a carcinoembryonic antigen TRE.

FIG. 5 depicts a nucleotide sequence of a human glandular kallikrein TRE.

FIG. 6 depicts a nucleotide sequence of a mucin TRE.

FIG. 7 depicts a nucleotide sequence of a rat probasin TRE.

FIG. 8 depicts a nucleotide sequence and translated amino acid sequence of an adenovirus death protein.

MODES FOR CARRYING OUT THE INVENTION

Figure 1:
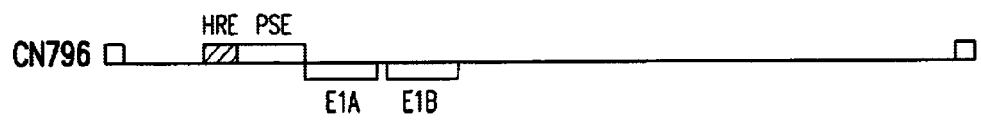
FIG. 1 is a schematic representation of adenovirus vector CN796, in which the E1A gene is under transcriptional control of an HRE and a PSA-TRE, as described in Example 1.

We have discovered and constructed replication-competent adenovirus vectors which contain an adenoviral gene under transcriptional control of a cell status-specific transcriptional response element (TRE) such that the adenovirus gene is transcribed preferentially in cells whose cell status permit the function of the cell status-specific TRE, and have developed methods using these adenovirus vectors. In some preferred embodiments, the adenovirus vectors of this invention comprise at least one adenovirus gene necessary for adenoviral replication, preferably at least one early gene, under the transcriptional control of a TRE specifically regulated by binding of transcriptional factor(s) and/or co-factor(s) necessary for transcription regulated by the cell status-specific TRE. By providing for cell status-specific transcription of at least one adenovirus gene required for replication, the invention provides adenovirus vectors that can be used for specific cytotoxic effects due to selective replication and/or selective transcription. This is especially useful in the cancer context, in which targeted cell killing is desirable. This is also useful for targeted cytotoxic effects in other, non-tumor cells, when selective destruction and/or suppression of these cells is desirable. The vectors can also be useful for detecting the presence of cells whose cell status permits function of a cell status-specific TRE in, for example, an appropriate biological (such as clinical) sample. Further, the adenovirus vector(s) can optionally selectively produce one or more proteins of interest in a target cell by using a cell status-specific TRE.

We have found that adenovirus vectors of the invention replicate and/or express an adenoviral gene operably linked to a cell status-specific TRE preferentially in cells whose status permits the function of a cell status-specific TRE. In contrast to previously-described adenoviral vectors designed to replicate preferentially in specific, differentiated cell types, the adenovirus vectors of the present invention comprise regulatory elements that are not cell type-specific. Rather, they confer cell status-specific adenoviral replication and/or cell status-specific expression of an operably linked adenoviral gene and/or transgene.

The adenovirus vectors of the present invention comprise a cell status-specific TRE which is functional in a cell which exhibits a particular physiological (i.e., environmental or metabolic) characteristic which is reversible and/or progressive. The target cell may exhibit an aberrant physiological state, such as low oxygen tension, or may be subjected to an aberrant environmental condition, such as heat or ionizing radiation, in order for the cell-status TRE to function. The replication preference of these vectors is indicated by comparing the level of replication (i.e., titer) in cells in a requisite physiological state or condition (for example, an aberrant physiological state) to the level of replication in cells not exhibiting the requisite physiological state (for example, under normal physiological conditions). Thus, the invention also uses and takes advantage of what has been considered an undesirable aspect of adenoviral vectors, namely, their replication and possibly concomitant immunogenicity. The probability of runaway infection is significantly reduced due to the cell status-specific requirements for viral replication. Without wishing to be bound by any particular theory, the inventors note that production of adenovirus proteins can serve to activate and/or stimulate the immune system, generally and/or specifically toward target cells producing adenoviral proteins, which can be an important consideration in the cancer context, where patients are often moderately to severely immunocompromised.

The adenovirus vectors of the present invention find particular utility in specific treatment regimens, in which the treatment is highly focused toward, for example, a particular cancer which might otherwise be inoperable or untreatable. An important feature of the invention is that the vectors are useful in these treatments regardless of the tissue or cell type of the cancer, and yet their cytotoxicity can be targeted to certain locations.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sanbrook et al., 1989);

"Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

For techniques related to adenovirus, see, inter alia, Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Definitions

As used herein, a "transcription response element" or "transcriptional regulatory element", or "TRE" is a polynucleotide sequence, preferably a DNA sequence, which increases transcription of an operably linked polynucleotide sequence in a host cell that allows that TRE to function. A TRE can comprise an enhancer and/or a promoter.

As used herein, the term "cell status-specific TRE" is one that confers transcriptional activation on an operably linked polynucleotide in a cell which allows a cell status-specific TRE to function, i.e., a cell which exhibits a particular physiological condition, including, but not limited to, an aberrant physiological state. "Cell status" thus refers to a given, or particular, physiological state (or condition) of a cell, which is reversible and/or progressive. The physiological state may be generated internally or externally; for example, it may be a metabolic state (such as low oxygen), or it may be generated due to heat or ionizing radiation. "Cell status" is distinct from a "cell type", which relates to a differentiation state of a cell, which under normal conditions is irreversible. Generally (but not necessarily), as discussed herein, a cell status is embodied in an aberrant physiological state, examples of which are given below.

A "normal cell status" or "normal physiological state" is the status of a cell which exists in normal physiological conditions and which is non-dividing or divides in a regulated manner, i.e., a cell in a normal physiological state.

The terms "aberrant cell status" and "aberrant physiological state", used interchangeably herein, intend a condition of a cell which is a response to, a result of, or is influenced by, an aberrant physiological condition. An aberrant cell status is neither cell type-specific nor tissue type-specific. An aberrant cell status is defined in relation to a cell of the same type which is in a non-dividing/regulated dividing state and under normal physiological conditions.

"Normal physiological conditions" are known to those skilled in the art. These conditions may vary, depending on a cell's location in the body. For example, oxygen tension can vary from tissue to tissue. For in vitro analyses for the purposes of determining whether a TRE is responsive to deviations from normal physiological conditions, these conditions generally include an oxygen concentration of about 20% $O_2$, and a temperature of about 37° C. "Regulated cell division" is a term well understood in the art and refers to the normal mitotic activity of a cell. Those skilled in the art understand that normal mitotic activity varies from cell type to cell type. For example, many terminally differentiated cells in tissues exhibit little or no mitotic activity, while hematopoietic cells are generally mitotically active.

An "aberrant physiological condition" or "aberrant physiological state", as used herein, intends a condition which deviates from normal physiological conditions, and includes, but is not limited to, a physiological condition that is characterized by alterations in oxygen concentration, such as hypoxic conditions; temperatures which deviate from physiological temperatures; a condition that triggers apoptosis; radiation, including ionizing radiation and UV irradiation; de-regulated cell division, resulting for example, from a lack of, or insufficient amounts of, or inactivity of, a factor which controls cell division, such as, for example, retinoblastoma protein (Rb); variations in timing of cell cycle; infection with a pathogen; exposure to a chemical substance; or a combination of the above-listed conditions. Another example is a mutation that could, or does, exist in any cell type, i.e., its existence does not depend on, or is not related to, the differentiation state of the cell.

A "target cell", as used herein, is one that permits or induces the function of a cell status-specific TRE such that it effects transcriptional activation of an operably linked polynucleotide. A target cell is one which exhibits a requisite physiological (or environmental) state, which may be an aberrant physiological state. Preferably, a target cell is a mammalian cell, preferably a human cell. A target cell may or may not be neoplastic. By transcriptional activation, it is intended that transcription is increased in the target cell above the levels in a control cell (e.g., a that cell when not exhibiting a requisite physiological state (generally a normal physiological state) by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. The normal levels are generally the level of activity (if any) in a cell as tested under conditions that activate the cell status-specific TRE, or the level of activity (if any) of a reporter construct lacking a cell status-specific TRE as measured in a cell exhibiting the requisite physiological condition.

A "functionally-preserved" variant of a cell status-specific TRE is a cell status-specific TRE which differs from another cell status-specific TRE, but still retains cell status cell-specific transcription activity. The difference in an cell status-specific TRE can be due to differences in linear sequence, arising from, for example, single base mutation(s), addition(s), deletion(s), and/or modification(s) of the bases. The difference can also arise from changes in the sugar(s), and/or linkage(s) between the bases of a cell status-specific TRE.

An "adenovirus vector" or "adenoviral vector" (used interchangeably) comprises a polynucleotide construct of the invention. A polynucleotide construct of this invention may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a nonviral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. A phosphorothiate linkage can be used in place of a phosphodiester linkage. Braun et al. (1988) *J. Immunol.* 141: 2084–9; Latimer et al. (1995) *Mol. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18, Table 7.7.1. A preferred alignment program is ALIGN Plus (Scientific and Educational Software, Pennsylvania), preferably using default parameters.

"Under transcriptional control" is a term well-understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

"Replication" and "propagation" are used interchangeably and refer to the ability of a polynucleotide construct of the invention to reproduce, or proliferate. This term is well understood in the art. For purposes of this invention, replication involves production of adenovirus proteins and is generally directed to reproduction of adenovirus. Replication can be measured using assays standard in the art and described herein, such as a burst assay, plaque assay, or a one-step growth curve assay.

As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, $^3$H-thymidine uptake, and plaque assays.

The term "selective cytotoxicity", as used herein, refers to the cytotoxicity conferred by an adenovirus vector of the present invention on a cell which allows or induces a cell status-specific TRE to function (a target cell) when compared to the cytotoxicity conferred by an adenoviral vector of the present invention on a cell which does not allow a cell status-specific TRE to function (a non-target cell). Such cytotoxicity may be measured, for example, by plaque assays, by reduction or stablization in size of a tumor comprising target cells, or the reduction or stabilization of serum levels of a marker characteristic of the tumor cells, or a tissue-specific marker, e.g., a cancer marker, such as prostate specific antigen.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector. Examples of preferred transgenes are provided below.

In the context of adenovirus, a "heterologous" promoter or enhancer is one which is not associated with or derived from an adenovirus gene.

In the context of adenovirus, an "endogenous" promoter, enhancer, or TRE is native to or derived from adenovirus.

In the context of a cell status-specific TRE, a "heterologous" promoter or enhancer is one which is not normally associated in a cell with or derived from a cell status-specific TRE. Examples of a heterologous promoter or enhancer are the albumin promoter or enhancer and other viral promoters and enhancers, such as SV40, or cell type-specific TREs such as a prostate-specific TRE.

A "cell type-specific TRE" is preferentially functional in a specific type of cell relative to other types of cells. In contrast to cell status, "cell type" is a reflection of a differentiation state of a cell which is irreversible. For example, a prostate-specific antigen is expressed in prostate cells, but is not substantially expressed in other cell types such as hepatocytes, astrocytes, cardiocytes, lymphocytes, etc. Generally, a cell type-specific TRE is active in only one cell type. When a cell type-specific TRE is active in more than one cell type, its activity is restricted to a limited number of cell types, i.e., it is not active in all cell types. A cell type-specific TRE may or may not be tumor cell specific.

"Suppressing" tumor growth indicates a growth state that is curtailed when compared to growth without contact with, i.e., transfection by, an adenoviral vector described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described, herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

An "ADP coding sequence" is a polynucleotide that encodes ADP or a functional fragment thereof. In the context of ADP, a "functional fragment" of ADP is one that exhibits cytotoxic activity, especially cell lysis, with respect to adenoviral replication. Ways to measure cytotoxic activity are known in the art and are described herein.

A polynucleotide that "encodes" an ADP polypeptide is one that can be transcribed and/or translated to produce an ADP polypeptide or a fragment thereof. The anti-sense strand of such a polynucleotide is also said to encode the sequence.

An "ADP polypeptide" is a polypeptide containing at least a portion, or region, of the amino acid sequence of an ADP (see, for example, SEQ ID NO:5), and which displays a function associated with ADP, particularly cytotoxicity, more particularly, cell lysis. As discussed herein, these functions can be measured using techniques known in the art. It is understood that certain sequence variations may be used, due to, for example, conservative amino acid substitutions, which may provide ADP polypeptides.

A polynucleotide sequence that is "depicted in" a SEQ ID NO means that the sequence is present as an identical contiguous sequence in the SEQ ID NO. The term encompasses portions, or regions of the SEQ ID NO as well as the entire sequence contained within the SEQ ID NO.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, rodents, primates, and pets.

An "effective amount" is an amount sufficient to effect beneficial or desired results, which may include clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

Adenoviral Vectors Comprising a Cell Status-Specific TRE

The present invention provides adenoviral vector constructs which comprise an adenovirus gene under transcriptional control of a cell status-specific TRE. Preferably, the adenovirus gene contributes to cytotoxicity (whether direct and/or indirect), more preferably one that contributes to or causes cell death, even more preferably is essential for advenoviral replication. Examples of a gene that contributes to cytotoxicity include, but are not limited to, adenovirus death protein (ADP; discussed below). When the adenovirus vector(s) is selectively (i.e., preferentially) replication competent for propagation in target cells, i.e., cells which permit or induce a cell-status TRE to function, these cells will be preferentially killed upon adenoviral proliferation. Once the target cells are destroyed due to selective cytotoxic and/or cytolytic replication, the adenovirus vector replication is significantly reduced, thus lessening the probability of runaway infection and undesirable bystander effects. In vitro cultures may be retained to monitor the mixture (such as, for example, a biopsy or other appropriate biological sample) for occurrence (i.e., presence) and/or recurrence of the target cell, e.g., a neoplastic cell or other undesired cell. To further ensure cytotoxicity, one or more transgenes having a cytotoxic effect may also be present and under selective transcriptional control. In this embodiment, one may provide higher confidence that the target cells will be destroyed. Additionally, or alternatively, an adenovirus gene that contributes to cytotoxicity and/or cell death (such as ADP) may be included in the adenoviral vector, either free of, or under, selective transcriptional control.

Cell status-specific TREs for use in the adenoviral vectors of the present invention can be derived from any species, preferably a mammal. A number of genes have been described which are expressed in response to, or in association with, a cell status. Any of these cell status-associated genes may be used to generate a cell status-specific TRE.

An example of a cell status is cell cycle. An exemplary gene whose expression is associated with cell cycle is E2F-1, a ubiquitously expressed, growth-regulated gene, which exhibits peak transcriptional activity in S phase. Johnson et al. (1994) *Genes Dev.* 8:1514–1525. The RB protein, as well as other members of the RB family, form specific complexes with E2F-1, thereby inhibiting its ability to activate transcription. Thus, E2F-1-responsive promoters are down-regulated by RB. Many tumor cells have disrupted RB function, which can lead to de-repression of E2F-1-responsive promoters, and, in turn, de-regulated cell division.

Accordingly, in one embodiment, the invention provides an adenoviral vector in which an adenoviral gene (preferably a gene necessary for replication) is under transcriptional control of a cell status-specific TRE, wherein the cell status-specific TRE comprises a cell cycle-activated, or cell-cycle specific, TRE. In one embodiment, the cell cycle-activated TRE is an E2F1 TRE. In one embodiment, this TRE comprises the sequence depicted in FIG. 3 and SEQ ID NO:2.

Another group of genes which are regulated by cell status are those whose expression is increased in response to hypoxic conditions. Bunn and Poyton (1996) *Physiol. Rev.* 76:839–885; Dachs and Stratford (1996) *Br. J. Cancer* 74:5126–5132; Guillemin and Krasnow (1997) *Cell* 89:9–12. Many tumors have insufficient blood supply, due in part to the fact that tumor cells typically grow faster than the endothelial cells that make up the blood vessels, resulting in areas of hypoxia in the tumor. Folkman (1989) *J. Natl Cancerinst.* 82:4–6; and Kallinowski (1996) *The Cancer J.* 9:37–40. An important mediator of hypoxic responses is the transcriptional complex HIF-1, or hypoxia inducible factor-1, which interacts with a hypoxia-responsive element (HRE) in the regulatory regions of several genes, including vascular endothelial growth factor, and several genes encoding glycolytic enzymes, including enolase-1. Murine HRE sequences have been identified and characterized. Firth et al. (1994) *Proc. Natl. Acad. Sci. USA* 91:6496–6500. An HRE from a rat enolase-1 promoter is described in Jiang et al. (1997) *Cancer Res.* 57:5328–5335.

Accordingly, in one embodiment, an adenovirus vector comprises an adenovirus gene, preferably an adenoviral gene essential for replication, under transcriptional control of a cell status-specific TRE comprising an HRE.

Other cell status-specific TREs include heat-inducible (i.e., heat shock) promoters, and promoters responsive to radiation exposure, including ionizing radiation and UV radiation. For example, the promoter region of the early growth response-1 (Egr-1) gene contains an element(s) inducible by ionizing radiation. Hallahan et al. (1995) *Nat. Med.* 1:786–791; and Tsai-Morris et al. (1988) *Nucl. Acids. Res.* 16:8835–8846. Heat-inducible promoters, including heat-inducible elements, have been described. See, for example Welsh (1990) in "Stress Proteins in Biology and Medicine", Morimoto, Tisseres, and Georgopoulos, eds. Cold Spring Harbor Laboratory Press; and Perisic et al. (1989) *Cell* 59:797–806. Accordingly, in some embodiments, the cell status-specific TRE comprises an element(s) responsive to ionizing radiation. In one embodiment, this TRE comprises a 5' flanking sequence of an Egr-1 gene. In other embodiments, the cell status-specific TRE comprises a heat shock responsive, or heat-inducible, element.

A cell status-specific TRE can also comprise multimers. For example, an HRE can comprise a tandem series of at least two, at least three, at least four, or at least five hypoxia-responsive elements. These multimers may also contain heterologous promoter and/or enhancer sequences.

A cell status-specific TRE may or may not lack a silencer. The presence of a silencer (i.e., a negative regulatory element) may assist in shutting off transcription (and thus replication) in non-permissive cells (i.e., cell in a normal cell state). Thus, presence of a silencer may confer enhanced cell status-specific replication by more effectively preventing adenoviral vector replication in non-target cells. Alternatively, lack of a silencer may assist in effecting replication in target cells, thus conferring enhanced cell status-specific replication due to more effective replication in target cells.

In other embodiments, the adenoviral vector comprises an adenoviral gene essential for adenoviral replication under control of a first cell status-specific TRE, and a second adenoviral gene essential for adenoviral replication under control of a second cell status-specific TRE. The first and the second cell status-specific TREs may or may not be identical, and may or may not be substantially identical to one another. By "substantially identical" is meant a requisite degree of sequence identity between the two TREs. The degree of sequence identity between these TREs is at least about 80%, preferably at least about 85%, more preferably at least about 90%, even more preferably at least about 95%, even more preferably at least about 98%, and most preferably 100%. Sequence identity can be determined by a sequence comparison using, i.e., sequence alignment programs that are known in the art, such as those described in *Current Protocols in Molecular Biology* (F. M. Ausubel et al., eds., 1987) Supplement 30, section 7.7.18, Table 7.7.1 A preferred alignment program is ALIGN Plus (Scientific and Educational Software, Pennsylvania), preferably using default parameters. Alternatively, hybridization under stringent conditions can also indicate degree of sequence identity. Stringent conditions are known in the art; an example of a stringent condition is 80° C. (or higher temperature) and 6× SSC (or less concentrated SSC). Other hybridization conditions and parameters (in order of increasing stringency) are: incubation temperatures of 25° C., 37° C., 50° C., and 68° C.; buffer concentrations of 10× SSC, 6× SSC, 1× SSC, 0.1× SSC (where 1× SSC is 0.15 M NaCl and 15 mM citrate buffer) and their equivalents using other buffer systems; formamide concentrations of 0%, 25%, 50%, and 75%; incubation times from about 24 hours about 5 minutes; 1, 2, or more washing steps; wash incubation times of 1, 2, or 15 minutes; and wash solutions of 6× SSC, 1× SSC, 0.1× SSC, or deionized water.

Adenoviral constructs in which the first and second cell status-specific TREs are identical or substantially identical, particularly if these TREs control transcription of early genes (such as E1A and E1B), may display an instability which may be desirable in certain contexts, such as when an automatic "self-destruction" property can shut down the virus, thereby controlling the degree of propagation. Accordingly, in some embodiments, the first and second cell status-specific TRE, or the first and second TRE (one of which is a cell-status-specific TRE) are sufficiently identical to confer instability when compared to two TREs which are less identical with respect to each other (i.e., have more sequence divergence or dissimilarity). Preferred embodiments are those in which the two TREs control E1A and E1B respectively. "Instability" means that the structural integrity of the adenoviral vectors is not preserved as the virus replicates in cells, and can be measured using standard methods in the art, such as Southern analysis. In other embodiments, the first and second TREs are sufficiently divergent and/or placed in the vector such that the vector is stable (i.e., the structural integrity of the adenoviral vector is preserved).

In other embodiments, the adenoviral vector comprises an adenoviral gene essential for adenoviral replication under control of a first cell status-specific TRE, and a transgene under control of a second cell status-specific TRE. The first and the second cell status-specific TREs may or may not be substantially identical to one another.

In some embodiments, a cell status-specific TRE can be juxtaposed with another TRE, such as a different cell status-specific TRE, or, alternatively, a cell type-specific TRE. "Juxtaposed" means a cell status-specific TRE and the second TRE transcriptionally control the same gene, or at least are proximate with respect to the same gene. For these embodiments, the cell status-specific TRE and the second TRE may be in any of a number of configurations, including, but not limited to, (a) next to each other (i.e., abutting); (b) both 5' to the gene that is transcriptionally controlled (i.e., may have intervening sequences between them); (c) one TRE 5' and the other TRE 3' to the gene. For example, as described in Example 1 and shown in FIG. 1, a cell type-specific TRE can be juxtaposed with a cell status-specific TRE to control transcription of an operably linked adenoviral gene. Such "composite" TREs can be used to confer both cell status- and cell type-specific expression of an operably linked polynucleotide, and thus may confer significantly greater specificity and/or efficacy. Examples of cell type-specific TREs are provided below. Alternatively, "composite" TREs can be used to confer different, and possibly synergistic, cell status specificity. For example, a composite TRE could confer specificity to hypoxia and heat shock.

Example 1 provides a description of an adenovirus construct in which a composite TRE upstream of E1A consisting of an HRE and a prostate-specific TRE, PSA-TRE (which consists of enhancer sequences −5322 to −3738 fused to PSA promoter sequence −541 to +12; see U.S. Pat. Nos. 5,871,726; 5,648,478). Accordingly, in some embodiments, the invention provides an adenovirus vector comprising an adenovirus gene essential for replication, preferably an early gene, preferably E1A or E1B, under transcriptional control of a TRE comprising an HRE and a prostate cell specific TRE, preferably comprising a PSA enhancer (preferably −5322 to −3738; or about 503 to about 2086 of SEQ ID NO:3 (bases about 503 to about 2086 of FIG. 4), and a promoter, preferably comprising a PSA enhancer and a PSA promoter (about 5285 to about 5836 of SEQ ID NO:3).

As is readily appreciated by one skilled in the art, a cell status-specific TRE is a polynucleotide sequence, and, as such, can exhibit function over a variety of sequence permutations. Methods of nucleotide substitution, addition, and deletion are known in the art, and readily available functional assays (such as the CAT or luciferase reporter gene assay) allow one of ordinary skill to determine whether a sequence variant exhibits requisite cell status-specific transcription function. Hence, the invention also includes functionally-preserved variants of the nucleic acid sequences disclosed herein, which include nucleic acid substitutions, additions, and/or deletions. While not wishing to be bound by a single theory, the inventors note that it is possible that certain modifications will result in modulated resultant expression levels, including enhanced expression levels. Achievement of modulated resultant expression levels, preferably enhanced expression levels, may be especially desirable in the case of certain, more aggressive forms of cancer, or when a more rapid and/or aggressive pattern of cell killing is warranted (due to an immunocompromised condition of the individual, for example).

As an example of how cell status-specific TRE activity can be determined, a polynucleotide sequence or set of such sequences can be generated using methods known in the art, such as chemical synthesis, site-directed mutagenesis, PCR, and/or recombinant methods. The sequence(s) to be tested is inserted into a vector containing an appropriate reporter gene, including, but not limited to, chloramphenicol acetyl transferase (CAT), β-galactosidase (encoded by the lacZ gene), luciferase (encoded by the luc gene), green fluorescent protein, alkaline phosphatase, and horse radish peroxidase. Such vectors and assays are readily available, from, inter alia, commercial sources. Plasmids thus constructed are transfected into a suitable host cell to test for expression of the reporter gene as controlled by the putative cell status-specific TRE using transfection methods known in the art, such as calcium phosphate precipitation, electroporation, liposomes (lipofection), and DEAE-dextran. Suitable host cells include any cell type, including but not limited to, Hep3B, Hep G2, HuH7, HuH1/C12, LNCaP, HBL-100, Chang liver cells, MCF-7, HLF, HLE, 3T3, HUVEC, and HeLa. Host cells transfected with the TRE-reporter gene construct to be tested are subjected to conditions which result in a change in cell status (for example, one which result in an aberrant physiological state). The same cells not subjected to these conditions, i.e., which are under normal physiological conditions and therefore in a normal physiological state, serve as controls. Results are obtained by measuring the level of expression of the reporter gene using standard assays. Comparison of expression between cells in a particular state and control indicates presence or absence of transcriptional activation. "Transcriptional activation" has been defined above.

Comparisons between or among various cell status-specific TREs can be assessed, for example, by measuring and comparing levels of expression within a single cell line under normal and aberrant physiological conditions. These comparisons may also be made by measuring and comparing levels of expression within a single cell line subjected to reversible environmental conditions (such as heat) and cells not subjected to such conditions. It is understood that absolute transcriptional activity of an cell status-specific TRE will depend on several factors, such as the nature of the target cell, delivery mode and form of the cell status-specific TRE, and the coding sequence that is to be selectively transcriptionally activated. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the cytomegalovirus (CMV) immediate early promoter. This analysis can also indicate negative regulatory regions, i.e., silencers.

As an example of how hypoxia induction can be measured, one can use an assay such as that described in Jiang et al. (1997) *Cancer Research* 57:5328–5335 or Dachs et al. (1997) *Nature Med.* 3:515–520. For example, a construct comprising a putative HRE, or multiple tandem copies thereof, together with a minimal promoter element, operably linked and controlling transcription of a polynucleotide which encodes a protein which is detectable or can be used to give a detectable signal, is introduced into host cells. The host cells are then subjected to conditions of normoxia (e.g., 20% $O_2$), and varying degrees of hypoxia, such as 5%, 2%, 1%, 0.1%, or less, $O_2$. The expression product of the operably linked polynucleotide (reporter gene) is then measured.

Alternatively a putative cell status-specific TRE can be assessed for its ability to confer adenoviral replication preference for cells exhibiting the requisite physiological state, such as heat or ionizing radiation. For this assay, constructs containing an adenovirus gene essential to replication operably linked to a putative cell status-specific TRE are transfected into cells which exhibit the requisite physiological state. Viral replication in those cells is compared, for example, to viral replication by the construct in cells under normal physiological conditions (i.e., not exhibiting the requisite physiological state).

Any of the various serotypes of adenovirus can be used, such as Ad2, Ad5, Ad12 and Ad40. For purposes of illustration, serotype Ad5 will be exemplified herein.

When a cell status-specific TRE is used with an adenovirus gene that is essential for propagation replication competence is preferentially achievable in the target cell expressing cell status. Preferably, the gene is an early gene, such as E1A, E1B, E2, or E4. (E3 is not essential for viral replication.) More preferably, the early gene under cell status-TRE control is E1A and/or E1B. More than one early gene can be placed under control of an cell status-specific TRE. Example 1 provides a more detailed description of such constructs.

The E1A gene is expressed immediately after viral infection (0–2 hours) and before any other viral genes. E1A protein acts as a trans-acting positive-acting transcriptional regulatory factor, and is required for the expression of the other early viral genes E1B, E2, E3, E4, and the promoter-proximal major late genes. Despite the nomenclature, the promoter proximal genes driven by the major late promoter are expressed during early times after Ad5 infection. Flint (1982) *Biochem. Biophys. Acta* 651:175–208; Flint (1986) *Advances Virus Research* 31:169–228; Grand (1987) *Biochem. J.* 241:25–38. In the absence of a functional E1A gene, viral infection does not proceed, because the gene products necessary for viral DNA replication are not produced. Nevins (1989) *Adv. Virus Res.* 31:35–81. The transcription start site of Ad5 E1A is at 498 and the ATG start site of the E1A protein is at 560 in the virus genome.

The E1B protein functions in trans and is necessary for transport of late mRNA from the nucleus to the cytoplasm. Defects in E1B expression result in poor expression of late viral proteins and an inability to shut off host cell protein synthesis. The promoter of E1B has been implicated as the defining element of difference in the host range of Ad40 and Ad5: clinically Ad40 is an enterovirus, whereas Ad5 causes acute conjunctivitis. Bailey, Mackay et al. (1993) *Virology* 193:631; Bailey et al. (1994) *Virology* 202:695–706). The E1B promoter of Ad5 consists of a single high-affinity recognition site for Spl and a TATA box.

The E2 region of adenovirus codes for proteins related to replication of the adenoviral genome, including the 72 kDa DNA-binding protein, the 80 kD precursor terminal protein and the viral DNA polymerase. The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1A transactivator protein, the E2 early promoter is crucial during the early phases of viral replication.

The E2 late promoter overlaps with the coding sequences of a gene encoded by the counterstrand and is therefore not amenable to genetic manipulation. However, the E2 early promoter overlaps only for a few base pairs with sequences coding for a 33 kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor biding sites E2F and ATF. Therefore, insertion of a cell status-TRE having SpeI ends into the SpeI site in the +-strand would disrupt the endogenous E2 early promoter of Ad5 and should allow cell status-restricted expression of E2 transcripts.

The E4 gene has a number of transcription products. The E4 region codes for two polypeptides which are responsible for stimulating the replication of viral genomic DNA and for stimulating late gene expression. The protein products of open reading frames (ORFS) 3 and 6 can both perform these functions by binding the 55 kD protein from E1B and heterodimers of E2F-1 and DP-1. The ORF 6 protein requires interaction with the E1B 55 kD protein for activity while the ORF 3 protein does not. In the absence of functional protein from ORF 3 and ORF 6, plaques are produced with an efficiency less than $10^{-6}$ that of wild type virus. To further restrict viral replication to cells exhibiting a requisite physiological condition or state, E4 ORFs 1–3 can be deleted, making viral DNA replication and late gene synthesis dependent on E4 ORF 6 protein. By combining such a mutant with sequences in which the E1B region is regulated by a cell status-specific TRE, a virus can be obtained in which both the E1B function and E4 function are dependent on a cell status-specific TRE driving E1B.

The major late genes relevant to the subject invention are genes L1, L2, L3, L4, and L5 which encode proteins of the adenovirus virion. All of these genes (typically coding for structural proteins) are probably required for adenoviral replication. The late genes are all under the control of the major late promoter (MLP), which is located in Ad5 at +5986 to +6048.

In addition to conferring selective cytotoxic and/or cytolytic activity by virtue of preferential replication competence in cells exhibiting a requisite physiological state (for example, an aberrant physiological state such as low oxygen conditions), the adenovirus vectors of this invention can further include a heterologous gene (transgene) under the control of a cell status-specific TRE. In this way, various genetic capabilities may be introduced into target cells, particularly cancer cells. For example, in certain instances, it may be desirable to enhance the degree and/or rate of cytotoxic activity, due to, for example, the relatively refractory nature or particular aggressiveness of the cancerous target cell. This could be accomplished by coupling the cell status-specific replicative cytotoxic activity with cell-specific expression of, for example, HSV-tk and/or cytosine deaminase (cd), which renders cells capable of metabolizing 5-fluorocytosine (5-FC) to the chemotherapeutic agent 5-fluorouracil (5-FU). Using these types of transgenes may also confer a bystander effect.

Other desirable transgenes that may be introduced via an adenovirus vector(s) include genes encoding cytotoxic proteins, such as the A chains of diphtheria toxin, ricin or abrin (Palmiter et al. (1987) *Cell* 50: 435; Maxwell et al. (1987) *Mol. Cell. Biol.* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J. Biochem.* 148: 265; Frankel et al. (1989) *Mol. Cell. Biol.* 9: 415), genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly; genes that encode an engineered cytoplasmic variant of a nuclease (e.g. RNase A) or protease (e.g. awsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFN-α, -β, -γ, TNF-α, -β, TGF-α, -β, NGF, and the like. The positive effector genes could be used in an earlier phase, followed by cytotoxic activity due to replication.

In one embodiment, the adenovirus death protein (ADP), encoded within the E3 region, is maintained in the adenovirus vector. The ADP gene, under control of the major late promoter (MLP), appears to code for a protein (ADP) that is important in expediting host cell lysis. Tollefson et al. (1996) *J. Virol.* 70(4):2296; Tollefson et al. (1992) *J. Virol.* 66(6): 3633. Thus, adenoviral vectors containing the ADP gene may render the adenoviral vector more potent, making possible more effective treatment and/or a lower dosage requirement.

Accordingly, the invention provides an adenoviral vector as described herein that further includes a polynucleotide sequence encoding an ADP. A DNA sequence encoding an ADP and the amino acid sequence of an ADP are depicted FIG. 9. Briefly, an ADP coding sequence is obtained preferably from Ad2 (since this is the strain in which ADP has been more fully characterized) using techniques known in the art, such as PCR. Preferably, the Y leader (which is an important sequence for correct expression of late genes) is also obtained and ligated to the ADP coding sequence. The ADP coding sequence (with or without the Y leader) can then be introduced into the adenoviral genome, for example, in the E3 region (where the ADP coding sequence will be driven by the MLP). The ADP coding sequence could also be inserted in other locations of the adenovirus genome, such as the E4 region. Alternatively, the ADP coding sequence could be operably linked to a heterologous promoter (with or without enhancer(s)), including, but not limited to, another viral promoter, a cell status-specific TRE such as a hypoxia responsive element, or a cell type-specific TRE such as those derived from carcinoembryonic antigen (CEA), mucin, and rat probasin genes.

Adenoviral Vectors of the Invention Further Comprising a Cell Type Specific Element In addition to conferring selective cytotoxic and/or cytolytic activity by virtue of preferential replication competence and/or by preferential transcription of a gene encoding a cytotoxic factor in cells exhibiting a requisite physiological state, the adenovirus vectors of this invention can further include an adenovirus gene and/or a heterologous gene (transgene) under the control of a cell type-specific TRE. In this way, cytotoxicity is further limited to a particular cell type.

For example, TREs that function preferentially in prostate cells include, but are not limited to, TREs derived from the prostate-specific antigen gene (PSA-TRE) (U.S. Pat. No. 5,648,478), the glandular kallikrein-1 gene (from the human gene, hKLK2-TRE), and the probasin gene (PB-TRE) (International Patent Application No. PCT/US98/04132). All three of these genes are preferentially expressed in prostate cells and the expression is androgen-inducible. Generally, expression of genes responsive to androgen induction requires the presence of an androgen receptor (AR).

PSA is synthesized exclusively by normal, hyperplastic, and malignant prostatic epithelia; hence, its tissue-specific expression has made it an excellent biomarker for benign prostatic hyperplasia (BPH) and prostatic carcinoma (CaP). Normal serum levels of PSA are typically below 5 ng/ml, with elevated levels indicative of BPH or CaP. Lundwall et al. (1987) *FEBS Lett.* 214: 317; Lundwall (1989) *Biochem. Biophys. Res. Comm.* 161: 1151; and Riegmann et al. (1991) *Molec. Endocrin.* 5:1921.

The region of the PSA gene that is used to provide cell specificity dependent upon androgens, particular in prostate cells, involves approximately 6.0 kilobases. Schuur et al. (1996) *J. Biol. Chem.* 271:7043–7051. An enhancer region of approximately 1.5 kb in humans is located between nt −5322 and nt −3738, relative to the transcription start site of the PSA gene. The PSA promoter consists of the sequence from about nt −540 to nt +12 relative to the transcription start site. Juxtapositioning of these two genetic elements yield a fully functional, minimal prostate-specific enhancer/promoter (PSE) TRE. Other portions of the approximately 6.0 kb region of the PSA gene can be used in the present invention, as long as requisite functionality is maintained. In Example 1, adenoviral vector CN796 is described which comprises a composite TRE comprising an HRE and a PSA-TRE, the PSA-TRE comprising a PSA enhancer from −5322 to −3738 fused to a PSA promoter from −541 to +12. This PSA-TRE is derived from adenoviral vector CN706. Rodriguez et al. (1997) *Cancer Research* 57:2559–2563. Accordingly, in one embodiment an adenoviral vector comprises and adenovirus E1A gene under transcriptional control of a composite TRE comprising the cell status-specific TRE, HRE, and a cell type-specific TRE, a PSA-TRE.

The PSE and PSA TRE used in the present invention are derived from sequences depicted in FIG. 4 (SEQ ID NO:3). The enhancer element is nucleotides about 503 to about 2086 of FIG. 4 (SEQ ID NO:3). The promoter is nucleotides about 5285 to about 5836 of FIG. 4 (SEQ ID NO:3). Accordingly, in some embodiments, the composite TRE comprises an HRE and a PSA-TRE comprises nucleotides about 503 to about 2086 of SEQ ID NO:3. In other embodiments, the composite TRE comprises an HRE and a PSA-TRE comprises nucleotides about 503 to about 2086 of SEQ ID NO:3 and nucleotides about 5285 to about 5836 of SEQ ID NO:3. As described above, these composite (HRE/PSA) TREs may be operably linked to an adenovirus gene essential for replication, especially an early gene such as E1A or E1B. Example 1 describes such a construct.

In the present invention, replication-competent adenovirus vectors comprising a cell status-specific TRE and a cell type-specific TRE may employ cell type-specific TREs that are preferentially functional in particular tumor cells. Non-limiting examples of tumor cell-specific TREs, and non-limiting examples of respective potential target cells, include TREs from the following genes: α-fetoprotein (AFP) (liver cancer), mucin-like glycoprotein DF3 (MUC1) (breast carcinoma), carcinoembryonic antigen (CEA) (colorectal, gastric, pancreatic, breast, and lung cancers), plasminogen activator urokinase (uPA) and its receptor gene (breast, colon, and liver cancers), HER-2/neu (c-erbB2/neu) (breast, ovarian, stomach, and lung cancers).

Other cell type-specific TREs may be derived from the following exemplary genes (cell type in which the TREs are specifically functional are in parentheses): vascular endothelial growth factor receptor (endothelium), albumin (liver), factor VII (liver), fatty acid synthase (liver), von Willebrand factor (brain endothelium), alpha-actin and myosin heavy chain (both in smooth muscle), synthetase I (small intestine), Na—K—Cl transporter (kidney). Additional cell type-specific TREs are known in the art.

AFP is an oncofetal protein, the expression of which is primarily restricted to developing tissues of endodermal origin (yolk sac, fetal liver, and gut), although the level of its expression varies greatly depending on the tissue and the developmental stage. AFP is of clinical interest because the serum concentration of AFP is elevated in a majority of hepatoma patients, with high levels of AFP found in patients with advanced disease. The serum AFP levels in patients appear to be regulated by AFP expression in hepatocellular carcinoma but not in surrounding normal liver. Thus, the AFP gene appears to be regulated to hepatoma cell-specific expression.

Cell type-specific TREs from the AFP gene have been identified. For example, the cloning and characterization of human AFP-specific enhancer activity is described in Watanabe et al. (1987) *J. Biol. Chem.* 262:4812–4818. The entire 5' AFP flanking region (containing the promoter, putative silencer, and enhancer elements) is contained within approximately 5 kb upstream from the transcription start site.

The AFP enhancer region in human is located between about nt –3954 and about nt –3335, relative to the transcription start site of the AFP gene. The human AFP promoter encompasses a region from about nt –174 to about nt +29. Juxtapositioning of these two genetic elements yields a fully functional AFP-TRE. Ido et al. (1995) describe a 259 bp promoter fragment (nt –230 to nt +29) that is specific for HCC. *Cancer Res.* 55:3105–3109. The AFP enhancer contains two regions, denoted A and B, located between nt –3954 and nt –3335 relative to the transcription start site. The promoter region contains typical TATA and CAAT boxes. Preferably, the AFP-TRE contains at least one enhancer region. More preferably, the AFP-TRE contains both enhancer regions.

Suitable target cells for adenoviral vectors containing AFP-TREs are any cell type that allow an AFP-TRE to function. Preferred are cells that express, or produce, AFP, including, but not limited to, tumor cells expressing AFP. Examples of such cells are hepatocellular carcinoma cells, gonadal and other germ cell tumors (especially endodermal sinus tumors), brain tumor cells, ovarian tumor cells, acinar cell carcinoma of the pancreas (Kawanoto et al. (1992) *Hepatogastroenterology* 39:282–286), primary gall bladder tumor (Katsuragi et al. (1989) *Rinsko Hoshasen* 34:371–374), uterine endometrial adenocarcinoma cells (Koyama et al. (1996) *Jpn. J. Cancer Res.* 87:612–617), and any metastases of the foregoing (which can occur in lung, adrenal gland, bone marrow, and/or spleen). In some cases, metastatic disease to the liver from certain pancreatic and stomach cancers produce AFP. Especially preferred are hepatocellular carcinoma cells and any of their metastases. AFP production can be measured using assays standard in the art, such as RIA, ELISA or Western blots (immunoassays) to determine levels of AFP protein production or Northern blots to determine levels of AFP mRNA production. Alternatively, such cells can be identified and/or characterized by their ability to activate transcriptionally an AFP-TRE (i.e., allow an AFP-TRE to function).

The protein urokinase plasminogen activator (uPA) and its cell surface receptor, urokinase plasminogen activator receptor (uPAR), are expressed in many of the most frequently occurring neoplasia and appear to represent important proteins in cancer metastasis. Both proteins are implicated in breast, colon, prostate, liver, renal, lung and ovarian cancer. Transcriptional regulatory elements that regulate uPA and uPAR transcription have been extensively studied. Riccio et al. (1985) *Nucleic Acids Res.* 13:2759–2771; Cannio et al. (1991) *Nucleic Acids Res.* 19:2303–2308.

CEA is a 180,000-Dalton glycoprotein tumor-associated antigen present on endodermally-derived neoplasia of the gastrointestinal tract, such as colorectal, gastric (stomach) and pancreatic cancer, as well as other adenocarcinomas such as breast and lung cancers. CEA is of clinical interest because circulating CEA can be detected in the great majority of patients with CEA-positive tumors. In lung cancer, about 50% of total cases have circulating CEA, with high concentrations of CEA (greater than 20 ng/ml) often detected in adenocarcinomas. Approximately 50% of patients with gastric carcinoma are serologically positive for CEA.

The 5' upstream flanking sequence of the CEA gene has been shown to confer cell-specific activity. The CEA promoter region, approximately the first 424 nucleotides upstream of the translational start site in the 5' flanking region of the gene, was shown to confer cell-specific activity when the region provided higher promoter activity in CEA-producing cells than in non-producing HeLa cells. Schrewe et al. (1990) *Mol. Cell. Biol.* 10:2738–2748. In addition, cell-specific enhancer regions have been found. WO/95/14100. The entire 5' CEA flanking region (containing the promoter, putative silencer, and enhancer elements) appears to be contained within approximately 14.5 kb upstream from the transcription start site. Richards et al. (1995); WO 95/14100. Further characterization of the 5' flanking region of the CEA gene by Richards et al. (1995) indicated two upstream regions, –13.6 to –10.7 kb or –6.1 to –4.0 kb, when linked to the multimerized promoter resulted in high-level and selective expression of a reporter construct in CEA-producing LoVo and SW1463 cells. Richards et al. (1995) also localized the promoter region to nt –90 and nt +69 relative to the transcriptional start site, with region nt –41 to nt –18 as essential for expression. WO95/14100 describes a series of 5' flanking CEA fragments which confer cell-specific activity, such as about nt –299 to about nt +69; about nt –90 to about nt +69; nt –14,500 to nt –10,600; nt –13,600 to nt –10,600, nt –6100 to nt –3800. In addition, cell specific transcription activity is conferred on an operably linked gene by the CEA fragment from nt –402 to nt +69, depicted in (SEQ ID NO:6). Any CEA-TREs used in the present invention are derived from mammalian cells, including but not limited to, human cells. Thus, any of the CEA-TREs may be used in the invention as long as requisite desired functionality is displayed in the adenovirus vector. The cloning and characterization of CEA sequences have been described in the literature and are thus made available for practice of this invention and need not be described in detail herein.

The protein product of the MUC1 gene (known as mucin or MUC1 protein; episialin; polymorphic epithelial mucin or PEM; EMA; DF3 antigen; NPGP; PAS-O; or CA15.3 antigen) is normally expressed mainly at the apical surface of epithelial cells lining the glands or ducts of the stomach, pancreas, lungs, trachea, kidney, uterus, salivary glands, and mammary glands. Zotter et al. (1988) *Cancer Rev.* 11–12: 55–101; and Girling et al. (1989) *Int. J. Cancer* 43: 1072–1076. However, mucin is overexpressed in 75–90% of human breast carcinomas. Kufe et al. (1984) *Hybridoma* 3: 223–232. For reviews, see Hilkens (1988) *Cancer Rev.* 11–12: 25–54; and Taylor-Papadimitriou, et al. (1990) *J. Nucl. Med. Allied Sci.* 34: 144–150. Mucin protein expression correlates with the degree of breast tumor differentiation. Lundy et al. (1985) *Breast Cancer Res. Treat.* 5: 269–276. This overexpression appears to be controlled at the transcriptional level.

Overexpression of the MUC1 gene in human breast carcinoma cells MCF-7 and ZR-75-1 appears to be regulated at the transcriptional level. Kufe et al. (1984); *Kovarik* (1993) *J. Biol. Chem.* 268:9917–9926; and Abe et al. (1990) *J. Cell. Physiol.* 143: 226–231. The regulatory sequences of the MUC1 gene have been cloned, including the approximately 0.9 kb upstream of the transcription start site which contains a TRE that appears to be involved in cell-specific transcription. Abe et al. (1993) *Proc. Natl. Acad. Sci. USA* 90: 282–286; Kovarik et al. (1993); and Kovarik et al. (1996) *J. Biol. Chem.* 271:18140–18147.

Any MUC1-TREs used in the present invention are derived from mammalian cells, including but not limited to, human cells. Preferably, the MUC1-TRE is human. In one embodiment, the MUC1-TRE may contain the entire 0.9 kb 5' flanking sequence of the MUC1 gene. In other embodiments, the MUC1-TREs comprise the following sequences (relative to the transcription start site of the MUC1 gene): about nt −725 to about nt +31, nt −743 to about nt +33, nt −750 to about nt +33, and nt −598 to about nt +485 (operably-linked to a promoter).

The c-erbB2/neu gene (HER-2/neu or HER) is a transforming gene that encodes a 185 kD epidermal growth factor receptor-related transmembrane glycoprotein. In humans, the c-erbB2/neu protein is expressed during fetal development, however, in adults, the protein is weakly detectable (by immunohistochemistry) in the epithelium of many normal tissues. Amplification and/or over-expression of the c-erbB2/neu gene has been associated with many human cancers, including breast, ovarian, uterine, prostate, stomach and lung cancers. The clinical consequences of the c-erbB2/neu protein over-expression have been best studied in breast and ovarian cancer. c-erbB2/neu protein over-expression occurs in 20 to 40% of intraductal carcinomas of the breast and 30% of ovarian cancers, and is associated with a poor prognosis in subcategories of both diseases. Human, rat and mouse c-erbB2/neu TREs have been identified and shown to confer c-erbB2/neu expressing cell specific activity. Tal et al. (1987) *Mol. Cell. Biol.* 7:2597–2601; Hudson et al. (1990) *J. Biol. Chem.* 265:43894393; Grooteclaes et al. (1994) *Cancer Res.* 54:41934199; Ishii et al. (1987) *Proc. Natl. Acad. Sci. USA* 84:4374–4378; Scott et al. (1994) *J. Biol. Chem.* 269:19848–19858.

The cell type-specific TREs listed above are provided as non-limiting examples of TREs that would function in the instant invention. Additional cell-specific TREs are known in the art, as are methods to identify and test cell specificity of suspected TREs.

Using the Adenoviral Vectors of the Invention

The adenoviral vectors can be used in a variety of forms, including, but not limited to, naked polynucleotide (usually DNA) constructs; polynucleotide constructs complexed with agents to facilitate entry into cells, such as cationic liposomes or other cationic compounds such as polylysine; packaged into infectious adenovirus particles (which may render the adenoviral vector(s) more immunogenic); packaged into other particulate viral forms such as HSV or AAV; complexed with agents (such as PEG) to enhance or dampen an immune response; complexed with agents that facilitate in vivo transfection, such as DOTMA™, DOTAP™, and polyamines. Thus, the invention also provides an adenovirus capable of replicating preferentially in cell status-producing cells. "Replicating preferentially" means that the adenovirus replicates more in cell exhibting a requisite physiological state than a cell not exhbiting that state. Preferably, the adenovirus replicates at least about 2-fold higher, preferably at least about 5-fold higher, more preferably at least about 10-fold higher, still more preferably at least about 50-fold higher, even more preferably at least about 100-fold higher, still more preferably at least about 400-fold to about 500-fold higher, still more preferably at least about 1000-fold higher, most preferably at least about $1 \times 10^6$ higher. Most preferably, the adenovirus replicates solely in cells exhibiting a requisite physiological state (that is, does not replicate or replicates at very low levels in cells not exhibiting the requisite physiological state).

If an adenoviral vector is packaged into an adenovirus, the adenovirus itself may also be selected to further enhance targeting. For example, adenovirus fibers mediate primary contact with cellular receptor(s) aiding in tropism. See, e.g., Amberg et al. (1997) *Virol.* 227:239–244. If a particular subgenus of an adenovirus serotype displayed tropism for a target cell type and/or reduced affinity for non-target cell types, such subgenus (or subgenera) could be used to further increase cell-specificity of cytoxicity and/or cytolysis.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are in vitro or in vivo).

If used as a packaged adenovirus, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 μg to about 1000 μg of an adenoviral vector can be administered. The adenoviral vector(s) may be administered one or more times, depending upon the intended use and the immune response potential of the host, and may also be administered as multiple, simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

Host Cells Comprising the Adenoviral Vectors of the Invention

The present invention also provides host cells comprising (i.e., transformed with) the adenoviral vectors described herein. Both prokaryotic and eukaryotic host cells can be used as long as sequences requisite for maintenance in that host, such as appropriate replication origin(s), are present. For convenience, selectable markers are also provided. Prokaryotic host cells include bacterial cells, for example, *E. coli* and mycobacteria. Among eukaryotic host cells are yeast, insect, avian, plant and mammalian. Host systems are known in the art and need not be described in detail herein.

Compositions of the Invention

The present invention also provides compositions, including pharmaceutical compositions, containing the adenoviral vectors described herein. Such compositions (especially pharmaceutical compositions) are useful for administration in vivo, for example, when measuring the degree of transduction and/or effectiveness of cell killing in an individual. Pharmaceutical compositions, comprised an adenoviral vector of this invention in a pharmaceutically acceptable excipient (generally an effective amount of the adenoviral vector), are suitable for systemic administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in *Reming-* ton's *Pharmaceutical Sciences,* 19th Edition, Mack Publishing (1995). Pharmaceutical compositions also include lyophilized and/or reconstituted forms of the adenoviral vectors (including those packaged as a virus, such as adenovirus) of the invention.

Other compositions are used, and are useful for, detection methods described herein. For these compositions, the adenoviral vector usually is suspended in an appropriate solvent or solution, such as a buffer system. Such solvent systems are well known in the art.

Kits of the Invention

The present invention also encompasses kits containing an adenoviral vector(s) of this invention. These kits can be used for diagnostic and/or monitoring purposes, preferably monitoring. Procedures using these kits can be performed by clinical laboratories, experimental laboratories, medical practitioners, or private individuals. Kits embodied by this invention allow someone to detect the presence of cell status-producing cells in a suitable biological sample, such as biopsy specimens.

The kits of the invention comprise an adenoviral vector described herein in suitable packaging. The kit may optionally provide additional components that are useful in the procedure, including, but not limited to, buffers, developing reagents, labels, reacting surfaces, means for detection, control samples, instructions, and interpretive information.

Preparation of the Adenovirus Vectors of the Invention

The adenovirus vectors of this invention can be prepared using recombinant techniques that are standard in the art. Generally, a cell status-specific TRE is inserted 5' to the adenoviral gene of interest, preferably one or more early genes (although late gene(s) may be used). A cell status-specific TRE can be prepared using oligonucleotide synthesis (if the sequence is known) or recombinant methods (such as PCR and/or restriction enzymes). Convenient restriction sites, either in the natural adeno-DNA sequence or introduced by methods such as oligonucleotide directed mutagenesis and PCR, provide an insertion site for a cell status-specific TRE. Accordingly, convenient restriction sites for annealing (i.e., inserting) a cell status-specific TRE can be engineered onto the 5' and 3' ends of a cell status-specific TRE using standard recombinant methods, such as PCR Polynucleotides used for making adenoviral vectors of this invention may be obtained using standard methods in the art, such as chemical synthesis, by recombinant methods, and/or by obtaining the desired sequence(s) from biological sources.

Adenoviral vectors are conveniently prepared by employing two plasmids, one plasmid providing for the left hand region of adenovirus and the other plasmid providing for the right hand region, where the two plasmids share at least about 500 nt of middle region for homologous recombination. In this way, each plasmid, as desired, may be independently manipulated, followed by cotransfection in a competent host, providing complementing genes as appropriate, or the appropriate transcription factors for initiation of transcription from a cell status-specific TRE for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can also be used to construct recombinant adenovirus derivative containing all the replication-essential portions of adenovirus genome. Berkner et al. (1983) *Nucleic Acid Research* 11: 6003–6020; Bridge et al. (1989) *J. Virol.* 63: 631–638.

For convenience, plasmids are available that provide the necessary portions of adenovirus. Plasmid pXC.1 (McKinnon (1982) *Gene* 19:33–42) contains the wild-type left-hand end of Ad5. pBHG10 (Bett et al. (1994) *Proc. Natl. Acad. Sci USA* 91:8802–8806; Microbix Biosystems Inc., Toronto) provides the right-hand end of Ad5, with a deletion in E3. The deletion in E3 provides room in the virus to insert a 3 kb cell status-TRE without deleting the endogenous enhancer/promoter. Bett et al. (1994). The gene for E3 is located on the opposite strand from E4 (r-strand). pBHG11 provides an even larger E3 deletion (an additional 0.3 kb is deleted). Bett et al. (1994).

For manipulation of the early genes, the transcription start site of Ad5 E1A is at 498 and the ATG start site of the E1A protein is at 560 in the virus genome. This region can be used for insertion of an cell status-specific TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at 1339 of Ad5. By carrying out the PCR in two steps, where overlapping primers at the center of the region introduce a 30 sequence change resulting in a unique restriction site, one can provide for insertion of heterologous TRE at that site.

A similar strategy may also be used for insertion of a heterologous TRE to regulate E1B. The E1B promoter of Ad5 consists of a single high-affinity recognition site for Sp1 and a TATA box. This region extends from 1636 to 1701. By insertion of a heterologous TRE in this region, one can provide for target cell-specific transcription of the E1B gene. By employing the left-hand region modified with a heterologous TRE regulating E1A as the template for introducing a heterologous TRE to regulate E1B, the resulting adenovirus vector will be dependent upon the cell status-specific transcription factors for expression of both E1A and E1B.

Similarly, a cell status-specific TRE can be inserted upstream of the E2 gene to make its expression cell status specific. The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site. For a detailed review of the E2 promoter architecture see Swaminathan et al., *Curr. Topics in Micro. and Imm.* (1995) 199 (part 3):177–194.

For E4, one must use the right hand portion of the adenovirus genome. The E4 transcription start site is predominantly at 35609, the TATA box at 35638 and the first ATG/CTG of ORF 1 is at 35532. Virtanen et al. (1984) *J. Virol.* 51: 822–831. Using any of the above strategies for the other genes, a cell status-specific TRE may be introduced upstream from the transcription start site. For the construction of mutants in the E4 region, the co-transfection and homologous recombination are performed in W162 cells (Weinberg et al. (1983) *Proc. Natl. Acad. Sci.* 80:5383–5386) which provide E4 proteins in trans to complement defects in synthesis of these proteins. Alternatively, these constructs can be produced by in vitro ligation.

Methods Using the Adenovirus Vectors of the Invention

The adenoviral vectors of the invention can be used for a wide variety of purposes, which will vary with the desired or intended result. Accordingly, the present invention includes methods using the adenoviral vectors described above.

In one embodiment, methods are provided for conferring selective cytotoxicity in target cells (i.e., cells exhibiting a requisite physiological state which allows a cell status-specific TRE to function), generally but not necessarily in an individual (preferably human), comprising contacting the cells with an adenovirus vector described herein, such that the adenovirus vector enters the cell. Cytotoxicity can be measured using standard assays in the art, such as dye exclusion, $^3$H-thymidine incorporation, and/or lysis.

In another embodiment, methods are provided for propagating an adenovirus specific for mammalian cells which allow a cell status-specific TRE to function. These methods entail combining an adenovirus vector with mammalian cells, whereby said adenovirus is propagated.

The invention further provides methods of suppressing tumor cell growth, generally but not necessarily in an individual (preferably human), comprising contacting a tumor cell with an adenoviral vector of the invention such that the adenoviral vector enters the tumor cell and exhibits selective cytotoxicity for the tumor cell. Tumor cell growth can be assessed by any means known in the art, including, but not limited to, measuring tumor size, determining whether tumor cells are proliferating using a H-thymidine incorporation assay, or counting tumor cells.

The invention also includes methods for detecting target cells (i.e., cells which permit or induce a cell status-specific TRE to function) in a biological sample. These methods are particularly useful for monitoring the clinical and/or physiological condition of an individual (i.e., mammal), whether in an experimental or clinical setting. For these methods, cells of a biological sample are contacted with an adenovirus vector, and replication of the adenoviral vector is detected. A suitable biological sample is one in which cells exhibiting a requisite physiological (and/or environmental) state, for example, an aberrant physiological state (such as cells in hypoxic conditions and exhibiting a phenotype characteristic of cells in hypoxic conditions, such as expression of HIF-1) may be or are suspected to be present. Generally, in mammals, a suitable clinical sample is one in which cancerous cells exhbiting a requisite physiological state, such as cells within a solid tumor which are under hypoxic conditions, are suspected to be present. Such cells can be obtained, for example, by needle biopsy or other surgical procedure. Cells to be contacted may be treated to promote assay conditions, such as selective enrichment, and/or solubilization. In these methods, target cells can be detected using in vitro assays that detect adenoviral proliferation, which are standard in the art. Examples of such standard assays include, but are not limited to, burst assays (which measure virus yield) and plaque assays (which measure infectious particles per cell). Propagation can also be detected by measuring specific adenoviral DNA replication, which are also standard assays.

The following examples are provided to illustrate but not limit the invention.

EXAMPLES

Example 1
Adenovirus Vector Comprising E1A Under Transcriptional Control of a Hypoxia Responsive Element and a PSA-TRE
General Techniques A human embryonic kidney cell line, 293, efficiently expresses E1A and E1B genes of Ad5 and exhibits a high transfection efficiency with adenovirus DNA. To generate recombinant adenovirus, 293 cells were co-transfected with one left end Ad5 plasmid and one right end Ad5 plasmid. Homologous recombination generates adenoviruses with the required genetic elements for replication in 293 cells which provide E1A and E1B proteins in trans to complement defects in synthesis of these proteins.

The plasmids to be combined were co-transfected into 293 cells using cationic liposomes such as Lipofectin (DOTMA:DOPE™, Life Technologies) by combining the two plasmids, then mixing the plasmid DNA solution (10 μg of each plasmid in 500 μl of minimum essential medium (MEM) without serum or other additives) with a four-fold molar excess of liposomes in 200 μl of the same buffer. The DNA-lipid complexes were then placed on the cells and incubated at 37° C., 5% $CO_2$ for 16 hours. After incubation the medium was changed to MEM with 10% fetal bovine serum and the cells are further incubated at 37° C., 5% $CO_2$, for 10 days with two changes of medium. At the end of this time the cells and medium were transferred to tubes, freeze-thawed three times, and the lysate was used to infect 293 cells at the proper dilution to detect individual viruses as plaques.

Plaques obtained were plaque purified twice, and viruses were characterized for presence of desired sequences by PCR and occasionally by DNA sequencing. For further experimentation, the viruses were purified on a large scale by cesium chloride gradient centrifugation.

Adenovirus Vectors in which E1A is Under Transcriptional Control of a Cell Status-Specific TRE An adenovirus vector containing a hypoxia response element (HRE) was generated. CN796, an adenovirus vector in which E1A is under the control of a composite TRE consisting of an HRE and a PSA-TRE, was made by co-transfecting CN515 with pBHG10. CN515 was constructed by inserting a 67 base pair fragment from HRE enol (Jiang et al. (1997) *Cancer Research* 57:5328–5335) into CN65 at the BglII site. CN65 is a plasmid containing an enhancer and promoter from the human PSA gene, consisting of an enhancer from −5322 to −3738 fused to a PSA promoter from −541 to +12. This is the PSA-TRE contained within plasmid CN706. Rodriguez et al. (1997) *Cancer Res.* 57:2559–2563.

Virus growth in vitro

Growth selectivity of recombinant adenovirus is analyzed in plaque assays in which a single infectious particle produces a visible plaque by multiple rounds of infection and replication. Virus stocks are diluted to equal pfu/ml, then used to infect monolayers of cells for 1 hour. The inoculum is then removed and the cells are overlayed with semisolid agar containing medium and incubated at 37° C. for 10 days. Plaques in the monolayer are then counted and titers of infectious virus on the various cells are calculated. The data are normalized to the titer of CN702 (wild type) on 293 cells.

What is claimed is:

1. A replication-competent adenovirus vector for selective cytolysis of a target cell comprising,
a hypoxia responsive element (HRE) operably linked to an adenovirus gene essential for replication selected from the group consisting of E1A, E1B and E4, wherein said HRE comprises a binding site for hypoxia inducible factor-1 is activated and the vector effects selective cytolysis of said target cell under hypoxic conditions.

2. The adenovirus vector of claim 1, wherein the HRE is human.

3. The adenovirus vector of claim 1, wherein said adenovirus gene essential for replication is operably linked to a composite regulatory element comprising said HRE and a tumor cell-specific transcriptional regulatory element (TRE).

4. The adenovirus vector of claim 3, wherein said tumor cell-specific TRE comprises a promoter.

5. The adenovirus vector of claim 3, wherein said tumor cell-specific TRE comprises an enhancer.

6. The adenovirus vector of claim 3, wherein said tumor cell-specific TRE comprises a prostate specific promoter and enhancer.

7. The adenovirus vector of claim 3, wherein said tumor cell-specific transcriptional regulatory element (TRE) is selected from the group consisting of a prostate-specific TRE (PSA-TRE), a glandular kallikrein-1 TRE (hKLK2-TRE), a probasin TRE (PB-TRE), an α-fetoprotein TRE (AFP TRE) and a carcinoembryonic antigen TRE (CEA TRE).

8. A composition comprising:
a replication-competent adenovirus vector of claim 1 and a pharmaceutically acceptable excipient.

9. An isolated host cell comprising the adenovirus vector of claim 1.

10. A method of propagating adenovirus in vitro, the method comprising:
introducing into a cell an adenovirus vector comprising a hypoxia responsive element (HRE) operably linked to an adenovirus gene essential for replication selected from the group consisting of E1A, E1B and E4, wherein said HRE comprises a binding site for hypoxia inducible factor-1 wherein said cell is maintained under hypoxic conditions in vitro, thereby expressing said adenovirus gene essential for replication;
wherein said adenovirus is propagated.

11. The method of claim 10, wherein said propagating of said adenovirus is cytotoxic to said cell.

12. The method of claim 11, wherein said cell is a tumor cell.

13. A replication-competent adenovirus vector for selective cytolysis of a target cell with a disrupted RB function, comprising:
an E2F-1 transcriptional regulatory element (TRE) operably linked to an adenovirus gene essential for replication selected from the group consisting of E1A, E1B and E4, wherein said vector effects selective cytolysis due to selective replication in a target cell with disrupted RB function.

14. The adenovirus vector of claim 13, wherein the E2F-1 TRE is human.

15. The adenovirus vector of claim 14, wherein said E2F-1 TRE comprises the nucleotide sequence set forth in SEQ ID NO:2.

16. The adenovirus vector of claim 13, wherein said E2F-1 TRE comprises a nucleotide sequence having at least 80% sequence identity with the sequence set forth in SEQ ID NO:2.

17. The adenovirus vector of claim 13, wherein said adenovirus gene essential for replication is operably linked to a composite regulatory element comprising said E2F-1 transcriptional regulatory element and a cell-type specific transcriptional regulatory element (TRE).

18. The adenovirus vector of claim 17, wherein said tumor cell-specific transcriptional regulatory element (TRE) is selected from the group consisting of a prostate-specific TRE (PSA-TRE), a glandular kallikrein-1 TRE (hKLK2-TRE), a probasin TRE (PB-TRE), an α-fetoprotein TRE (AFP TRE) and a carcinoembryonic antigen TRE (CEA TRE).

19. A composition comprising:
a replication competent adenovirus vector of claim 13 and a pharmaceutically acceptable excipient.

20. An isolated host cell comprising the adenovirus vector of claim 13.

21. A method of propagating adenovirus in vitro, the method comprising:

a replication competent adenovirus vector for selective cytolysis of a target cell, comprising an E2F-1 transcriptional regulatory element (TRE) operably linked to an adenovirus gene essential for replication selected from the group consisting of E1A, E1B and E4 wherein said cell is maintained under cell cycling conditions in vitro, thereby expressing said adenovirus gene essential for replication;

wherein said adenovirus is propagated.

22. The method of claim 21, wherein said propagating of said adenovirus is cytotoxic to said cell.

23. The method of claim 21, wherein said cell is a tumor cell.

24. A replication-competent adenovirus vector for selective cytolysis of a target cell comprising, a hypoxia responsive element (HRE) comprising a binding site for hypoxia inducible factor-1 operably linked to a first adenovirus gene essential for replication and a transcriptional regulatory element (TRE) comprising a heterologous promoter or enhancer operably linked to a second adenoviral gene essential for replication wherein said first and second adenoviral genes essential for replication are selected from the group consisting of E1A, E1B and E4 wherein said adenovirus vector results in cytolysis due to selective replication in a target cell in which a hypoxia inducible factor-1 is present.

25. The replication-competent adenovirus vector of claim 24, wherein said transcriptional regulatory element (TRE) linked to said second adenoviral gene essential for replication is a cell status-specific transcriptional regulatory element (TRE).

26. The replication-competent adenovirus vector of claim 24, wherein said transcriptional regulatory element (TRE) linked to said second adenoviral gene essential for replication is a cell type-specific transcriptional regulatory element (TRE).

27. A replication-competent adenovirus vector for selective cytolysis of a target cell, comprising an E2F-1 transcriptional regulatory element (TRE) operably linked to a first adenovirus gene essential for replication and a transcriptional regulatory element (TRE) comprising a heterologous promoter or enhancer operably linked to a second adenoviral gene essential for replication wherein said first and second adenoviral genes essential for replication are selected from the group consisting of E1A, E1B and E4 wherein said adenovirus vector results in cytolysis due to selective replication in a target cell in which RB function is disrupted.

28. The replication-competent adenovirus vector of claim 27, wherein said transcriptional regulatory element (TRE) linked to said second adenoviral gene essential for replication is a cell status-specific transcriptional regulatory element (TRE).

29. The replication-competent adenovirus vector of claim 27, wherein said transcriptional regulatory element (TRE) linked to said second adenoviral gene essential for replication is a cell type-specific transcriptional regulatory element (TRE).

30. A replication-competent adenovirus vector for selective cytolysis of a target cell comprising, a hypoxia responsive element (HRE) operably linked to an adenovirus gene essential for replication selected from the group consisting of E1A, E1B and E4, wherein said HRE comprises a binding site for hypoxia inducible factor-1 wherein target cell, said adenovirus vector results in cytolysis due to selective replication in a tumor cell in which a hypoxia inducible factor-1 is present.

31. A replication-competent adenovirus vector for selective cytolysis of a tumor target cell, comprising:

an E2F-1 transcriptional regulatory element (TRE) operably linked to an adenovirus gene essential for replication selected from the group consisting of E1A, E1B and E4 wherein said adenovirus vector results in cytolysis due to selective replication in a tumor target cell to which E2F-1 is present.

* * * * *

SEQUENCE LISTING

<160> NUMBER OF SEQ ID NOS: 8

<210> SEQ ID NO 1
<211> LENGTH: 1519
<212> TYPE: DNA
<213> ORGANISM: H. sapiens

<400> SEQUENCE: 1

| | | | | | |
|---|---|---|---|---|---|
| gggcccaaaa | ttagcaagtg | accacgtggt | tctgaagcca | gtggcctaag | gaccacccctt | 60 |
| gcagaaccgt | ggtctccttg | tcacagtcta | ggcagcctct | ggcttagcct | ctgtttcttt | 120 |
| cataaccttt | ctcagcgcct | gctctgggcc | agaccagtgt | tgggaggagt | cgctactgag | 180 |
| ctcctagatt | ggcaggggag | gcagatggag | aaaaggagtg | tgtgtggtca | gcattggagc | 240 |
| agaggcagca | gtgggcaata | gaggaagtga | gtaaatcctt | gggagggctc | cctagaagtg | 300 |
| atgtgttttc | tttttttgtt | ttagagacag | gatctcgctc | tgtcgcccag | gctggtgtgc | 360 |
| agtggcatga | tcatagctca | ctgcagcctc | gacttctcgg | gctcaagcaa | tcctcccacc | 420 |
| tcagcctccc | aagtagctgg | gactacgggc | acacgccacc | atgcctggct | aattttttgta | 480 |
| tttttttgtag | agatgggtct | tcaccatgtt | gatcaggctg | gtctcgaact | cctgggctca | 540 |
| tgcgatccac | cccgccagct | gattacaggg | attccggtgg | tgagccaccg | cgcccagacg | 600 |
| ccacttcatc | gtattgtaaa | cgtctgttac | ctttctgttc | ccctgtctac | tggactgtga | 660 |
| gctccttagg | gccacgaatt | gaggatgggg | cacagagcaa | gctctccaaa | cgtttgttga | 720 |
| atgagtgagg | gaatgaatga | gttcaagcag | atgctatacg | ttggctgttg | gagattttgg | 780 |
| ctaaaatggg | acttgcagga | aagcccgacg | tcccctcgc | catttccagg | caccgctctt | 840 |
| cagcttgggc | tctgggtgag | cgggataggg | ctgggtgcag | gattaggata | atgtcatggg | 900 |
| tgaggcaagt | tgaggatgga | agaggtggct | gatggctggg | ctgtggaact | gatgatcctg | 960 |
| aaaagaagag | gggacagtct | ctggaaatct | aagctgaggc | tgttgggggc | tacaggttga | 1020 |
| gggtcacgtg | cagaagagag | gctctgttct | gaacctgcac | tatagaaagg | tcagtgggat | 1080 |
| gcggagcgt | cggggcgggg | cggggcctat | gttcccgtgt | ccccacgcct | ccagcagggg | 1140 |
| acgcccgggc | tgggggcggg | gagtcagacc | gcgcctggta | ccatccggac | aaagcctgcg | 1200 |
| cgcgccccgc | cccgccattg | gccgtaccgc | cccgcgccgc | cgcccatcc | cgcccctcgc | 1260 |
| cgccgggtcc | ggcgcgttaa | agccaatagg | aaccgccgcc | gttgttcccg | tcacggccgg | 1320 |
| ggcagccaat | tgtggcggcg | ctcggcggct | cgtggctctt | tcgcggcaaa | aaggatttgg | 1380 |
| cgcgtaaaag | tggccgggac | tttgcaggca | gcggcggccg | ggggcggagc | gggatcgagc | 1440 |
| cctcgccgag | gcctgccgcc | atgggcccgc | gccgccgccg | ccgcctgtca | cccgggccgc | 1500 |
| gcgggccgtg | agcgtcatg | | | | | 1519 |

<210> SEQ ID NO 2
<211> LENGTH: 5836
<212> TYPE: DNA
<213> ORGANISM: H. sapiens

<400> SEQUENCE: 2

| | | | | | |
|---|---|---|---|---|---|
| aagcttctag | ttttcttttc | ccggtgacat | cgtggaaagc | actagcatct | ctaagcaatg | 60 |
| atctgtgaca | atattcacag | tgtaatgcca | tccaggggaac | tcaactgagc | cttgatgtcc | 120 |
| agagattttt | gtgtttttttt | ctgagactga | gtctcgctct | gtgccaggct | ggagtgcagt | 180 |
| ggtgcaacct | tggctcactg | caagctccgc | ctcctgggtt | cacgccattc | tcctgcctca | 240 |
| gcctcctgag | tagctgggac | tacaggcacc | cgccaccacg | cctggctaat | tttttttgtat | 300 |
| ttttagtaga | gatggggttt | cactgtgtta | gccaggatgg | tctcagtctc | ctgacctcgt | 360 |
| gatctgccca | ccttggcctc | ccaaagtgct | gggatgacag | gcgtgagcca | ccgcgcctgg | 420 |
| ccgatatcca | gagattttt | gggggctcc | atcacacaga | catgttgact | gtcttcatgg | 480 |
| ttgactttta | gtatccagcc | cctctagaaa | tctagctgat | atagtgtggc | tcaaaacctt | 540 |

-continued

| | |
|---|---|
| cagcacaaat cacaccgtta gactatctgg tgtgggcccaa accttcaggt gaacaaaggg | 600 |
| actctaatct ggcaggatat tccaaagcat tagagatgac ctcttgcaaa gaaaagaaa | 660 |
| tggaaaagaa aaagaaagaa aggaaaaaaa aaaaaaaaaa gagatgacct ctcaggctct | 720 |
| gagggggaaac gcctgaggtc tttgagcaag gtcagtcctc tgttgcacag tctccctcac | 780 |
| agggtcattg tgacgatcaa atgtggtcac gtgtatgagg caccagcaca tgcctggctc | 840 |
| tggggagtgc cgtgtaagtg tatgcttgca ctgctgaatg cttgggatgt gtcagggatt | 900 |
| atcttcagca cttacagatg ctcatctcat cctcacagca tcactatggg atgggtatta | 960 |
| ctggcctcat tgatggagaa agtggctgt ggctcagaaa gggggggacca ctagaccagg | 1020 |
| gacactctgg atgctgggga ctccagagac catgaccact caccaactgc agagaaatta | 1080 |
| attgtggcct gatgtccctg tcctggagag ggtggaggtg gaccttcact aacctcctac | 1140 |
| cttgaccctc tcttttaggg ctctttctga cctccaccat ggtactagga ccccattgta | 1200 |
| ttctgtaccc tcttgactct atgaccccca ctgcccactg catccagctg ggtcccctcc | 1260 |
| tatctctatt cccagctggc cagtgcagtc tcagtgccca cctgtttgtc agtaactctg | 1320 |
| aaggggctga cattttactg acttgcaaac aaataagcta actttccaga gttttgtgaa | 1380 |
| tgctggcaga gtccatgaga ctcctgagtc agaggcaaag gcttttactg ctcacagctt | 1440 |
| agcagacagc atgaggttca tgttcacatt agtacaccctt gcccccccca aatcttgtag | 1500 |
| ggtgaccaga gcagtctagg tggatgctgt gcagaagggg tttgtgccac tggtgagaaa | 1560 |
| cctgagatta ggaatcctca atcttatact gggacaactt gcaaacctgc tcagcctttg | 1620 |
| tctctgatga agatattatc ttcatgatct tggattgaaa acagacctac tctggaggaa | 1680 |
| catattgtat cgattgtcct tgacagtaaa caaatctgtt gtaagagaca ttatctttat | 1740 |
| tatctaggac agtaagcaag cctggatctg agagagatat catcttgcaa ggatgcctgc | 1800 |
| tttacaaaca tccttgaaac aacaatccag aaaaaaaaag gtgttgctgt ctttgctcag | 1860 |
| aagacacaca gatacgtgac agaaccatgg agaattgcct cccaacgctg ttcagccaga | 1920 |
| gccttccacc cttgtctgca ggacagtctc aacgttccac cattaaatac ttcttctatc | 1980 |
| acatcctgct tctttatgcc taaccaaggt tctaggtccc gatcgactgt gtctggcagc | 2040 |
| actccactgc caaacccaga ataaggcagc gctcaggatc ccgaagggc atggctgggg | 2100 |
| atcagaactt ctgggtttga gtgaggagtg ggtccaccct cttgaatttc aaaggaggaa | 2160 |
| gaggctggat gtgaaggtac tggggagggg aaagtgtcag ttccgaactc ttaggtcaat | 2220 |
| gagggaggag actggtaagg tcccagctcc cgaggtactat atgtgggaat ggcctaagaa | 2280 |
| tctcatatcc tcaggaagaa ggtgctggaa tcctgagggg tagagttctg ggtatatttg | 2340 |
| tggcttaagg ctcttggcc cctgaaggca gaggctggaa ccattaggtc cagggtttgg | 2400 |
| ggtgatagta atgggatctc ttgattcctc aagagtctga ggatcgaggg ttgcccattc | 2460 |
| ttccatcttg ccacctaatc cttactccac ttgagggtat caccagccct tctagctcca | 2520 |
| tgaaggtccc ctgggcaagc acaatctgag catgaaagat gccccagagg ccttgggtgt | 2580 |
| catccactca tcatccagca tcacactctg agggtgtggc cagcaccatg acgtcatgtt | 2640 |
| gctgtgacta tccctgcagc gtgcctctcc agccacctgc caaccgtaga gctgcccatc | 2700 |
| ctcctctggt gggagtggcc tgcatggtgc caggctgagg cctagtgtca gacagggagc | 2760 |
| ctggaatcat agggatccag gactcaaaag tgctagagaa tggccatatg tcaccatcca | 2820 |
| tgaaatctca agggcttctg ggtggagggc acagggacct gaacttatgg tttcccaagt | 2880 |
| ctattgctct cccaagtgag tctcccagat acgaggcact gtgccagcat cagccttatc | 2940 |

```
tccaccacat cttgtaaaag gactacccag ggccctgatg aacaccatgg tgtgtacagg    3000 agtaggggt ggaggcacgg actcctgtga ggtcacagcc aagggagcat catcatgggt    3060
ggggaggagg caatgacag gcttgagaac ggggatgtgg ttgtatttgg ttttctttgg    3120
ttagataaag tgctgggtat aggattgaga gtggagtatg aagaccagtt aggatggagg    3180
atcagattgg agttgggtta gataaagtgc tgggtatagg attgagagtg gagtatgaag    3240
accagttagg atggaggatc agattggagt tgggttagag atggggtaaa attgtgctcc    3300
ggatgagttt gggattgaca ctgtggaggt ggtttgggat ggcatggctt tgggatggaa    3360
atagatttgt tttgatgttg gctcagacat ccttggggat tgaactgggg atgaagctgg    3420
gtttgatttt ggaggtagaa gacgtggaag tagctgtcag atttgacagt ggccatgagt    3480
tttgtttgat ggggaatcaa acaatggggg aagacataag ggttggcttg ttaggttaag    3540
ttgcgttggg ttgatggggt cggggctgtg tataatgcag ttggattggt ttgtattaaa    3600
ttgggttggg tcaggttttg gttgaggatg agttgaggat atgcttgggg acaccggatc    3660
catgaggttc tcactggagt ggagacaaac ttccttttcca ggatgaatcc agggaagcct    3720
taattcacgt gtaggggagg tcaggccact ggctaagtat atccttccac tccagctcta    3780
agatggtctt aaattgtgat tatctatatc cacttctgtc tccctcactg tgcttggagt    3840
ttacctgatc actcaactag aaacagggga agattttatc aaattctttt ttttttttt    3900 ttttttttga gacagagtct cactctgttg cccaggctgg agtgcagtgg cgcagtctcg    3960
gctcactgca acctctgcct cccaggttca agtgattctc ctgcctcagc ctcctgagtt    4020
gctgggatta caggcatgca gcaccatgcc cagctaattt ttgtattttt agtagagatg    4080
gggtttcacc aatgtttgcc aggctggcct cgaactcctg acctggtgat ccacctgcct    4140
cagcctccca aagtgctggg attacaggcg tcagccaccg cgcccagcca ttttgtcaa    4200 attcttgaga cacagctcgg gctggatcaa gtgagctact ctggttttat tgaacagctg    4260
aaataaccaa cttttttggaa attgatgaaa tcttacggag ttaacagtgg aggtaccagg    4320
gctcttaaga gttcccgatt ctcttctgag actacaaatt gtgattttgc atgccaccatt    4380 aatctttttt tttttttttt taaatcgagg tttcagtctc attctatttc ccaggctgga    4440
gttcaatagc gtgatcacag ctcactgtag ccttgaactc ctggccttaa gagattctcc    4500
tgcttcggtc tcccaatagc taagactaca gtagtccacc accatatcca gataattttt    4560 aaatttttttg gggggccggg cacagtggct cacgcctgta atcccaacac catgggaggc    4620
tgagatgggt ggatcacgag gtcaggagtt tgagaccagc ctgaccaaca tggtgaaact    4680
ctgtctctac taaaaaaaaa aaaaatagaa aaattagccg ggcgtggtgg cacacggcac    4740
ctgtaatccc agctactgag gaggctgagg caggagaatc acttgaaccc agaaggcaga    4800
ggttgcaatg agccgagatt gcgccactgc actccagcct gggtgacaga gtgagactct    4860
gtctcaaaaa aaaaaaattt ttttttttt tttgtagaga tggatcttgc tttgtttctc    4920
tggttggcct tgaactcctg gcttcaagtg atcctcctac cttggcctcg gaaagtgttg    4980
ggattacagg cgtgagccac catgactgac ctgtcgttaa tcttgaggta cataaacctg    5040
gctcctaaag gctaaaggct aaatatttgt tggagaaggg gcattggatt tgcatgagg    5100 atgattctga cctgggaggg caggtcagca ggcatctctg ttgcacagat agagtgtaca    5160
ggtctggaga acaaggagtg gggggttatt ggaattccac attgtttgct gcacgttgga    5220
ttttgaaatg ctagggaact ttgggagact catatttctg ggctagagga tctgtggacc    5280
acaagatctt tttatgatga cagtagcaat gtatctgtgg agctggattc tgggttggga    5340
```

| | |
|---|---|
| gtgcaaggaa aagaatgtac taaatgccaa gacatctatt tcaggagcat gaggaataaa | 5400 |
| agttctagtt tctggtctca gagtggtgca gggatcaggg agtctcacaa tctcctgagt | 5460 |
| gctggtgtct tagggcacac tgggtcttgg agtgcaaagg atctaggcac gtgaggcttt | 5520 |
| gtatgaagaa tcgggatcg tacccacccc ctgtttctgt ttcatcctgg gcatgtctcc | 5580 |
| tctgcctttg tccctagat gaagtctcca tgagctacaa gggcctggtg catccagggt | 5640 |
| gatctagtaa ttgcagaaca gcaagtgcta gctctccctc cccttccaca gctctgggtg | 5700 |
| tgggagggg ttgtccagcc tccagcagca tggggagggc cttggtcagc tctgggtgc | 5760 |
| cagcagggca gggcggagt cctggggaat gaaggtttta tagggctcct gggggaggct | 5820 |
| ccccagcccc aagctt | 5836 |

<210> SEQ ID NO 3
<211> LENGTH: 15056
<212> TYPE: DNA
<213> ORGANISM: H. sapiens

<400> SEQUENCE: 3

| | |
|---|---|
| aagctttta gtgctttaga cagtgagctg gtctgtctaa cccaagtgac ctgggctcca | 60 |
| tactcagccc cagaagtgaa gggtgaagct gggtggagcc aaaccaggca agcctaccct | 120 |
| cagggctccc agtggcctga gaaccattgg acccaggacc cattacttct agggtaagga | 180 |
| aggtacaaac accagatcca accatggtct gggggacag ctgtcaaatg cctaaaaata | 240 |
| tacctgggag aggagcaggc aaactatcac tgccccaggt tctctgaaca gaaacagagg | 300 |
| ggcaacccaa agtccaaatc caggtgagca ggtgcaccaa atgcccagag atatgacgag | 360 |
| gcaagaagtg aaggaaccac ccctgcatca aatgttttgc atgggaagga gaaggggtt | 420 |
| gctcatgttc ccaatccagg agaatgcatt tgggatctgc cttcttctca ctccttggtt | 480 |
| agcaagacta gcaaccagg actctggatt tggggaaaga cgtttatttg tggaggccag | 540 |
| tgatgacaat cccacgaggg cctaggtgaa gagggcagga aggctcgaga cactggggac | 600 |
| tgagtgaaaa ccacacccat gatctgcacc acccatggat gctccttcat tgctcacctt | 660 |
| tctgttgata tcagatggcc ccattttctg taccttcaca gaaggacaca ggctagggtc | 720 |
| tgtgcatggc cttcatcccc ggggccatgt gaggacagca ggtgggaaag atcatgggtc | 780 |
| ctcctgggtc ctgcagggcc agaacattca tcacccatac tgacctccta gatgggaatg | 840 |
| gcttccctgg ggctgggcca acggggcctg gcaggggag aaaggacgtc aggggacagg | 900 |
| gaggaaggt catcgagacc cagcctggaa ggttcttgtc tctgaccatc caggatttac | 960 |
| ttccctgcat ctacctttgg tcatttccc tcagcaatga ccagctctgc ttcctgatct | 1020 |
| cagcctccca ccctggacac agcaccccag tccctgcccc gctgcatcc acccaatacc | 1080 |
| ctgataaccc aggacccatt acttctaggg taaggagggt ccaggagaca gaagctgagg | 1140 |
| aaaggtctga agaagtcaca tctgtcctgg ccagagggga aaaccatca gatgctgaac | 1200 |
| caggagaatg ttgacccagg aaagggaccg aggacccaag aaaggagtca gaccaccagg | 1260 |
| gtttgcctga gaggaaggat caaggccccg agggaaagca gggctggctg catgtgcagg | 1320 |
| acactggtgg ggcatatgtg tcttagattc tccctgaatt cagtgtccct gccatggcca | 1380 |
| gactctctac tcaggcctgg acatgctgaa ataggacaat ggccttgtcc tctctcccca | 1440 |
| ccatttggca agagacataa aggacattcc aggacatgcc ttcctgggag gtccaggttc | 1500 |
| tctgtctcac acctcaggga ctgtagttac tgcatcagcc atggtaggtg ctgatctcac | 1560 |
| ccagcctgtc caggcccttc cactctccac tttgtgacca tgtccaggac cacccctcag | 1620 |

-continued

```
atcctgagcc tgcaaatacc cccttgctgg gtgggtggat tcagtaaaca gtgagctcct    1680
atccagcccc cagagccacc tctgtcacct tcctgctggg catcatccca ccttcacaag    1740
cactaaagag catggggaga cctggctagc tgggtttctg catcacaaag aaaataatcc    1800
cccaggttcg gattcccagg gctctgtatg tggagctgac agacctgagg ccaggagata    1860
gcagaggtca gccctaggga gggtgggtca tccacccagg ggacagggt gcaccagcct    1920
tgctactgaa agggcctccc caggacagcg ccatcagccc tgcctgagag ctttgctaaa    1980
cagcagtcag aggaggccat ggcagtggct gagctcctgc tccaggcccc aacagaccag    2040
accaacagca caatgcagtc cttccccaac gtcacaggtc accaaaggga aactgaggtg    2100
ctacctaacc ttagagccat caggggagat aacagcccaa tttcccaaac aggccagttt    2160
caatcccatg acaatgacct ctctgctctc attcttccca aaataggacg ctgattctcc    2220
cccaccatgg atttctccct tgtcccggga ccttttctg cccctatga tctgggcact    2280
cctgacacac acctcctctc tggtgacata tcagggtccc tcactgtcaa gcagtccaga    2340
aaggacagaa ccttggacag cgcccatctc agcttcaccc ttcctccttc acagggttca    2400
gggcaaagaa taaatggcag aggccagtga gcccagagat ggtgacaggc agtgacccag    2460
ggcagatgc ctggagcagg agctggcggg gccacaggga gaaggtgatg caggaaggga    2520
aacccagaaa tgggcaggaa aggaggacac aggctctgtg gggctgcagc ccaggggttgg    2580
actatgagtg tgaagccatc tcagcaagta aggccaggtc ccatgaacaa gagtgggagc    2640
acgtggcttc ctgctctgta tatgggtgg gggattccat gccccataga accagatggc    2700
cggggttcag atggagaagg agcaggacag gggatcccca ggataggagg accccagtgt    2760
ccccacccag gcaggtgact gatgaatggg catgcaggt cctcctgggc tgggctctcc    2820
cttttgtccct caggattcct tgaaggaaca tccggaagcc gaccacatct acctggtggg    2880
ttctggggag tccatgtaaa gccaggagct tgtgttgcta ggaggggtca tggcatgtgc    2940
tgggggcacc aaagagagaa acctgagggc aggcaggacc tggtctgagg aggcatggga    3000
gcccagatgg ggagatggat gtcaggaaag gctgccccat cagggagggt gatagcaatg    3060
ggggtctgt gggagtgggc acgtgggatt ccctgggctc tgccaagttc cctcccatag    3120
tcacaacctg gggacactgc ccatgaaggg gcgcctttgc ccagccagat gctgctggtt    3180
ctgcccatcc actaccctct ctgctccagc cactctgggt ctttctccag atgccctgga    3240
cagccctggc ctgggcctgt ccctgagag gtgttgggag aagctgagtc tctggggaca    3300
ctctcatcag agtctgaaag gcacatcagg aaacatccct ggtctccagg actaggcaat    3360
gaggaaaggg ccccagctcc tcccttttgcc actgagaggg tcgaccctgg gtggccacag    3420
tgacttctgc gtctgtccca gtcaccctga accacaaca aaaccccagc ccagaccct    3480
gcaggtacaa tacatgtggg gacagtctgt acccagggga agccagttct ctcttcctag    3540
gagaccgggc ctcagggctg tgcccggggc aggcgggggc agcacgtgcc tgtccttgag    3600
aactcgggac cttaagggtc tctgctctgt gaggcacagc aaggatcctt ctgtccagag    3660
atgaaagcag ctcctgcccc tcctctgacc tcttcctcct tcccaaatct caaccaacaa    3720
ataggtgttt caaatctcat catcaaatct tcatccatcc acatgagaaa gcttaaaacc    3780
caatggattg acaacatcaa gagttggaac aagtggacat ggagatgtta cttgtggaaa    3840
tttagatgtg ttcagctatc gggcaggaga atctgtgtca aattccagca tggttcagaa    3900
gaatcaaaaa gtgtcacagt ccaaatgtgc aacagtgcag gggataaaac tgtggtgcat    3960
tcaaactgag ggatattttg gaacatgaga aaggaaggga ttgctgctgc acagaacatg    4020
```

-continued

```
gatgatctca cacatagagt tgaaagaaag gagtcaatcg cagaatagaa aatgatcact    4080
aattccacct ctataaagtt tccaagagga aaacccaatt ctgctgctag agatcagaat    4140
ggaggtgacc tgtgccttgc aatggctgtg agggtcacgg gagtgtcact tagtgcaggc    4200
aatgtgccgt atcttaatct gggcagggct ttcatgagca cataggaatg cagacattac    4260
tgctgtgttc attttacttc accggaaaag aagaataaaa tcagccgggc gcggtggctc    4320
acgcctgtaa tcccagcact ttagaaggct gaggtgggca gattacttga ggtcaggagt    4380
tcaagaccac cctggccaat atggtgaaac cccggctcta ctaaaaatac aaaaattagc    4440
tgggcatggt ggtgcgcgcc tgtaatccca gctactcggg aggctgaggc tggacaattg    4500
cttggaccca ggaagcagag gttgcagtga gccaagattg tgccactgca ctccagcttg    4560
ggcaacagag ccagactctg taaaaaaaaa aaaaaaaaa aaaaaagaa agaaagaaaa      4620 agaaagaaa gtataaaatc tctttgggtt aacaaaaaaa gatccacaaa acaaacacca     4680
gctcttatca aacttacaca actctgccag agaacaggaa acacaaatac tcattaactc    4740
acttttgtgg caataaaacc ttcatgtcaa aaggagacca ggacacaatg aggaagtaaa    4800
actgcaggcc ctacttgggt gcagagaggg aaaatccaca aataaaacat taccagaagg    4860
agctaagatt tactgcattg agttcattcc ccaggtatgc aaggtgattt taacacctga    4920
aaatcaatca ttgcctttac tacatagaca gattagctag aaaaaaatta caactagcag    4980
aacagaagca atttggcctt cctaaaattc cacatcatat catcatgatg gagacagtgc    5040
agacgccaat gacaataaaa agagggacct ccgtcacccg gtaaacatgt ccacacagct    5100
ccagcaagca cccgtcttcc cagtgaatca ctgtaacctc ccctttaatc agccccaggc    5160
aaggctgcct gcgatggcca cacaggctcc aacccgtggg cctcaacctc ccgcagaggc    5220
tctcctttgg ccaccccatg gggagagcat gaggacaggg cagagccctc tgatgcccac    5280
acatggcagg agctgacgcc agagccatgg gggctggaga gcagagctgc tggggtcaga    5340
gcttcctgag gacacccagg cctaagggaa ggcagctccc tggatggggg caaccaggct    5400
ccgggctcca acctcagagc ccgcatggga ggagccagca ctctaggcct ttcctagggt    5460
gactctgagg ggaccctgac acgacaggat cgctgaatgc acccgagatg aaggggccac    5520
cacgggaccc tgctctcgtg gcagatcagg agagagtggg acaccatgcc aggcccccat    5580
ggcatggctg cgactgaccc aggccactcc cctgcatgca tcagcctcgg taagtcacat    5640
gaccaagccc aggaccaatg tggaaggaag gaaacagcat cccctttagt gatggaaccc    5700
aaggtcagtg caaagagagg ccatgagcag ttaggaaggg tggtccaacc tacagcacaa    5760
accatcatct atcataagta gaagccctgc tccatgaccc ctgcatttaa ataaacgttt    5820
gttaaatgag tcaaattccc tcaccatgag agctcacctg tgtgtaggcc catcacacac    5880
acaaacacac acacacacac acacacacac acacacacac acaggaaag tgcaggatcc    5940 tggacagcac caggcaggct tcacaggcag agcaaacagc gtgaatgacc catgcagtgc    6000
cctgggcccc atcagctcag agaccctgtg agggctgaga tggggctagg caggggagag    6060
acttagagag ggtgggggcct ccaggagggg ggctgcaggg agctgggtac tgccctccag    6120
ggagggggct gcaggagct gggtactgcc ctccagggag gggctgcag ggagctgggt       6180 actgccctcc aggagggggg ctgcaggag ctggtactg ccctcaggg aggggctgc        6240 agggagctgg gtactgccct ccagggaggc aggagcactg ttcccaacag agagcacatc    6300
ttcctgcagc agctgcacag acacaggagc ccccatgact gccctgggcc agggtgtgga    6360
ttccaaattt cgtgccccat tgggtgggac ggaggttgac cgtgacatcc aagggcatc     6420
```

```
tgtgattcca aacttaaact actgtgccta caaaatagga aataacccta cttttttctac    6480
tatctcaaat tccctaagca caagctagca ccctttaaat caggaagttc agtcactcct    6540
ggggtcctcc catgccccca gtctgacttg caggtgcaca gggtggctga catctgtcct    6600
tgctcctcct cttggctcaa ctgccgcccc tcctgggggt gactgatggt caggacaagg    6660
gatcctagag ctggccccat gattgacagg aaggcaggac ttggcctcca ttctgaagac    6720
tagggtgtc aagagagctg ggcatcccac agagctcac aagatgacgc ggacagaggg     6780
tgacacaggg ctcagggctt cagacgggtc gggaggctca gctgagagtt cagggacaga    6840
cctgaggagc ctcagtggga aaagaagcac tgaagtggga agttctggaa tgttctggac    6900
aagcctgagt gctctaagga aatgctccca ccccgatgta gcctgcagca ctggacggtc    6960
tgtgtacctc cccgctgccc atcctctcac agcccccgcc tctagggaca caactcctgc    7020
cctaacatgc atctttcctg tctcattcca cacaaaaggg cctctggggt ccctgttctg    7080
cattgcaagt agtggaggtc acgttcccac agaccaccca gcaacagggt cctatggagg    7140
tgcggtcagg aggatcacac gtccccccat gcccagggga ctgactctgg gggtgatgga    7200
ttggcctgga ggccactggt cccctctgtc cctgagggga atctgcaccc tggaggctgc    7260
cacatccctc ctgattcttt cagctgaggg cccttcttga aatcccaggg aggactcaac    7320
ccccactggg aaaggcccag tgtggacggt tccacagcag cccagctaag gcccttggac    7380
acagatcctg agtgagagaa cctttaggga cacaggtgca cggccatgtc cccagtgccc    7440
acacagagca gggcatctg gaccctgagt gtgtagctcc cgcgactgaa cccagcccct    7500
ccccaatgac gtgacccctg gggtggctcc aggtctccag tccatgccac caaaatctcc    7560
agattgaggg tcctcccttg agtccctgat gcctgtccag gagctgcccc ctgagcaaat    7620
ctagagtgca gagggctggg attgtggcag taaaagcagc cacatttgtc tcaggaagga    7680
aagggaggac atgagctcca ggaagggcga tggcgtcctc tagtgggcgc ctcctgttaa    7740
tgagcaaaaa ggggccagga gagttgagag atcagggctg gccttggact aaggctcaga    7800
tggagaggac tgaggtgcaa agaggggggct gaagtagggg agtggtcggg agagatggga    7860
ggagcaggta agggggaagcc ccagggaggc cgggggaggg tacagcagag ctctccactc    7920
ctcagcattg acatttgggg tggtcgtgct agtgggggttc tgtaagttgt agggtgttca    7980
gcaccatctg gggactctac ccactaaatg ccagcaggac tccctcccca agctctaaca    8040
accaacaatg tctccagact ttccaaatgt cccctggaga gcaaaattgc ttctggcaga    8100
atcactgatc tacgtcagtc tctaaaagtg actcatcagc gaaatccttc acctcttggg    8160
agaagaatca caagtgtgag agggggtagaa actgcagact tcaaaatctt tccaaaagag    8220
ttttacttaa tcagcagttt gatgtcccag gagaagatac atttagagtg tttagagttg    8280
atgccacatg gctgcctgta cctcacagca ggagcagagt gggttttcca agggcctgta    8340
accacaactg gaatgacact cactgggtta cattacaaag tggaatgtgg ggaattctgt    8400
agactttggg aagggaaatg tatgacgtga gcccacagcc taaggcagtg gacagtccac    8460
tttgaggctc tcaccatcta ggagacatct cagccatgaa catagccaca tctgtcatta    8520
gaaaacatgt tttattaaga ggaaaaatct aggctagaag tgctttatgc tcttttttct    8580
ctttatgttc aaattcatat acttttagat cattccttaa agaagaatct atccccctaa    8640
gtaaatgtta tcactgactg gatagtgttg gtgtctcact cccaacccct gtgtggtgac    8700
agtgccctgc ttccccagcc ctgggccctc tctgattcct gagagctttg ggtgctcctt    8760
cattaggagg aagagaggaa gggtgttttt aatattctca ccattcaccc atccacctct    8820
```

-continued

```
tagacactgg gaagaatcag ttgcccactc ttggatttga tcctcgaatt aatgacctct    8880
atttctgtcc cttgtccatt tcaacaatgt gacaggccta agaggtgcct tctccatgtg    8940
atttttgagg agaaggttct caagataagt tttctcacac ctctttgaat tacctccacc    9000
tgtgtcccca tcaccattac cagcagcatt tggaccctt ttctgttagt cagatgcttt     9060
ccacctcttg agggtgtata ctgtatgctc tctacacagg aatatgcaga ggaaatagaa    9120
aaagggaaat cgcattacta ttcagagaga agaagaccttt tatgtgaatg aatgagagtc   9180
taaaatccta agagagccca tataaaatta ttaccagtgc taaaactaca aaagttacac   9240
taacagtaaa ctagaataat aaaacatgca tcacagttgc tggtaaagct aaatcagata   9300
ttttttttctt agaaaagca ttccatgtgt gttgcagtga tgacaggagt gcccttcagt   9360
caatatgctg cctgtaattt ttgttccctg gcagaatgta ttgtcttttc tcccttaaa    9420
tcttaaatgc aaaactaaag gcagctcctg ggccccctcc ccaaagtcag ctgcctgcaa    9480
ccagccccac gaagagcaga ggcctgagct tccctggtca aaataggggg ctagggagct    9540
taaccttgct cgataaagct gtgttcccag aatgtcgctc ctgttcccag gggcaccagc    9600
ctggagggtg gtgagcctca ctggtggcct gatgcttacc ttgtgccctc acaccagtgg    9660
tcactggaac cttgaacact tggctgtcgc ccggatctgc agatgtcaag aacttctgga    9720
agtcaaatta ctgcccactt ctccagggca gataccctgtg aacatccaaa accatgccac   9780
agaaccctgc ctgggtctca acacacatat ggactgtgag caccaagtcc agccctgaat    9840
ctgtgaccac ctgccaagat gcccctaact gggatccacc aatcactgca catggcaggc   9900
agcgaggctt ggaggtgctt cgccacaagg cagccccaat ttgctgggag tttcttggca   9960
cctggtagtg gtgaggagcc ttgggaccct caggattact cccctaagc atagtgggaa   10020
cccttctgca tccccagcag gtgccccgct cttcagagcc tctctctctg aggtttaccc   10080
agacccctgc accaatgaga ccatgctgaa gcctcagaga gagagatgga gctttgacca   10140
ggagccgctc ttccttgagg gccagggcag ggaaagcagg aggcagcacc aggagtggga   10200
acaccagtgt ctaagcccct gatgagaaca gggtggtctc tcccatatgc ccataccagg   10260
cctgtgaaca gaatcctcct tctgcagtga caatgtctga gaggacgaca tgtttcccag   10320
cctaacgtgc agccatgccc atctacccac tgcctactgc aggacagcac caacccagga   10380
gctgggaagc tgggagaaga catggaatac ccatggcttc tcaccttcct ccagtccagt   10440
gggcaccatt tatgcctagg acacccacct gccggcccca ggctcttaag agttaggtca   10500
cctaggtgcc tctgggaggc cgaggcagga gaattgcttg aacccgggag gcagaggttg   10560
cagtgagccg agatcacacc actgcactcc agcctgggtg acagaatgag actctgtctc   10620
aaaaaaaaag agaaagatag catcagtggc taccaagggc taggggcagg ggaaggtgga   10680
gagttaatga ttaatagtat gaagtttcta tgtgagatga tgaaaatgtt ctggaaaaaa   10740
aaatatagtg gtgaggatgt agaatattgt gaatataatt aacggcattt aattgtacac   10800
ttaacatgat taatgtggca tattttatct tatgtatttg actacatcca agaaacactg   10860
ggagagggaa agcccaccat gtaaaataca cccacccta  tcagatagtc ctcattgtac   10920
ccaggtacag gcccctcatg acctgcacag gaataactaa ggatttaagg acatgaggct   10980
tcccagccaa ctgcaggtgc acaacataaa tgtatctgca aacagactga gagtaaagct   11040
ggggcacaa acctcagcac tgccaggaca cacacccttc tcgtggattc tgactttatc   11100
tgacccggcc cactgtccag atcttgttgt gggattggga caagggaggt cataaagcct   11160
gtccccaggg cactctgtgt gagcacacga gacctcccca cccccccacc gttaggtctc   11220
```

```
cacacataga tctgaccatt aggcattgtg aggaggactc tagcgcgggc tcagggatca    11280
caccagagaa tcaggtacag agaggaagac ggggctcgag gagctgatgg atgacacaga    11340
gcagggttcc tgcagtccac aggtccagct caccctggtg taggtgcccc atcccctga    11400
tccaggcatc cctgacacag ctccctcccg gagcctcctc ccaggtgaca catcagggtc    11460
cctcactcaa gctgtccaga gagggcagca ccttggacag cgcccacccc acttcactct    11520
tcctccctca caggctcag ggctcagggc tcaagtctca gaacaaatgg cagaggccag    11580
tgagcccaga gatggtgaca gggcaatgat ccaggggcag ctgcctgaaa cgggagcagg    11640
tgaagccaca gatgggagaa gatggttcag gaagaaaaat ccaggaatgg gcaggagagg    11700
agaggaggac acaggctctg tggggctgca gcccaggatg ggactaagtg tgaagacatc    11760
tcagcaggtg aggccaggtc ccatgaacag agaagcagct cccacctccc ctgatgcacg    11820
gacacacaga gtgtgtggtg ctgtgccccc agagtcgggc tctcctgttc tggtccccag    11880
ggagtgagaa gtgaggttga cttgtccctg ctcctctctg ctaccccaac attccttc     11940
tcctcatgcc cctctctctc aaatatgatt tggatctatg tccccgccca atctcatgt    12000
caaattgtaa accccaatgt tggaggtggg gccttgtgag aagtgattgg ataatgcggg    12060
tggattttct gctttgatgc tgtttctgtg atagagatct cacatgatct ggttgtttaa    12120
aagtgtgtag caccttctccc ctctctctct ctctctctta ctcatgctct gccatgtaag    12180
acgttcctgt ttcccttca ccgtccagaa tgattgtaag ttttctgagg cctccccagg    12240
agcagaagcc actatgcttc ctgtacaact gcagaatgat gagcgaatta aacctctttt    12300
ctttataaat tacccagtct caggtatttc tttatagcaa tgcgaggaca gactaataca    12360
atcttctact cccagatccc cgcacacgct tagccccaga catcactgcc cctgggagca    12420
tgcacagcgc agcctcctgc cgacaaaagc aaagtcacaa aaggtgacaa aaatctgcat    12480
ttggggacat ctgattgtga agaggggagg acagtacact tgtagccaca gagactgggg    12540
ctcaccgagc tgaaacctgg tagcactttg gcataacatg tgcatgaccc gtgttcaatg    12600
tctagagatc agtgttgagt aaaacagcct ggtctggggc cgctgctgtc cccacttccc    12660
tcctgtccac cagagggcgg cagagttcct cccaccctgg agcctcccca ggggctgctg    12720
acctccctca gccgggccca cagcccagca gggtccaccc tcaccgggt cacctcggcc    12780
cacgtcctcc tcgccctccg agctcctcac acggactctg tcagctcctc cctgcagcct    12840
atcggccgcc cacctgaggc ttgtcggccg cccacttgag gcctgtcggc tgccctctgc    12900
aggcagctcc tgtcccctac acccctcct tcccgggct cagctgaaag ggcgtctccc    12960
agggcagctc cctgtgatct ccaggacagc tcagtctctc acaggctccg acgcccccta    13020
tgctgtcacc tcacagccct gtcattacca ttaactcctc agtccatga agttcactga    13080
gcgcctgtct cccggttaca ggaaaactct gtgacaggga ccacgtctgt cctgctctct    13140
gtggaatccc agggcccagc ccagtgcctg acacggaaca gatgctccat aaatactggt    13200
taaatgtgtg ggagatctct aaaaagaagc atatcacctc cgtgtggccc ccagcagtca    13260
gagtctgttc catgtggaca caggggcact ggcaccagca tggaggagg ccagcaagtg    13320
cccgcggctg ccccaggaat gaggcctcaa cccccagagc ttcagaaggg aggacagagg    13380
cctgcaggga atagatcctc cggcctgacc ctgcagccta atccagagtt cagggtcagc    13440
tcacaccacg tcgaccctgg tcagcatccc tagggcagtt ccagacaagg ccggaggtct    13500
cctcttgccc tccagggggt gacattgcac acagacatca ctcaggaaac ggattcccct    13560
ggacaggaac ctggctttgc taaggaagtg gaggtggagc ctggtttcca tcccttgctc    13620
```

-continued

```
caacagaccc ttctgatctc tcccacatac ctgctctgtt cctttctggg tcctatgagg   13680
accctgttct gccaggggtc cctgtgcaac tccagactcc ctcctggtac caccatgggg   13740
aaggtggggt gatcacagga cagtcagcct cgcagagaca gagaccaccc aggactgtca   13800
gggagaacat ggacaggccc tgagccgcag ctcagccaac agacacggag agggagggtc   13860
cccctggagc cttccccaag gacagcagag cccagagtca cccacctccc tccaccacag   13920
tcctctcttt ccaggacaca aagacacct ccccctccac atgcaggatc tggggactcc   13980
tgagacctct gggcctgggt ctccatccct gggtcagtgg cggggttggt ggtactggag   14040
acagagggct ggtccctccc cagccaccac ccagtgagcc tttttctagc ccccagagcc   14100
acctctgtca ccttcctgtt gggcatcatc ccaccttccc agagccctgg agagcatggg   14160
gagacccggg accctgctgg gtttctctgt cacaaaggaa aataatcccc ctggtgtgac   14220
agacccaagg acagaacaca gcagaggtca gcactgggga agacaggttg tcctcccagg   14280
ggatgggggt ccatccacct tgccgaaaag atttgtctga ggaactgaaa atagaaggga   14340
aaaagagga gggacaaaag aggcagaaat gagaggggag gggacagagg acacctgaat   14400
aaagaccaca cccatgaccc acgtgatgct gagaagtact cctgccctag gaagagactc   14460
agggcagagg gaggaaggac agcagaccag acagtcacag cagccttgac aaaacgttcc   14520
tggaactcaa gctcttctcc acagaggagg acagagcaga cagcagagac catggagtct   14580
ccctcggccc ctcccacag atggtgcatc ccctggcaga ggctcctgct cacaggtgaa   14640
gggaggacaa cctgggagag ggtgggagga gggagctggg gtctcctggg taggacaggg   14700
ctgtgagacg gacagagggc tcctgttgga gcctgaatag ggaagaggac atcagagagg   14760
gacaggagtc acaccagaaa aatcaaattg aactggaatt ggaaagggc aggaaaacct   14820
caagagttct attttcctag ttaattgtca ctggccacta cgttttttaaa aatcataata   14880
actgcatcag atgacacttt aaataaaaac ataaccaggg catgaaacac tgtcctcatc   14940
cgcctaccgc ggacattgga aaataagccc caggctgtgg agggccctgg gaaccctcat   15000
gaactcatcc acaggaatct gcagcctgtc ccaggcactg gggtgcaacc aagatc       15056
```

<210> SEQ ID NO 4
<211> LENGTH: 12047
<212> TYPE: DNA
<213> ORGANISM: H. sapiens

<400> SEQUENCE: 4

```
gaattcagaa atagggaag gttgaggaag gacactgaac tcaaagggga tacagtgatt      60
ggtttatttg tcttctcttc acaacattgg tgctggagga attcccaccc tgaggttatg    120
aagatgtctg aacacccaac acatagcact ggagatatga gctcgacaag agtttctcag   180
ccacagagat tcacagccta ggcaggagg acactgtacg ccaggcagaa tgacatggga    240
attgcgctca cgattggctt gaagaagcaa ggactgtggg aggtgggctt tgtagtaaca    300
agagggcagg gtgaactctg attcccatgg gggaatgtga tggtcctgtt acaaattttt    360
caagctggca gggaataaaa cccattacg tgaggacctg tggagggcgg ctgccccaac    420
tgataaagga aatagccagg tgggggcctt tccccattgta ggggggacat atctggcaat   480
agaagccttt gagaccctt aggtacaag tactgaggca gcaaataaaa tgaaatctta      540
tttttcaact ttatactgca tgggtgtgaa gatatatttg tttctgtaca gggggtgagg    600
gaaaggaggg gaggaggaaa gttcctgcag gtctggtttg gtcttgtgat ccaggggtc     660
ttggaactat ttaaattaaa ttaaattaaa acaagcgact gttttaaatt aaattaaatt    720
```

| | | | | |
|---|---|---|---|---|
| aaattaaatt | ttactttatt | ttatcttaag | ttctgggcta | catgtgcagg acgtgcagct | 780 |
| ttgttacata | ggtaaacgtg | tgccatggtg | gtttgctgta | cctatcaacc catcacctag | 840 |
| gtattaagcc | cagcatgcat | tagctgtttt | tcctgacgct | ctccctctcc ctgactccca | 900 |
| caacaggccc | cagtgtgtgt | tgttccctc | cctgtgtcca | tgtgttctca ttgttcagct | 960 |
| cccacttata | agtgagaaca | tgtggtgttt | ggttttctgt | ttctgtgtta gtttgctgag | 1020 |
| gataatggct | tccacctcca | tccatgttcc | tgcaaaggac | gtgatcttat tctttttat | 1080 |
| ggttgcatag | aaattgtttt | tacaaatcca | attgatattg | tatttaatta caagttaatc | 1140 |
| taattagcat | actagaagag | attacagaag | atattaggta | cattgaatga ggaaatatat | 1200 |
| aaaataggac | gaaggtgaaa | tattaggtag | gaaaagtata | atagttgaaa gaagtaaaaa | 1260 |
| aaaatatgca | tgagtagcag | aatgtaaaag | aggtgaagaa | cgtaatagtg acttttaga | 1320 |
| ccagattgaa | ggacagagac | agaaaaattt | taaggaattg | ctaaaccatg tgagtgttag | 1380 |
| aagtacagtc | aataacatta | aagcctcagg | aggagaaaag | aataggaaag gaggaaatat | 1440 |
| gtgaataaat | agtagagaca | tgtttgatgg | attttaaaat | atttgaaaga cctcacatca | 1500 |
| aaggattcat | accgtgccat | tgaagaggaa | gatggaaaag | ccaagaagcc agatgaaagt | 1560 |
| tagaaatatt | attggcaaag | cttaaatgtt | aaaagtccta | gagagaaagg atggcagaaa | 1620 |
| tattggcggg | aaagaatgca | gaacctagaa | tataaattca | tcccaacagt ttggtagtgt | 1680 |
| gcagctgtag | ccttttctag | ataatacact | attgtcatac | atcgcttaag cgagtgtaaa | 1740 |
| atggtctcct | cactttattt | atttatatat | ttatttagtt | ttgagatgga gcctcgctct | 1800 |
| gtctcctagg | ctggagtgca | atagtgcgat | accactcact | gcaacctctg cctcctctgt | 1860 |
| tcaagtgatt | tcttacctc | agcctcccga | gtagctggga | ttacaggtgc gtgccaccac | 1920 |
| acccggctaa | tttttgtatt | ttttgtagag | acggggtttt | gccatgttgg ccaggctggt | 1980 |
| cttgaactcc | tgacatcagg | tgatccacct | gccttggcct | cctaaagtgc tgggattaca | 2040 |
| ggcatgagcc | accgtgccca | accactttat | ttatttta | ttttattttt taaatttcag | 2100 |
| cttctatttg | aaatacaggg | ggcacatata | taggattgtt | acatgggtat attgaactca | 2160 |
| ggtagtgatc | atactaccca | acaggtaggt | tttcaaccca | ctcccccctct tttcctcccc | 2220 |
| attctagtag | tgtgcagtgt | ctattgttct | catgtttatg | tctatgtgtg ctccaggttt | 2280 |
| agctcccacc | tgtaagtgag | aacgtgtggt | atttgatttt | ctgtccctgt gttaattcac | 2340 |
| ttaggattat | ggcttccagc | tccattcata | ttgctgtaaa | ggatatgatt cattttttcat | 2400 |
| ggccatgcag | tattccatat | tgcgtataga | tcacattttc | tttctttttt tttttgaga | 2460 |
| cggagtcttg | ctttgctgcc | taggctggag | tgcagtagca | cgatctcggc tcactgcaag | 2520 |
| cttcacctcc | ggggttcacg | tcattcttct | gtctcagctt | cccaagtagc tgggactaca | 2580 |
| ggcgcccgcc | accacgtccg | gctaatttt | ttgtgtgttt | ttagtagaga tgggggtttc | 2640 |
| actgtgttag | ccaggatggt | cttgatctcc | tgaccttgtg | gtccacctgc ctcggtctcc | 2700 |
| caaagtgctg | ggattacagg | ggtgagccac | tgcgcccggc | ccatatatac cacatttct | 2760 |
| ttaaccaatc | caccattgat | gggcaactag | gtagattcca | tggattccac agttttgcta | 2820 |
| ttgtgtgcag | tgtggcagta | gacatatgaa | tgaatgtgtc | ttttggtat aatgatttgc | 2880 |
| attcctttgg | gtatacagtc | attaatagga | gtgctgggtt | gaacggtggc tctgtttaaa | 2940 |
| attctttgag | aatttttccaa | actgtttgcc | atagagagca | aactaattta catttccacg | 3000 |
| aacagtatat | aagcattccc | ttttctccac | agctttgtca | tcatggtttt tttttttctt | 3060 |
| tatttttaaaa | aagaatatgt | tgttgttttc | ccagggtaca | tgtgcaggat gtgcaggttt | 3120 |

-continued

```
gttacatagg tagtaaacgt gagccatggt ggtttgctgc acctgtcaac ccattacctg    3180
ggtatgaagc cctgcctgca ttagctcttt tccctaatgc tctcactact gccccaccct    3240
caccctgaca gggcaaacag acaacctaca gaatgggagg aaattttgc aatctattca     3300 tctgacaaag gtcaagaata tccagaatct acaaggaact taagcaaatt tttactttt     3360 aataatagcc actctgactg gcgtgaaatg gtatctcatt gtggttttca tttgaattc     3420 tctgatgatc agtgacgatg agcatttttt catatttgtt ggctgcttgt acgtcttttg    3480
agaagtgtct cttcatgcct tttggccact ttaatgggat tatttttgc ttttagttt      3540 aagttccta tagattctgg atattagact tcttattgga tgcatagttt gtgaatactc     3600
tcttccattc tgtaggttgt ctgtttactc tattgatggc ttcttttgct gtgccgaagc    3660
atcttagttt aattagaaac cacctgccaa ttttgtttt tgttgcaatt gcttttgggg     3720
acttagtcat aaactctttg ccaaggtctg ggtcaagaag agtatttcct aggtttcct    3780 ctagaatttt gaaagtctga atgtaaacat ttgcatttt aatgcatctt gagttagttt    3840
ttgtatatgt gaaaggtcta ctctcatttt cttccctct ttctttcttt ctttcttttc    3900 tttcttctt tctttctttc tttctttctt tcttcttc tttcttttg tccttctttc        3960 tttcttcctt tctctttctt tctctctttc ttttttttt tgatggagt attgctctgt     4020 tgcccaggct gcagtgcagc ggcacgatct cggctcactg caacctctgc ctcctgggtt    4080
caactgattc tcctgcatca gccttccaag tagctgggat tataggcgcc cgccaccacg    4140
cccgactaat ttttgtattt ttagtagaga cggggttgtg ccatgttggc caggctggtt    4200
tgaaactcct gacctcaaac gatctgcctg ccttggcctc ccaaagtgct gggattacag    4260
gtgtgagcca ctgtgcccag ccaagaatgt catttctaa gaggtccaag aacctcaaga    4320
tattttggga ccttgagaag agaggaattc atacaggtat tacaagcaca gcctaatggc    4380
aaatctttgg catggcttgg cttcaagact ttaggctctt aaaagtcgaa tccaaaaatt    4440
tttataaaag ctccagctaa gctaccttaa aaggggcctg tatggctgat cactcttctt    4500
gctatacttt acacaaataa acaggccaaa tataatgagg ccaaaatta tttgcaaat    4560 aaattggtcc tgctatgatt tactcttggt aagaacaggg aaaatagaga aaatttaga    4620 ttgcatctga ccttttttc tgaattttta tatgtgccta caatttgagc taaatcctga    4680 attatttct ggttgcaaaa actctctaaa gaagaacttg gttttcattg tcttcgtgac    4740
acatttatct ggctctttac tagaacagct ttcttgtttt tggtgttcta gcttgtgtgc    4800
cttacagttc tactcttcaa attattgtta tgtgtatctc atagttttcc ttcttttgag    4860
aaaactgaag ccatggtatt ctgaggacta gagatgactc aacagagctg gtgaatctcc    4920
tcatatgcaa tccactgggc tcgatctgct tcaaattgct gatgcactgc tgctaaagct    4980
atacatttaa aaccctcact aaaggatcag ggaccatcat ggaagaggag gaaacatgaa    5040
attgtaagag ccagattcgg ggggtagagt gtggaggtca gagcaactcc accttgaata    5100
agaaggtaaa gcaacctatc ctgaaagcta acctgccatg gtggcttctg attaacctct    5160
gttctaggaa gactgacagt ttgggtctgt gtcattgccc aaatctcatg ttaaattgta    5220
atccccagtg ttcggaggtg ggacttggtg gtaggtgatt cggtcatggg agtagatttt    5280
cttctttgtg gtgttacagt gatagtgagt gagttctcgt gagatctggt catttaaaag    5340
tgtgtggccc ctcccctccc tctcttggtc ctcctactgc catgtaagat acctgctcct    5400
gctttgcctt ctaccataag taaaagcccc ctgaggcctc cccagaagca gatgccacca    5460
tgcttcctgt acagcctgca gaaccatcag ccaattaaac ctcttttctg tataaattac    5520
```

-continued

| | |
|---|---|
| cagtcttgag tatctcttta cagcagtgtg agaacggact aatacaaggg tctccaaaat | 5580 |
| tccaagttta tgtattcttt cttgccaaat agcaggtatt taccataaat cctgtcctta | 5640 |
| ggtcaaacaa ccttgatggc atcgtacttc aattgtctta cacattcctt ctgaatgact | 5700 |
| cctcccctat ggcatataag ccctgggtct tgggggataa tggcagaggg gtccaccatc | 5760 |
| ttgtctggct gccacctgag acacggacat ggcttctgtt ggtaagtctc tattaaatgt | 5820 |
| ttctttctaa gaaactggat ttgtcagctt gtttctttgg cctctcagct tcctcagact | 5880 |
| ttggggtagg ttgcacaacc ctgcccacca cgaaacaaat gtttaatatg ataaatatgg | 5940 |
| atagatataa tccacataaa taaaagctct tggagggccc tcaataattg ttaagagtgt | 6000 |
| aaatgtgtcc aaagatggaa atgtttgag aactactgtc ccagagattt tcctgagttc | 6060 |
| tagagtgtgg gaatatagaa cctggagctt ggcttcttca gcctagaatc aggagtatgg | 6120 |
| ggctgaagtc tgaagcttgg cttcagcagt ttggggttgg cttccggagc acatatttga | 6180 |
| catgttgcga ctgtgatttg gggtttggta tttgctctga atcctaatgt ctgtccttga | 6240 |
| ggcatctaga atctgaaatc tgtggtcaga attctattat cttgagtagg acatctccag | 6300 |
| tcctggttct gccttctagg gctggagtct gtagtcagtg acccggtctg gcatttcaac | 6360 |
| ttcatataca gtgggctatc ttttggtcca tgtttcaacc aaacaaccga ataaaccatt | 6420 |
| agaacctttc cccacttccc tagctgcaat gttaaaccta ggatttctgt ttaataggtt | 6480 |
| catatgaata atttcagcct gatccaactt tacattcctt ctaccgttat tctacaccca | 6540 |
| ccttaaaaat gcattcccaa tatattccct ggattctacc tatatatggt aatcctggct | 6600 |
| ttgccagttt ctagtgcatt aacatacctg atttacattc ttttacttta aagtggaaat | 6660 |
| aagagtccct ctgcagagtt caggagttct caagatggcc cttacttctg acatcaattg | 6720 |
| agatttcaag ggagtcgcca agatcatcct caggttcagt gattgctggt agccctcata | 6780 |
| taactcaatg aaagctgtta tgctcatggc tatggtttat tacagcaaaa gaatagagat | 6840 |
| gaaaatctag caagggaaga gttgcatggg gcaaagacaa ggagagctcc aagtgcagag | 6900 |
| attcctgttg ttttctccca gtggtgtcat ggaaagcagt atcttctcca tacaatgatg | 6960 |
| tgtgataata ttcagtgtat tgccaatcag ggaactcaac tgagccttga ttatattgga | 7020 |
| gcttggttgc acagacatgt cgaccacctt catggctgaa ctttagtact tagccccctcc | 7080 |
| agacgtctac agctgatagg ctgtaaccca acattgtcac cataaatcac attgttagac | 7140 |
| tatccagtgt ggcccaagct cccgtgtaaa cacaggcact ctaaacaggc aggatatttc | 7200 |
| aaaagcttag agatgacctc ccaggagctg aatgcaaaga cctggcctct ttgggcaagg | 7260 |
| agaatccttt accgcacact ctccttcaca gggttattgt gaggatcaaa tgtggtcatg | 7320 |
| tgtgtgagac accagcacat gtctggctgt ggagagtgac ttctatgtgt gctaacattg | 7380 |
| ctgagtgcta agaaagtatt aggcatggct ttcagcactc acagatgctc atctaatcct | 7440 |
| cacaacatgg ctacagggtg ggcactacta gcctcatttg acagaggaaa ggactgtgga | 7500 |
| taagaagggg gtgaccaata ggtcagagtc attctggatg caaggggctc cagaggacca | 7560 |
| tgattagaca ttgtctgcag agaaattatg gctggatgtc tctgcccggg aaagggggat | 7620 |
| gcactttcct tgacccccta tctcagatct tgactttgag gttatctcag acttcctcta | 7680 |
| tgataccagg agcccatcat aatctctctg tgtcctctcc ccttcctcag tcttactgcc | 7740 |
| cactcttccc agctccatct ccagctggcc aggtgtagcc acagtaccta actctttgca | 7800 |
| gagaactata aatgtgtatc ctacaggga gaaaaaaaaa aagaactctg aaagagctga | 7860 |
| cattttaccg acttgcaaac acataagcta acctgccagt tttgtgctgg tagaactcat | 7920 |

-continued

```
gagactcctg ggtcagaggc aaaagatttt attacccaca gctaaggagg cagcatgaac    7980
tttgtgttca catttgttca ctttgccccc caattcatat gggatgatca gagcagttca    8040
ggtggatgga cacagggtt tgtggcaaag gtgagcaacc taggcttaga aatcctcaat     8100
cttataagaa ggtactagca aacttgtcca gtctttgtat ctgacggaga tattatcttt    8160
ataattgggt tgaaagcaga cctactctgg aggaacatat tgtatttatt gtcctgaaca    8220
gtaaacaaat ctgctgtaaa atagacgtta actttattat ctaaggcagt aagcaaacct    8280
agatctgaag gcgataccat cttgcaaggc tatctgctgt acaaatatgc ttgaaaagat    8340
ggtccagaaa agaaaacggt attattgcct ttgctcagaa gacacacaga aacataagag    8400
aaccatggaa aattgtctcc caacactgtt cacccagagc cttccactct tgtctgcagg    8460
acagtcttaa catcccatca ttagtgtgtc taccacatct ggcttcaccg tgcctaacca    8520
agatttctag gtccagttcc ccaccatgtt tggcagtgcc ccactgccaa ccccagaata    8580
agggagtgct cagaattccg aggggacatg ggtggggatc agaacttctg ggcttgagtg    8640
cagaggggggc ccatactcct tggttccgaa ggaggaagag gctggaggtg aatgtccttg   8700
gaggggagga atgtgggttc tgaactctta aatccccaag ggaggagact ggtaaggtcc    8760
cagcttccga ggtactgacg tgggaatggc ctgagaggtc taagaatccc gtatcctcgg    8820
gaaggagggg ctgaaattgt gaggggttga gttgcagggg tttgttagct tgagactcct    8880
tggtgggtcc ctgggaagca aggactggaa ccattggctc caggggtttgg tgtgaaggta   8940
atgggatctc ctgattctca aagggtcaga ggactgagag ttgcccatgc tttgatcttt    9000
ccatctactc cttactccac ttgagggtaa tcacctactc ttctagttcc acaagagtgc    9060
gcctgcgcga gtataatctg cacatgtgcc atgtcccgag gcctggggca tcatccactc    9120
atcattcagc atctgcgcta tgcgggcgag gccggcgcca tgacgtcatg tagctgcgac    9180
tatccctgca gcgcgcctct cccgtcacgt cccaaccatg gagctgtgga cgtgcgtccc    9240
ctggtggatg tggcctgcgt ggtgccaggc cggggcctgg tgtccgataa agatcctaga    9300
accacaggaa accaggactg aaaggtgcta gagaatggcc atatgtcgct gtccatgaaa    9360
tctcaaggac ttctgggtgg agggcacagg agcctgaact tacgggtttg ccccagtcca    9420
ctgtcctccc aagtgagtct cccagatacg aggcactgtg ccagcatcag cttcatctgt    9480
accacatctt gtaacaggga ctacccagga ccctgatgaa caccatggtg tgtgcaggaa    9540
gaggggtga aggcatggac tcctgtgtgg tcagagccca gaggggcca tgacgggtgg     9600
ggaggaggct gtggactggc tcgagaagtg ggatgtggtt gtgtttgatt cctttggcc    9660
agataaagtg ctggatatag cattgaaaac ggagtatgaa gaccagttag aatggagggt    9720
caggttggag ttgagttaca gatggggtaa aattctgctt cggatgagtt tggggattgg    9780
caatctaaag gtggtttggg atggcatggc tttgggatgg aaataggttt gttttatgt    9840
tggctgggaa gggtgtgggg attgaattgg ggatgaagta ggtttagttt ggagataga    9900
atacatggag ctggctattg catgcgagga tgtgcattag tttggtttga tctttaaata    9960
aaggaggcta ttagggttgt cttgaattag attaagttgt gttgggttga tgggttggc    10020
ttgtgggtga tgtggttgga ttgggctgtg ttaaattggt ttgggtcagg ttttggttga    10080
ggttatcatg gggatgagga tatgcttggg acatggattc aggtggttct cattcaagct    10140
gaggcaaatt tcctttcaga cggtcattcc agggaacgag tggttgtgtg ggggaaatca    10200
ggccactggc tgtgaatatc cctctatcct ggtcttgaat tgtgattatc tatgtccatt    10260
ctgtctcctt cactgtactt ggaattgatc tggtcattca gctggaaatg ggggaagatt    10320
```

```
ttgtcaaatt cttgagacac agctgggtct ggatcagcgt aagccttcct tctggtttta    10380
ttgaacagat gaaatcacat tttttttttc aaaatcacag aaatcttata gagttaacag    10440
tggactctta taataagagt taacaccagg actcttattc ttgattcttt tctgagacac    10500
caaaatgaga tttctcaatg ccaccctaat tcttttttttt tttttttttt tttttgagac    10560
acagtctggg tcttttgctc tgtcactcag gctggagcgc agtggtgtga tcatagctca    10620 ctgaacccctt gacctcctgg acttaaggga tcctcctgct tcagcctcct gagtagatgg    10680
ggctacaggt gcttgccacc acacctggct aattaaattt tttttttttt tttgtagaga    10740
aagggtctca ctttgttgcc ctggctgatc ttgaacttct gacttcaagt gattcttcag    10800
ccttggactc ccaaagcact gggattgctg gcatgagcca ctcaccgtgc ctggcttgca    10860
gcttaatctt ggagtgtata aacctggctc ctgatagcta gacatttcag tgagaaggag    10920
gcattggatt ttgcatgagg acaattctga cctaggaggg caggtcaaca ggaatccccg    10980
ctgtacctgt acgttgtaca ggcatggaga atgaggagtg aggaggccgt accggaaccc    11040
catattgttt agtggacatt ggattttgaa ataataggga acttggtctg ggagagtcat    11100
atttctggat tggacaatat gtggtatcac aaggttttat gatgagggag aaatgtatgt    11160
ggggaaccat tttctgagtg tggaagtgca agaatcagag agtagctgaa tgccaacgct    11220
tctatttcag gaacatggta agttggaggt ccagctctcg ggctcagacg ggtatagggga    11280 ccaggaagtc tcacaatccg atcattctga tatttcaggg catattaggt ttgggtgca    11340 aaggaagtac ttgggactta ggcacatgag actttgtatt gaaatcaat gattgggct    11400 ggccgtggtg ctcacgcctg taatctcatc actttgggag accgaagtgg gaggatggct    11460
tgatctcaag agttggacac cagcctaggc aacatggcca gaccctctct ctacaaaaaa    11520
attaaaaatt agctggatgt ggtggtgcat gcttgtggtc tcagctatcc tggaggctga    11580
gacaggagaa tcggttgagt ctgggagttc aaggctacag ggagctgcga tcacgccgct    11640
gcactccagc ctgggaaaca gagtgagact gtctcagaat ttttttaaaa aagaatcagt    11700
gatcatccca acctgttg ctgttcatcc tgagcctgcc ttctctggct tgttcccta     11760 gatcacatct ccatgatcca taggccctgc ccaatctgac ctcacaccgt gggaatgcct    11820
ccagactgat ctagtatgtg tggaacagca agtgctggct ctccctcccc ttccacagct    11880
ctgggtgtgg gaggggggttg tccagcctcc agcagcatgg ggagggcctt ggtcagcatc    11940
taggtgccaa cagggcaagg gcggggtcct ggagaatgaa ggctttatag ggctcctcag    12000
ggaggccccc cagccccaaa ctgcaccacc tggccgtgga caccggt                  12047
```

<210> SEQ ID NO 5
<211> LENGTH: 858
<212> TYPE: DNA
<213> ORGANISM: H. sapiens

<400> SEQUENCE: 5

```
cgagcggccc ctcagcttcg gcgcccagcc ccgcaaggct cccggtgacc actagagggc      60
gggaggagct cctggccagt ggtggagagt ggcaaggaag gacccctaggg ttcatcggag     120 cccaggttta ctcccttaag tggaaatttc ttccccccact cctccttggc tttctccaag    180
gagggaaccc aggctgctgg aaagtccggc tgggcggggg actgtggggtt cagggggagaa   240 cggggtgtgg aacgggacag ggagcggtta aagggtggg gctattccgg gaagtggtgg      300
ggggagggag cccaaaacta gcacctagtc cactcattat ccagcccctct tatttctcgg    360 ccgctctgct tcagtggacc cggggagggc ggggaagtgg agtgggagac ctaggggtgg     420
```

```
gcttcccgac cttgctgtac aggacctcga cctagctggc tttgttcccc atccccacgt      480
tagttgttgc cctgaggcta aaactagagc ccaggggccc caagttccag actgcccctc      540 cccctcccc cggagccagg gagtggttgg tgaaaggggg aggccagctg gagaacaaac      600
gggtagtcag ggggttgagc gattagagcc cttgtaccct acccaggaat ggttggggag      660
gaggaggaag aggtaggagg taggggaggg ggcggggttt tgtcacctgt cacctgctcg      720
ctgtgcctag ggcgggcggg cggggagtgg ggggaccggt ataaagcggt aggcgcctgt      780
gcccgctcca cctctcaagc agccagcgcc tgcctgaatc tgttctgccc cctccccacc      840
catttcacca ccaccatg                                                    858

<210> SEQ ID NO 6
<211> LENGTH: 454
<212> TYPE: DNA
<213> ORGANISM: R. rattus

<400> SEQUENCE: 6
aagcttccac aagtgcattt agcctctcca gtattgctga tgaatccaca gttcaggttc       60
aatggcgttc aaaacttgat caaaaatgac cagactttat attcttacac caacatctat      120
ctgattggag aatggataa tagtcatcat gtttaaacat ctaccattcc agttaagaaa       180
atatgatagc atcttgttct tagtcttttt cttaataggg acataaagcc cacaaataaa      240
aatatgcctg aagaatggga caggcattgg gcattgtcca tgcctagtaa agtactccaa      300
gaacctattt gtatactaga tgacacaatg tcaatgtctg tgtacaactg ccaactggga      360
tgcaagacac tgcccatgcc aatcatcctg aaaagcagct ataaaaagca ggaagctact      420
ctgcaccttg tcagtgaggt ccagatacct acag                                  454

<210> SEQ ID NO 7
<211> LENGTH: 307
<212> TYPE: DNA
<213> ORGANISM: Adenovirus
<220> FEATURE:
<221> NAME/KEY: CDS
<222> LOCATION: (20)...(304)

<400> SEQUENCE: 7
gatgaccggc tcaaccatc gcg ccc aca acg gac tat cgc aac acc act gct        52
                     Ala Pro Thr Thr Asp Tyr Arg Asn Thr Thr Ala
                      1               5                  10 acc gga cta aca tct gcc cta aat tta ccc caa gtt cat gcc ttt gtc        100
Thr Gly Leu Thr Ser Ala Leu Asn Leu Pro Gln Val His Ala Phe Val
             15                  20                  25 aat gac tgg gcg agc ttg gac atg tgg tgg ttt tcc ata gcg ctt atg        148
Asn Asp Trp Ala Ser Leu Asp Met Trp Trp Phe Ser Ile Ala Leu Met
         30                  35                  40 ttt gtt tgc ctt att att atg tgg ctt att tgt tgc cta aag cgc aga        196
Phe Val Cys Leu Ile Ile Met Trp Leu Ile Cys Cys Leu Lys Arg Arg
     45                  50                  55 cgc gcc aga ccc ccc atc tat agg cct atc att gtg ctc aac cca cac        244
Arg Ala Arg Pro Pro Ile Tyr Arg Pro Ile Ile Val Leu Asn Pro His
 60                  65                  70                  75 aat gaa aaa att cat aga ttg gac ggt ctg aaa cca tgt tct ctt ctt        292
Asn Glu Lys Ile His Arg Leu Asp Gly Leu Lys Pro Cys Ser Leu Leu
                 80                  85                  90 tta cag tat gat taa                                                    307
Leu Gln Tyr Asp
         95
```

```
<210> SEQ ID NO 8
<211> LENGTH: 95
<212> TYPE: PRT
<213> ORGANISM: Adenovirus

<400> SEQUENCE: 8

Ala Pro Thr Thr Asp Tyr Arg Asn Thr Thr Ala Thr Gly Leu Thr Ser
 1               5                  10                  15

Ala Leu Asn Leu Pro Gln Val His Ala Phe Val Asn Asp Trp Ala Ser
             20                  25                  30

Leu Asp Met Trp Trp Phe Ser Ile Ala Leu Met Phe Val Cys Leu Ile
         35                  40                  45

Ile Met Trp Leu Ile Cys Cys Leu Lys Arg Arg Arg Ala Arg Pro Pro
     50                  55                  60

Ile Tyr Arg Pro Ile Ile Val Leu Asn Pro His Asn Glu Lys Ile His
65                  70                  75                  80

Arg Leu Asp Gly Leu Lys Pro Cys Ser Leu Leu Leu Gln Tyr Asp
                 85                  90                  95
```